United States Patent
White

(10) Patent No.: US 9,301,860 B2
(45) Date of Patent: Apr. 5, 2016

(54) ARTICULATED COMMISSURE VALVE STENTS AND METHODS

(71) Applicant: Jenesis Surgical, LLC, Charlestown, RI (US)

(72) Inventor: Jennifer K. White, Charlestown, RI (US)

(73) Assignee: Jenesis Surgical, LLC, Charlestown, RI (US)

(*) Notice: Subject to any disclaimer, the term of this patent is extended or adjusted under 35 U.S.C. 154(b) by 0 days.

(21) Appl. No.: 14/205,301

(22) Filed: Mar. 11, 2014

(65) Prior Publication Data

US 2014/0277563 A1 Sep. 18, 2014

Related U.S. Application Data

(60) Provisional application No. 61/780,670, filed on Mar. 13, 2013.

(51) Int. Cl.
| | | |
|---|---|---|
| *A61F 2/82* | (2013.01) | |
| *A61F 2/24* | (2006.01) | |
| *A61F 2/844* | (2013.01) | |

(52) U.S. Cl.
CPC ............... *A61F 2/82* (2013.01); *A61F 2/2418* (2013.01); *A61F 2/243* (2013.01); *A61F 2/2412* (2013.01); *A61F 2/844* (2013.01)

(58) Field of Classification Search
CPC ............. A61F 2/82; A61F 2/885; A61F 2/24; A61F 2/243
See application file for complete search history.

(56) References Cited

U.S. PATENT DOCUMENTS

| | | | |
|---|---|---|---|
| 3,548,417 | A | 12/1970 | Kischer et al. |
| 4,289,123 | A | 9/1981 | Dunn |
| 5,122,154 | A | 6/1992 | Rhodes |
| 5,171,278 | A | 12/1992 | Pisharodi |
| 5,503,497 | A | 4/1996 | Dudley et al. |
| 5,545,214 | A | 8/1996 | Stevens |
| 5,593,417 | A | 1/1997 | Rhodes |
| 5,643,339 | A | 7/1997 | Kavteladze et al. |
| 5,735,842 | A | 4/1998 | Krueger et al. |
| 5,776,181 | A | 7/1998 | Lee et al. |

(Continued)

FOREIGN PATENT DOCUMENTS

| | | |
|---|---|---|
| EP | 1671608 B1 | 7/2008 |
| EP | 1343438 B1 | 7/2009 |

(Continued)

OTHER PUBLICATIONS

International Preliminary Report on Patentability received for PCT Patent Application No. PCT/US2009/051324, mailed on Feb. 3, 2011, 7 pages.

(Continued)

*Primary Examiner* — Thomas J Sweet
*Assistant Examiner* — Daniel Bissing
(74) *Attorney, Agent, or Firm* — Morrison & Foerster LLP

(57) ABSTRACT

A support structure includes strut members interconnected by rotatable joints to form a series of linked scissor mechanisms. The structure can be remotely actuated to compress or expand its shape by adjusting the scissor joints within a range of motion. In particular, the support structure can be repositioned within the body lumen or retrieved from the lumen. The support structure can be employed to introduce and support a prosthetic valve within a body lumen.

13 Claims, 45 Drawing Sheets

(56) References Cited

U.S. PATENT DOCUMENTS

| | | |
|---|---|---|
| 5,827,321 A | 10/1998 | Roubin et al. |
| 5,871,536 A | 2/1999 | Lazarus |
| 5,968,091 A | 10/1999 | Pinchuk et al. |
| 6,063,113 A | 5/2000 | Kavteladze et al. |
| 6,146,394 A | 11/2000 | Morejohn et al. |
| 6,183,517 B1 | 2/2001 | Suddaby |
| 6,245,102 B1 | 6/2001 | Jayaraman |
| 6,261,318 B1 | 7/2001 | Lee et al. |
| 6,348,061 B1 | 2/2002 | Whitman |
| 6,454,799 B1 | 9/2002 | Schreck |
| 6,475,237 B2 | 11/2002 | Drasler et al. |
| 6,530,952 B2 | 3/2003 | Vesely |
| 6,569,196 B1 | 5/2003 | Vesely |
| 6,596,021 B1 | 7/2003 | Lootz |
| 6,666,885 B2 | 12/2003 | Moe |
| 6,685,737 B1 | 2/2004 | Pacetti |
| 6,716,230 B2 | 4/2004 | Whitman |
| 6,730,118 B2 | 5/2004 | Spenser et al. |
| 6,872,226 B2 | 3/2005 | Cali et al. |
| 6,893,460 B2 | 5/2005 | Spenser et al. |
| 7,007,396 B2 | 3/2006 | Rudko et al. |
| 7,011,681 B2 | 3/2006 | Vesely |
| 7,041,132 B2 | 5/2006 | Quijano et al. |
| 7,056,338 B2 | 6/2006 | Shanley et al. |
| 7,097,658 B2 | 8/2006 | Oktay |
| 7,141,063 B2 | 11/2006 | White et al. |
| 7,186,265 B2 | 3/2007 | Sharkawy et al. |
| 7,329,279 B2 | 2/2008 | Haug et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,402,169 B2 | 7/2008 | Killion et al. |
| 7,404,823 B2 | 7/2008 | Gregorich et al. |
| 7,429,268 B2 | 9/2008 | Shanley et al. |
| 7,431,732 B2 | 10/2008 | Moriuchi et al. |
| 7,438,721 B2 | 10/2008 | Doig et al. |
| 7,458,985 B2 | 12/2008 | Madda et al. |
| 7,479,158 B2 | 1/2009 | Gregorich |
| 7,491,227 B2 | 2/2009 | Yang |
| 7,500,986 B2 | 3/2009 | Lye et al. |
| 7,500,988 B1 | 3/2009 | Butaric et al. |
| 7,503,930 B2 | 3/2009 | Sharkawy et al. |
| 7,510,570 B1 | 3/2009 | Goicoechea et al. |
| 7,510,575 B2 | 3/2009 | Spenser et al. |
| 7,582,110 B2 | 9/2009 | Case et al. |
| 7,591,848 B2 | 9/2009 | Allen |
| 7,594,974 B2 | 9/2009 | Cali et al. |
| 7,597,710 B2 | 10/2009 | Obermiller |
| 7,628,802 B2 | 12/2009 | White et al. |
| 8,226,707 B2 | 7/2012 | White |
| 8,603,160 B2 | 12/2013 | Salahieh et al. |
| 8,685,080 B2 | 4/2014 | White |
| 2003/0040791 A1 | 2/2003 | Oktay |
| 2005/0137688 A1 | 6/2005 | Salahieh et al. |
| 2005/0283231 A1 | 12/2005 | Haug et al. |
| 2006/0111772 A1 | 5/2006 | White et al. |
| 2006/0135964 A1 | 6/2006 | Vesely |
| 2006/0173524 A1 | 8/2006 | Salahieh et al. |
| 2008/0004696 A1 | 1/2008 | Vesely |
| 2008/0071356 A1 | 3/2008 | Greenhalgh et al. |
| 2008/0125859 A1 | 5/2008 | Salahieh et al. |
| 2008/0140189 A1 | 6/2008 | Nguyen et al. |
| 2008/0183275 A1 | 7/2008 | Schmid et al. |
| 2009/0054969 A1 | 2/2009 | Salahieh et al. |
| 2009/0082844 A1 | 3/2009 | Zacharias et al. |
| 2009/0210052 A1 | 8/2009 | Forster et al. |
| 2009/0240320 A1 | 9/2009 | Tuval et al. |
| 2010/0004739 A1 | 1/2010 | Vesely |
| 2011/0106115 A1 | 5/2011 | Haselby et al. |
| 2011/0219603 A1* | 9/2011 | White .................. A61F 2/2412 29/428 |
| 2011/0224781 A1 | 9/2011 | White |
| 2011/0230956 A1 | 9/2011 | White |
| 2011/0245918 A1 | 10/2011 | White |
| 2011/0288629 A1 | 11/2011 | White |
| 2011/0288632 A1 | 11/2011 | White |
| 2013/0046373 A1 | 2/2013 | Cartledge et al. |

FOREIGN PATENT DOCUMENTS

| | | |
|---|---|---|
| EP | 1872743 B1 | 8/2009 |
| EP | 1049425 B1 | 11/2009 |
| EP | 2138132 A2 | 12/2009 |
| JP | 52-62850 A | 5/1977 |
| JP | 59-8499 U | 1/1984 |
| JP | 5-317204 A | 12/1993 |
| JP | 7-2396 U | 1/1995 |
| JP | 3071573 U | 9/2000 |
| JP | 2007-534381 A | 11/2007 |
| JP | 2008-29506 A | 2/2008 |
| WO | 95/13033 A1 | 5/1995 |
| WO | 99/33414 A1 | 7/1999 |
| WO | 02/49540 A2 | 6/2002 |
| WO | 02/49540 A3 | 2/2003 |
| WO | 03/018100 A1 | 3/2003 |
| WO | 03/047468 A1 | 6/2003 |
| WO | 03/075797 A2 | 9/2003 |
| WO | 2005/102015 A2 | 11/2005 |
| WO | 2006/111772 A2 | 10/2006 |
| WO | 2006/116761 A2 | 11/2006 |
| WO | 2006/111772 A3 | 12/2006 |
| WO | 2005/102015 A3 | 4/2007 |
| WO | 2008/015257 A2 | 2/2008 |
| WO | 2008/015257 A3 | 4/2008 |
| WO | 2008/051428 A2 | 5/2008 |
| WO | 2008/051428 A3 | 7/2008 |
| WO | 2008/088835 A1 | 7/2008 |
| WO | 2009/026272 A1 | 2/2009 |
| WO | 2006/116761 A3 | 4/2009 |
| WO | 2009/070180 A1 | 6/2009 |
| WO | 2010/011699 A2 | 1/2010 |
| WO | 2010/011699 A3 | 5/2010 |

OTHER PUBLICATIONS

International Search Report and Written Opinion received for PCT Patent Application No. PCT/US2009/051324 mailed on Mar. 30, 2010, 10 pages.

International Preliminary Report on Patentability received for PCT Patent Application No. PCT/US2013/021052, mailed on Jul. 24, 2014, 9 pages.

International Search Report and Written Opinion received for PCT Patent Application No. PCT/US2013/021052, mailed on Jun. 10, 2013, 12 pages.

International Search Report and Written Opinion received for PCT Patent Application No. PCT/US2014/023788, mailed on Sep. 10, 2014, 16 pages.

Invitation to pay additional fees received for PCT Patent Application No. PCT/US2014/023788, mailed on Jul. 1, 2014, 2 pages.

Office Action received for Australian Patent Application No. 2009274131, mailed on May 6, 2014, 4 pages.

Office Action received for Canadian Patent Application No. 2,731,551, mailed on Nov. 12, 2014, 3 pages.

Decision to Grant received for Chinese Patent Application No. 200980136513.2, mailed on Dec. 2, 2014, 4 pages. (2 pages of English Translation and 2 pages of Official Copy).

Office Action received for Chinese Patent Application No. 200980136513.2, mailed on Jul. 28, 2014, 5 pages (2 pages of English Translation and 3 pages of Official Copy).

Office Action Received for Japanese Patent Application No. 2011-520148, mailed on Dec. 22, 2014, 6 pages (3 pages of English Translation and 3 pages of Official Copy).

Final Office Action received for U.S. Appl. No. 13/055,441, mailed on Aug. 23, 2013, 10 pages.

Non-Final Office Action received for U.S. Appl. No. 13/055,441, mailed on Feb. 12, 2013, 9 pages.

Notice of Allowance received for U.S. Appl. No. 13/055,441, mailed on Nov. 12, 2013, 11 pages.

Final Office Action received for U.S. Appl. No. 13/069,037, mailed on Jan. 29, 2014, 5 pages.

(56) References Cited

OTHER PUBLICATIONS

Non-Final Office Action received for U.S. Appl. No. 13/069,037, mailed on Jun. 20, 2014, 6 pages.
Notice of Allowance received for U.S. Appl. No. 13/069,037, mailed on Jan. 26, 2015, 7 pages.
Advisory Action received for U.S. Appl. No. 13/111,855, mailed on Jan. 29, 2014, 2 pages.
Final Office Action received for U.S. Appl. No. 13/111,855, mailed on Nov. 26, 2013, 9 pages.
Final Office Action received for U.S. Appl. No. 13/111,855, mailed on Oct. 6, 2014, 8 pages.
Non-Final Office Action received for U.S. Appl. No. 13/111,855, mailed on Jan. 4, 2013, 9 pages.
Non-Final Office Action received for U.S. Appl. No. 13/111,855, mailed on Mar. 28, 2014, 8 pages.
Notice of Allowance received for U.S. Appl. No. 13/111,855, mailed on Dec. 19, 2014, 7 pages.
Final Office Action received for U.S. Appl. No. 13/113,887, mailed on Dec. 16, 2013, 7 pages.
Final Office Action received for U.S. Appl. No. 13/113,887, mailed on Jun. 20, 2014, 7 pages.
Non-Final Office Action received for U.S. Appl. No. 13/113,887, mailed on Apr. 24, 2013, 6 pages.
Notice of Allowance received for U.S. Appl. No. 13/113,887, mailed on Aug. 29, 2014, 7 pages.
Non-Final Office Action received for U.S. Appl. No. 13/113,890, mailed on Aug. 19, 2014, 8 pages.
Final Office Action received for U.S. Appl. No. 13/158,232, mailed on Apr. 11, 2014, 12 pages.
Non Final Office Action received for U.S. Appl. No. 13/158,232, mailed on Oct. 21, 2014, 10 pages.
Non-Final Office Action received for U.S. Appl. No. 13/158,232, mailed on Nov. 8, 2013, 8 pages.
Office Action Received for Israeli Patent Application No. 230266, mailed on Apr. 2, 2015, 4 pages (2 pages of English Translation and 2 pages of Official Copy).
Advisory Action received for U.S. Appl. No. 13/113,890, mailed on Sep. 29, 2015, 2 pages.
Final Office Action received for U.S. Appl. No. 13/113,890, mailed on May 21, 2015, 9 pages.
Final Office Action received for U.S. Appl. No. 13/158,232, mailed on Apr. 10, 2015, 12 pages.
Notice of Allowance received for U.S. Appl. No. 13/158,232, mailed on Oct. 13, 2015, 7 pages.
Notice of Allowance received for Canadian Patent Application No. 2,731,551, mailed on Jun. 4, 2015, 1 page.
Notice of Acceptance received for Australian Patent Application No. 2009274131, mailed on May 25, 2015, 2 pages.
Notice Prior to Acceptance received for the Israeli Patent Application No. 230266, mailed on Aug. 10, 2015, 4 pages (2 pages of English Machine Translation and 2 pages of Official Copy).
Invitation to Pay Additional Fees received for PCT Patent Application No PCT/US2013/021052, mailed on Mar. 26, 2013, 3 pages.
International Preliminary Report on Patentability received for PCT Patent Application No. PCT/US2014/023788 mailed on Sep. 24, 2015, 14 pages.
Office Action Received for Japanese Patent Application No. 2011-520148, mailed on Dec. 22, 2014, 7 pages (4 pages of English Translation and 3 pages of Official Copy).

* cited by examiner

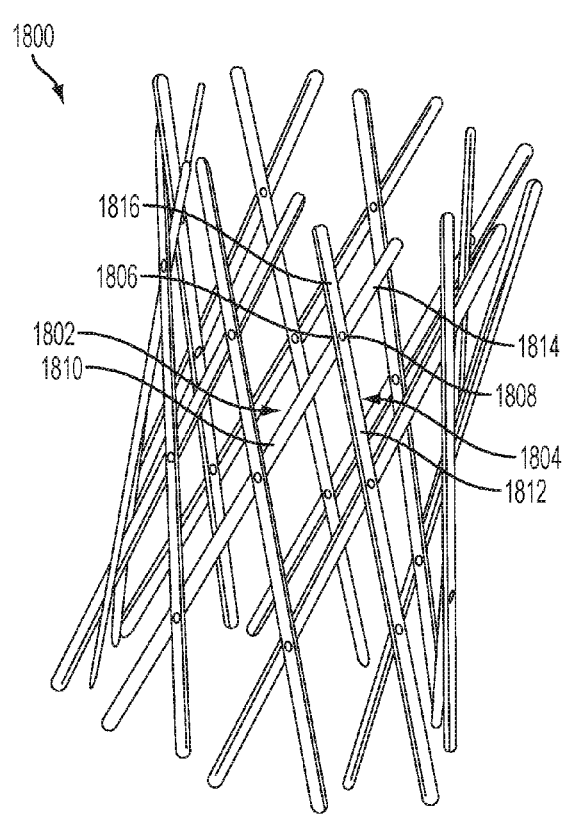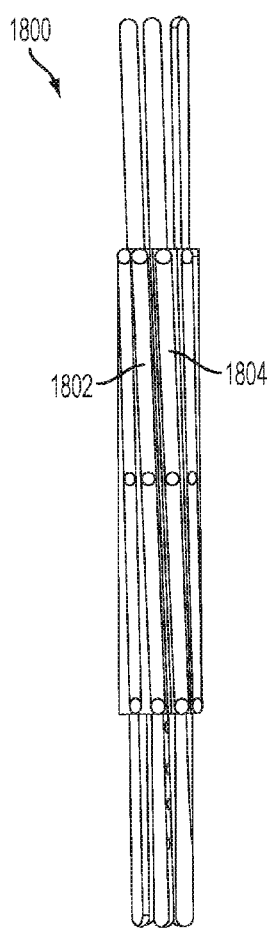
FIG. 18A
FIG. 18B

ARTICULATED COMMISSURE VALVE STENTS AND METHODS

CROSS-REFERENCE TO RELATED APPLICATIONS

This application claims priority to U.S. Provisional Application Ser. No. 61/780,670, filed Mar. 13, 2013, and titled "ARTICULATED COMMISSURE VALVE STENTS AND METHODS," the content of which is hereby incorporated in its entirety.

BACKGROUND

Endoluminal stents can be implanted in a vessel or tract of a patient to help maintain an open lumen. The stents can also be used as a frame to support a prosthetic device or to deliver a therapeutic agent. Stents can be implanted by either an open operative procedure or a closed operative procedure. When an option exists, the less invasive closed procedure is generally preferred because the stent can be guided through a body lumen, such as the femoral artery, to its desired location.

Closed procedures typically use one of two techniques. One closed procedure employs balloon catheterization where an expandable stent encloses an inflatable balloon. In this procedure, the stent is implanted by inflating the balloon, which causes the stent to expand. The actual positioning of the stent cannot be determined until after the balloon is deflated and, if there is a misplacement of the stent, the process cannot be reversed to reposition the stent.

The other closed procedure employs a compressed stent enclosed by a removable sheath. In this procedure, a stent made from a shape memory alloy, such as Nitinol, is held in a compressed state by a sheath. The stent is implanted by withdrawing the sheath, causing the stent to expand to its nominal shape. Again, if there is a misplacement of the stent, the process cannot be reversed to reposition the stent.

Positioning errors are particularly dangerous when the stent is used to support a cardiac valve. Serious complications and patient deaths have occurred due to malpositioning of the valve at the implant site in the body, using the available stent-mounted valves. Malpositioning of the valve has resulted in massive paravalvular leakage, device migration, and coronary artery obstruction. The majority of these complications were unavoidable, but detected at the time of the procedure. However, due to inability to reposition or retrieve the device, these problems were impossible to reverse or mitigate during the procedure.

SUMMARY

An endoluminal support structure or stent in accordance with certain embodiments of the invention solves certain deficiencies found in the prior art. In particular, the support structure can be repositioned within the body lumen or retrieved from the lumen.

A particular embodiment of the invention includes a support apparatus implantable within a biological lumen. The support apparatus can include a plurality of elongated strut members interlinked by a plurality of rotatable joints, wherein the rotatable joints can cooperate with the stent members to adjustably define a shaped structure between a compressed orientation and an expanded orientation.

More particularly, the shaped structure can be one of a cylindrical, a conical, or an hourglass shape. A rotatable joint can form a scissor mechanism with a first strut member and a second strut member. Furthermore, the strut members can be arranged as a series of linked scissor mechanisms. The apparatus can further include an actuation mechanism to urge the rotatable joints within a range of motion.

The apparatus can also include a prosthetic valve coupled to the shaped structure.

Another particular embodiment of the invention can include a medical stent implantable within a biological lumen. The medical stent can include a plurality of elongated strut members, including a first strut member and a second strut member, and a rotatable joint connecting the first strut member and the second strut member.

In particular, the rotatable joint can form a scissor mechanism with the first strut member and the second strut member. The rotatable joint can bisect the first strut member and the second strut member. The rotatable joint can interconnect a first end of the first strut member with a first end of the second strut member.

The plurality of strut members can be arranged as a series of linked scissor mechanisms. The strut members can also be non-linear. The strut members can be arranged to form one of a cylindrical, a conical, or an hourglass shape.

The stent can further include an adjustment mechanism to exerting a force to urge the strut members about the rotatable joint within a range of motion.

The stent can include a prosthetic valve coupled to the strut members.

Specific embodiments of the invention can include prosthetic valves that are rotatable or conventional.

A rotatable prosthetic valve can include a first structural member coupled to the strut members, a second structural member rotatable relative to the first structural member, and a plurality of pliable valve members connecting the first structural member with the second structural member such that rotation of the second structural member relative to the first structural member can urge the valve members between an open and a closed state. In particular, the rotation of the second structural member can be responsive to the natural flow of a biological fluid.

A conventional prosthetic valve can include a plurality of pliable valve leaflets having commissures at the intersection of two strut members. The prosthetic valve can further include a skirt material coupled to the strut members.

These structures can also be interconnected in various combinations.

A particular advantage of a support structure in accordance with embodiments of the invention is that it enables a prosthetic valve to be readily retrieved and repositioned in the body. If following deployment, the valve is malpositioned or deemed dysfunctional, the support structure allows the valve to be readily repositioned and re-deployed at a new implant site, or removed from the body entirely. This feature of the device can prevent serious complications and save lives by enabling the repair of mal-positioned devices in the body.

A particular embodiment of the invention comprises a biocompatible articulated support structure, comprising a tubular support body with a proximal opening, and a distal opening, with a lumen and a longitudinal axis between the proximal and distal openings, wherein the tubular body comprises a plurality of discrete struts coupled by a plurality of rotatable articulations, each articulation comprising an axis of rotation with a radial orientation, and wherein the plurality of rotatable articulations comprise a set of proximal rotatable articulations configured to reside in a proximal plane with the proximal opening, a set of distal rotatable articulations configured to reside in a distal plane with the distal opening, a first set of middle rotatable articulations, located between the proximal plane and the distal plane, and at least one commissural point articulation distal to the distal plane, and wherein the plurality of discrete inner struts, the plurality of discrete outer struts and the articulations therebetween intrinsically provide a self-expansion force. The support structure may have at least one commissural point articulation is linked by at least two of the plurality of discrete struts to two commissural base articulations. The two commissural base articulations may be located at or proximal to the distal plane. When the tubular support body is in an expanded state, the first set of middle rotatable articulations, may be located closer to the proximal plane than the distal plane. The plurality of discrete struts may comprise a plurality of inner struts, a plurality of outer struts, and at least a pair of an inner commissural strut and an outer commissural strut. Each of the plurality of inner struts may be coupled to two of the plurality of outer struts, and either a third strut from the plurality of outer struts or one of the at least one outer commissural struts. Each of the plurality of outer struts is coupled to two of the plurality of inner struts, and either a third strut from the plurality of inner struts or one of the at least one inner commissural struts. When the tubular support body is in an expanded state, the average angle of the at least one commissural point articulation may be less than the average angle of the set of distal rotatable articulations. Each of the plurality of inner struts that is not coupled to a commissural strut and each of the plurality of outer struts that is not coupled to a commissural strut has a first length, and wherein each of the plurality of inner struts that is coupled to a commissural strut and each of the plurality of outer struts coupled to a commissural strut has a second length, and the second length may be different from the first length, or the second length may shorter than the first length. When the tubular support body is in the expanded state, a distance between the at least one commissural point articulation and the distal plane may be at least 20% of a longitudinal distance between the proximal and distal planes. The support structure may further comprise an expandable hourglass securing body comprising a proximal opening, and a distal opening, with a lumen and a longitudinal axis between the proximal and distal openings, and wherein the tubular support body may be configured to reside within the lumen of the expandable hourglass securing body. The expandable hourglass structure may comprise a distal tapered section, a proximal tapered section, and a narrow section therebetween, and wherein the tubular support body may be secured to the narrow section. The expandable hourglass securing body may comprise a plurality of discrete non-linear struts interconnected by rotatable articulations with a rotation of axis in a radial orientation. The support structure may further comprise at least one locking ring secured to at least one of the distal tapered section and the proximal tapered section. The at least one locking ring may be located within the lumen of the expandable securing body. The at least one locking ring may comprise a plurality of inner struts and a plurality of outer struts interconnected by rotatable articulations with a rotation of axis in a radial orientation.

A particular embodiment of the invention comprises a biocompatible articulated support structure, comprising a tubular structure comprising a central lumen, a central axis, a plurality of discrete inner struts, and a plurality of discrete outer struts, wherein each of the plurality of discrete inner struts and the plurality of discrete outer struts comprises first end, a second end, and a net length therebetween, and wherein each of the plurality of discrete inner struts comprises articulations with at least two different discrete outer struts of the plurality of discrete outer struts, and wherein each of the plurality of discrete outer struts comprises articulations with at least two different discrete inner struts of the plurality of discrete inner struts, and wherein no discrete inner strut of the plurality of discrete inner struts comprises articulations with any other discrete inner strut of the plurality of discrete inner struts, and wherein no discrete outer strut of the plurality of discrete outer struts comprises articulations with any other discrete outer strut of the plurality of discrete outer struts, and wherein at least one strut from either the plurality of discrete inner struts or the plurality of discrete outer struts comprises first end, a second end, and a net length therebetween, and wherein the first end of the at least one strut is spaced apart from a closest articulation by about at least 25% of the net length of that strut. The first end of each of the plurality of discrete outer struts may be spaced apart from a closest articulation by about at least 25% of its net length. The second end of each of the plurality of discrete outer struts may be spaced apart from a closest articulation by about at least 25% of its net length. The first end of each of the plurality of discrete inner struts may be spaced apart from a closest articulation by about at least 25% of its net length. The second end of each of the plurality of discrete inner struts may be spaced apart from a closest articulation by about at least 25% of its net length.

A particular embodiment of the invention comprises a biocompatible articulated support structure, comprising a tubular structure comprising a central lumen, a central axis, a plurality of discrete inner struts, a plurality of discrete outer struts, and at least one bow strut, wherein each of the plurality of discrete inner struts, the plurality of discrete outer struts and the at least one bow strut comprises first end, a second end, and a net length therebetween, and wherein each of the plurality of discrete inner struts comprises articulations with at least two different discrete outer struts of the plurality of discrete outer struts, and wherein each of the plurality of discrete outer struts comprises articulations with at least two different discrete inner struts of the plurality of discrete inner struts, and wherein no discrete inner strut of the plurality of discrete inner struts comprises articulations with any other discrete inner strut of the plurality of discrete inner struts, and wherein no discrete outer strut of the plurality of discrete outer struts comprises articulations with any other discrete outer strut of the plurality of discrete outer struts, and wherein the at least one bow strut comprises a first articulation with a first strut selected from either the plurality of discrete inner struts and the plurality of discrete outer struts, and a second articulation with a second strut selected from the same plurality of discrete inner struts or plurality of discrete outer struts. The first strut and the second struts may be directly adjacent struts. The at least one bow strut may be an inner bow strut wherein the first and second struts may be selected from the plurality of discrete inner struts. The at least one bow strut may be a plurality of inner bow struts. The at least one bow strut may be an outer bow strut wherein the first and second struts may be selected from the plurality of discrete outer struts. The at least one bow strut may be a plurality of outer bow struts. The support structure may further comprise a secondary structure located between the plurality of outer bow struts and the plurality of discrete outer struts. The secondary structure may be a circumferential tubular balloon.

A particular embodiment of the invention comprises a biocompatible articulated structure, comprising a tubular structure comprising a central lumen, a central axis, a plurality of discrete inner struts, a plurality of discrete outer struts, and at least two radial struts, wherein each of the plurality of discrete inner struts and the plurality of discrete outer struts comprises first end, a second end, and a net length therebetween, and wherein each of the at least two radial struts comprises an outer end, an inner end and a net length therebetween, wherein each outer end is coupled to at least one strut selected from the plurality of discrete inner struts and the plurality of discrete outer struts, and wherein the inner ends of the at least two radial struts are coupled together, and wherein each of the plurality of discrete inner struts comprises articulations with at least three different discrete outer struts of the plurality of discrete outer struts, and wherein each of the plurality of discrete outer struts comprises articulations with at least three different discrete inner struts of the plurality of discrete inner struts, and wherein no discrete inner strut of the plurality of discrete inner struts comprises articulations with any other discrete inner strut of the plurality of discrete inner struts, and wherein no discrete outer strut of the plurality of discrete outer struts comprises articulations with any other discrete outer strut of the plurality of discrete outer struts. The inner ends of the at least two radial struts may be coupled at centrally aligned coupling apertures. The inner ends of the at least two radial struts may be coupled at coupling apertures using a loop coupling structure. The at least two radial struts may comprise a first plurality of radial struts and a second plurality of radial struts, wherein each outer end of the first plurality of radial struts may be coupled to the first ends of at least one strut selected from the plurality of discrete inner struts and the plurality of discrete outer struts, and wherein each outer end of the second plurality of radial struts may be coupled to the second ends of at least one strut selected from the plurality of discrete inner struts and the plurality of discrete outer struts. The inner ends of the first plurality of radial struts may be coupled together and the inner ends of the second plurality of radial struts may be coupled together. The inner ends of the first plurality of radial struts may be attached to a first deployment structure and the inner ends of the second plurality of radial struts may be attached to a second deployment structure. The inner ends of the first plurality of radial struts may be attached to a first region of a deployment structure and the inner ends of the second plurality of radial struts may be attached to a second region of the deployment structure. The deployment structure may be a screw drive mechanism. The structure may further comprise a delivery catheter permanently attached to the tubular structure. The delivery catheter may comprise a plurality of wires electrically coupled to the tubular structure.

A particular embodiment of the invention comprises a biocompatible articulated structure, comprising a tubular structure comprising a central lumen, a central axis, a plurality of discrete inner struts, and a plurality of discrete outer struts, wherein each of the plurality of discrete inner struts and the plurality of discrete outer struts comprises first end, a second end, and a net length therebetween, wherein each of the plurality of discrete inner struts comprises articulations with at least four different discrete outer struts of the plurality of discrete outer struts, and wherein each of the plurality of discrete outer struts comprises articulations with at least four different discrete inner struts of the plurality of discrete inner struts, and wherein no discrete inner strut of the plurality of discrete inner struts comprises articulations with any other discrete inner strut of the plurality of discrete inner struts, and wherein no discrete outer strut of the plurality of discrete outer struts comprises articulations with any other discrete outer strut of the plurality of discrete outer struts, and wherein at least one strut from either the plurality of discrete inner struts or the plurality of discrete outer struts comprises first end, a second end, and a net length therebetween; and wherein the plurality of discrete inner struts, the plurality of discrete outer struts and the articulations therebetween intrinsically provide a self-expansion force. The tubular structure may comprise an intrinsically stable non-expanding collapsed state. The plurality of discrete inner struts and the plurality of discrete outer struts may be configured to form a first set of cells aligned along a first perimeter of the tubular structure and a second set of cells directly adjacent to the first set of cells and aligned along a second perimeter of the tubular structure. The plurality of discrete inner struts comprises articulations with at least five different discrete outer struts of the plurality of discrete outer struts, wherein each of the plurality of discrete outer struts may comprise articulations with at least five different discrete inner struts of the plurality of discrete inner struts, and wherein the plurality of discrete inner struts and the plurality of discrete outer struts may be further configured to form a third set of cells directly adjacent to the second set of cells and aligned along a third perimeter of the tubular structure.

A particular embodiment of the invention comprises a biocompatible articulated structure comprising a tubular structure comprising a central lumen, a central axis, a plurality of discrete inner struts, a plurality of discrete outer struts, and a plurality of discrete commissure struts, wherein each of the plurality of discrete inner struts and the plurality of discrete outer struts comprises a first end, a second end, and a net length therebetween, and wherein each of the plurality of discrete inner struts comprises articulations with at least three different discrete outer or commissure struts of the pluralities of discrete outer and commissure struts, and wherein each of the plurality of discrete outer struts comprises articulations with at least three different discrete inner or commissure struts of the pluralities of discrete inner and commissure struts, and wherein each of the plurality of discrete commissure struts comprises articulations with one discrete outer or inner strut of the pluralities of discrete outer and inner struts and with one other discrete commissure strut of the plurality of discrete commissure struts, and wherein no discrete inner strut of the plurality of inner struts comprises articulations with any other discrete inner strut of the plurality of discrete inner struts; and wherein no discrete outer strut of the plurality of discrete outer struts comprises articulations with any other discrete outer strut of the plurality of discrete outer struts.

A particular embodiment of the invention comprises a biocompatible articulated support structure, comprising an hourglass structure comprising a central lumen, a central axis, a plurality of discrete inner struts, and a plurality of discrete outer struts, wherein each of the plurality of discrete inner struts and the plurality of discrete outer struts comprises a first end, a second end, and a net length therebetween; and wherein each of the plurality of discrete inner struts and the plurality of discrete outer struts has a helical configuration with the helical axis aligned with the central axis of the structure; and wherein each of the plurality of discrete inner struts comprises two articulations with a single discrete outer strut of the plurality of discrete outer struts, and at least one articulation with a different discrete outer strut of the plurality of discrete outer struts; and wherein each of the plurality of discrete outer struts comprises two articulations with a single discrete inner strut of the plurality of discrete inner struts, and at least one articulation with a different discrete inner strut of the plurality of discrete inner struts; and wherein no discrete inner strut of the plurality of inner struts comprises articulations with any other discrete inner strut of the plurality of discrete inner struts; and wherein no discrete outer strut of the plurality of discrete outer struts comprises articulations with any other discrete outer strut of the plurality of discrete outer struts; and wherein the diameter of the support structure at either end of the central axis is greater than the diameter of the support structure at the midpoint of the central axis.

A particular embodiment of the invention comprises a biocompatible articulated support structure, comprising a tubular structure comprising a central lumen, a central axis, a plurality of discrete inner struts, and a plurality of discrete outer struts, wherein each of the plurality of discrete inner struts and the plurality of discrete outer struts comprises a first end, a second end, and a net length therebetween, wherein each of the plurality of discrete inner struts comprises articulations with at least three different discrete outer struts of the plurality of discrete outer struts, and wherein each of the plurality of discrete outer struts comprises articulations with at least three different discrete inner struts of the plurality of discrete inner struts, and wherein no discrete inner strut of the plurality of inner struts comprises articulations with any other discrete inner strut of the plurality of discrete inner struts, and wherein no discrete outer strut of the plurality of discrete outer struts comprises articulations with any other discrete outer strut of the plurality of discrete outer struts, and wherein the support structure is in an unstressed state when in a fully expanded configuration.

A particular embodiment of the invention comprises a biocompatible articulated support structure, comprising a valve structure, comprising a tubular structure comprising a central lumen, a central axis, a plurality of discrete inner struts, a plurality of discrete outer struts, and a plurality of discrete commissure struts, wherein each of the plurality of discrete inner struts and the plurality of discrete outer struts comprises a first end, a second end, and a net length therebetween, wherein each of the plurality of discrete inner struts comprises articulations with at least three different discrete outer or commissure struts of the pluralities of discrete outer and commissure struts, and wherein each of the plurality of discrete outer struts comprises articulations with at least three different discrete inner or commissure struts of the pluralities of discrete inner and commissure struts, and wherein each of the plurality of discrete commissure struts comprises articulations with one discrete outer or inner strut of the pluralities of discrete outer and inner struts and with one other discrete commissure strut of the plurality of discrete commissure struts, and wherein no discrete inner strut of the plurality of inner struts comprises articulations with any other discrete inner strut of the plurality of discrete inner struts, and wherein no discrete outer strut of the plurality of discrete outer struts comprises articulations with any other discrete outer strut of the plurality of discrete outer struts, and a fixation structure, comprising an hourglass structure comprising a central lumen, a central axis, a plurality of discrete inner struts, and a plurality of discrete outer struts, wherein each of the plurality of discrete inner struts and the plurality of discrete outer struts comprises a first end, a second end, and a net length therebetween, and wherein each of the plurality of discrete inner struts and the plurality of discrete outer struts has a helical configuration with the helical axis aligned with the central axis of the structure, and wherein each of the plurality of discrete inner struts comprises two articulations with a single discrete outer strut of the plurality of discrete outer struts, and at least one articulation with a different discrete outer strut of the plurality of discrete outer struts, and wherein each of the plurality of discrete outer struts comprises two articulations with a single discrete inner strut of the plurality of discrete inner struts, and at least one articulation with a different discrete inner strut of the plurality of discrete inner struts, and wherein no discrete inner strut of the plurality of inner struts comprises articulations with any other discrete inner strut of the plurality of discrete inner struts, and wherein no discrete outer strut of the plurality of discrete outer struts comprises articulations with any other discrete outer strut of the plurality of discrete outer struts, and wherein the diameter of the support structure at either end of the central axis is greater than the diameter of the support structure at the midpoint of the central axis, at least two locking ring structures, comprising a tubular structure comprising a central lumen, a central axis, a plurality of discrete inner struts, a plurality of discrete outer struts, wherein each of the plurality of discrete inner struts and the plurality of discrete outer struts comprises a first end, a second end, and a net length therebetween, wherein each of the plurality of discrete inner struts comprises articulations with at least three different discrete outer struts of the plurality of discrete outer struts, and wherein each of the plurality of discrete outer struts comprises articulations with at least three different discrete inner struts of the plurality of discrete inner struts, and wherein no discrete inner strut of the plurality of inner struts comprises articulations with any other discrete inner strut of the plurality of discrete inner struts, and wherein no discrete outer strut of the plurality of discrete outer struts comprises articulations with any other discrete outer strut of the plurality of discrete outer struts, and wherein the support structure is in an unstressed state when in a fully expanded configuration, and wherein the central axes of the valve structure, fixation structure, and two locking ring structures are aligned, and wherein the valve structure is attached to at least one point to the fixation structure, and wherein each of the two locking ring structures is attached to at least one point to the fixation structure.

A particular embodiment of the invention comprises a biocompatible support structure delivery system, comprising an expandable support structure having proximal and distal ends, at least one ring attached to the proximal end of the support structure, at least one ring attached to the distal end of the support structure, wherein the at least one rings are attached to the support structure by loops, such that the rings can rotate freely within the loops, and wherein the rings are configured to attach to a control catheter assembly.

A particular embodiment of the invention comprises a method for implanting a biocompatible support structure, wherein the biocompatible support structure comprises an expandable support structure having proximal and distal ends, at least one ring attached to the proximal end of the support structure, and at least one ring attached to the distal end of the support structure, and wherein the rings are configured to attach to a control catheter assembly, comprising connecting the at least one ring attached to the proximal end of the support structure to the control catheter assembly, connecting the at least one ring attached to the distal end of the support structure to the control catheter assembly, using the control catheter assembly to move the distal end of the support structure toward the proximal end of the support structure, wherein moving the distal end of the support structure toward the proximal end of the support structure causes the support structure to expand radially, and detaching the at least one ring attached to the proximal end of the support structure and the at least one ring attached to the distal end of the support structure from the control catheter assembly to release the support structure.

BRIEF DESCRIPTION OF THE DRAWINGS

The foregoing and other objects, features and advantages of the invention will be apparent from the following more particular description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 18A and 18B are perspective and side elevational views, respectively, of one embodiment of an articulated support structure comprising strut extension segments.

DETAILED DESCRIPTION

Particular embodiments of the invention include endoluminal support structures (stents) and prosthetic valves.

Figure 1:
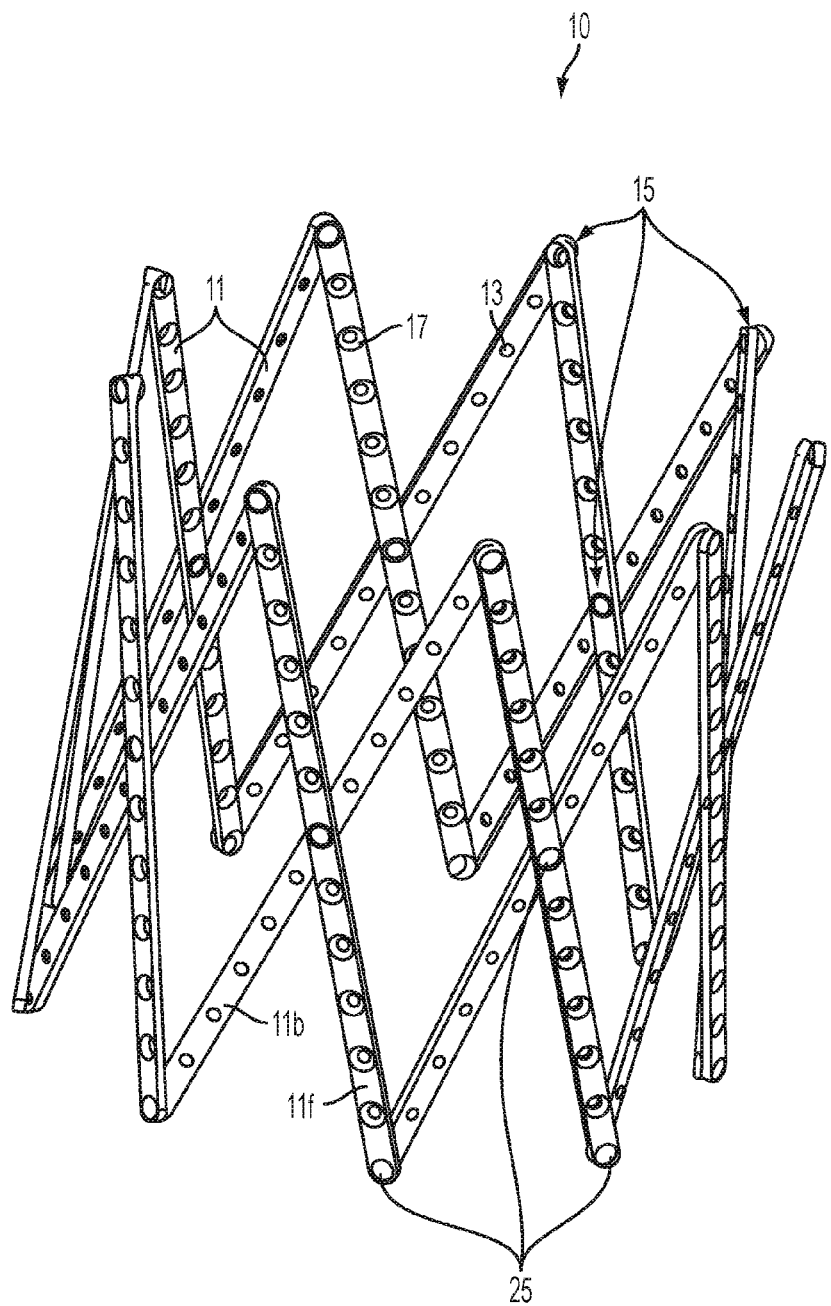
FIG. 1 is a perspective view of a particular endoluminal support structure.

FIG. 1 is a perspective view of a particular endoluminal support structure. As shown, the support structure 10 is a medical stent that includes a plurality of longitudinal strut members 11 interconnected by a plurality of rotatable joints 15. In particular, the swivel joints 15 may allow the interconnected strut members 11 to rotate relative to each other. The rotatable joints may be able to be rotated about an axis of rotation, and/or may be swivelable. As shown, there are eighteen struts 11.

The strut members 11 may be fabricated from a rigid or semi-rigid biocompatible material, such as plastics or other polymers and metal alloys, including stainless steel, tantalum, titanium, nickel-titanium (e.g. Nitinol), and cobalt-chromium (e.g. ELGILOY). The dimensions of each strut can be chosen in accordance with its desired use. In a particular embodiment, each strut member may be made from stainless steel, which is about 0.001-0.100 inch thick. More particularly, each strut can be about 0.01 inch thick 300 series stainless steel. In another embodiment, each strut member can be made from cobalt-chromium (e.g. ELGILOY). While all struts 11 are shown as being of uniform thickness, the thickness of a strut can vary across a strut, such as a gradual increase or decrease in thickness along the length of a strut. Furthermore, individual struts can differ in thickness from other individual struts in the same support structure. In a particular embodiment, each strut member may be about 0.01-0.25 inches wide and about 0.25-3 inches long. More particularly, each strut can be about 0.06 inches wide and about 0.5 inches long. As shown, each strut member 11 is bar shaped and has a front surface 11f and a back surface 11b. The strut members can however be of different geometries. For example, instead of a uniform width, a strut can vary in width along its length. Furthermore, an individual strut can have a different width than another strut in the same support structure. Similarly, the strut lengths can vary from strut to strut within the same support structure. The particular dimensions can be chosen based on the implant site.

Furthermore, the struts can be non-flat structures. In particular, the struts can include a curvature, such as in a concave or convex manner in relationship to the inner diameter of the stent structure. The struts can also be twisted. The nonflatness or flatness of the struts can be a property of the material from which they are constructed. For example, the struts can exhibit shape-memory or heat-responsive changes in shape to the struts during various states. Such states can be defined by the stent in the compressed or expanded configuration.

Furthermore, the strut members 11 can have a smooth or rough surface texture. In particular, a pitted surface can provide tensile strength to the struts. In addition, roughness or pitting can provide additional friction to help secure the support structure at the implant site and encourage irregular encapsulation of the support structure 10 by tissue growth to further stabilize the support structure 10 at the implant site over time.

In certain instances, the stent could be comprised of struts that are multiple members stacked upon one another. Within the same stent, some struts could include elongated members stacked upon one another in a multi-ply configuration, and other struts could be one-ply, composed of single-thickness members. Within a single strut, there can be areas of one-ply and multi-ply layering of the members.

Each strut member 11 may also include a plurality of orifices 13 spaced along the length of the strut member 11. On the front surface 11f, the orifices may be countersunk 17 to receive the head of a fastener. In a particular embodiment, there are thirteen equally spaced orifices 13 along the length of each strut member 11, but more or less orifices can be used. The orifices 13 are shown as being of uniform diameter and uniform spacing along the strut member 11, but neither is required.

The strut members 11 can be arranged as a chain of four-bar linkages. The strut members 11 may be interconnected by pivot fasteners 25, such as rivets or capped pin, extending through aligned orifices 13, which may or may not be configured to permit rotating or tilting movement of the strut. It should be understood that other rotatable fasteners 25 can be employed such as screws, bolts, ball-in-socket structures, nails, or eyelets, and that the fasteners can be integrally formed in the struts 11 such as a peened semi-sphere interacting with an indentation or orifice, or a male-female coupling. In addition to receiving a fastener, the orifices 13 also provide an additional pathway for tissue growth-over to stabilize and encapsulate the support structure 10 over time.

Figure 2:
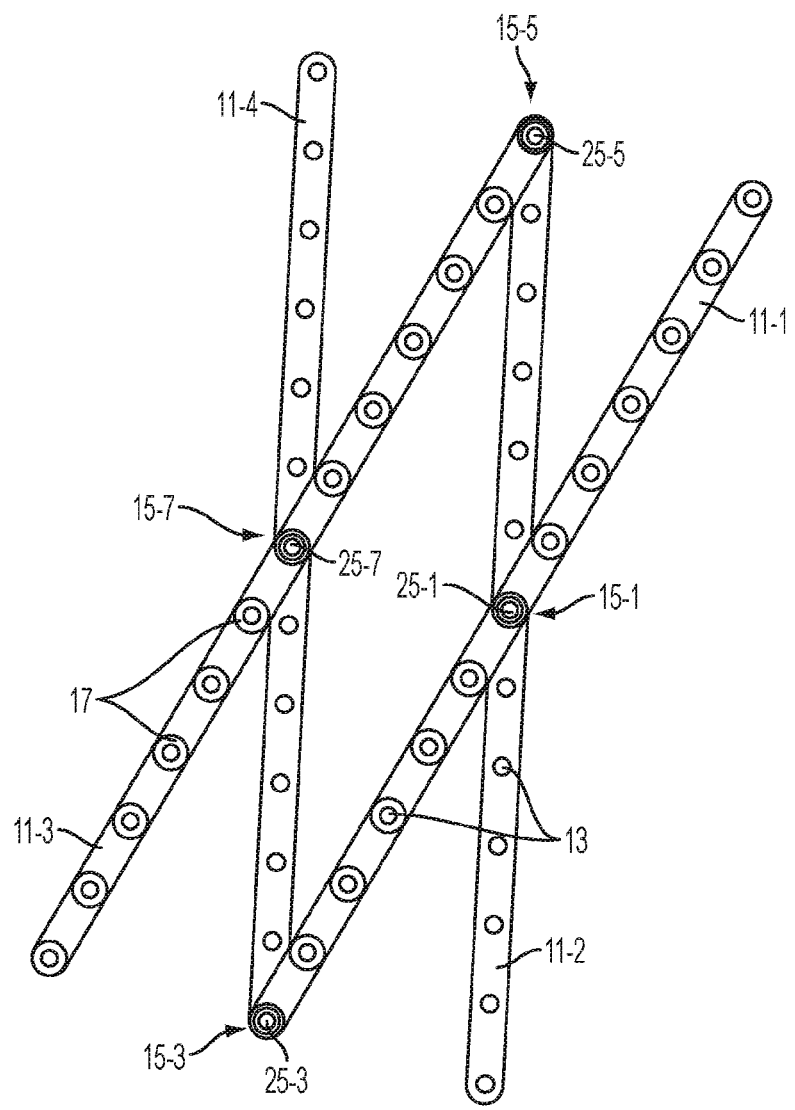
FIG. 2 is a perspective view of a four strut section of the stent of FIG. 1.

FIG. 2 is a perspective view of a four strut section of the stent of FIG. 1. As shown, two outer strut members 11-1, 11-3 overlap two inner strut members 11-2, 11-4, with their back surfaces in communication with each other.

In particular, the first strut member 11-1 may be rotatably connected to the second strut member 11-2 by a middle rotatable joint 15-1 using a rivet 25-1, which utilizes orifices 13 that bisect the strut members 11-1, 11-2. Similarly, the third strut member 11-3 may be rotatably connected to bisect the fourth strut member 11-4 by a middle rotatable joint 15-7 using a rivet 25-7. It should be understood that the middle rotatable joints 15-1, 15-7 can function as a scissor joint in a scissor linkage or mechanism. As shown, the resulting scissor arms are of equal length. It should also be understood that the middle joint 15-1, 15-7 need not bisect the joined strut members, but can instead utilize orifices 13 offset from the longitudinal centers of the strut members resulting in unequal scissor arm lengths.

In addition to the middle scissor joint 15-1, the second strut member 11-2 is rotatably connected to the third strut member 11-3 by a distal anchor rotatable joint 15-5, located near the distal ends of the strut members 11-2, 11-3. Similarly, the first strut member 11-1 is rotatably connected to the fourth strut member 11-4 by a proximal anchor rotatable joint 15-3, located near the proximal ends of the strut members 11-1, 11-4. To reduce stresses on the anchor rivets 25-3, 25-5, the distal and proximal ends of the struts 11 can be curved or twisted to provide a flush interface between the joined struts. As a result of these rotatable connections, the linkage can be reversibly expanded and compressed. When the linkage is laterally compressed, the two strut members 11-4 and 11-2 move to be directly adjacent to each other, and the two strut members 11-3 and 11-1 move to be directly adjacent to each other, such that center diamond-shaped opening is substantially closed. When the linkage is laterally expanded, the center diamond-shaped opening is widened.

Figure 30:
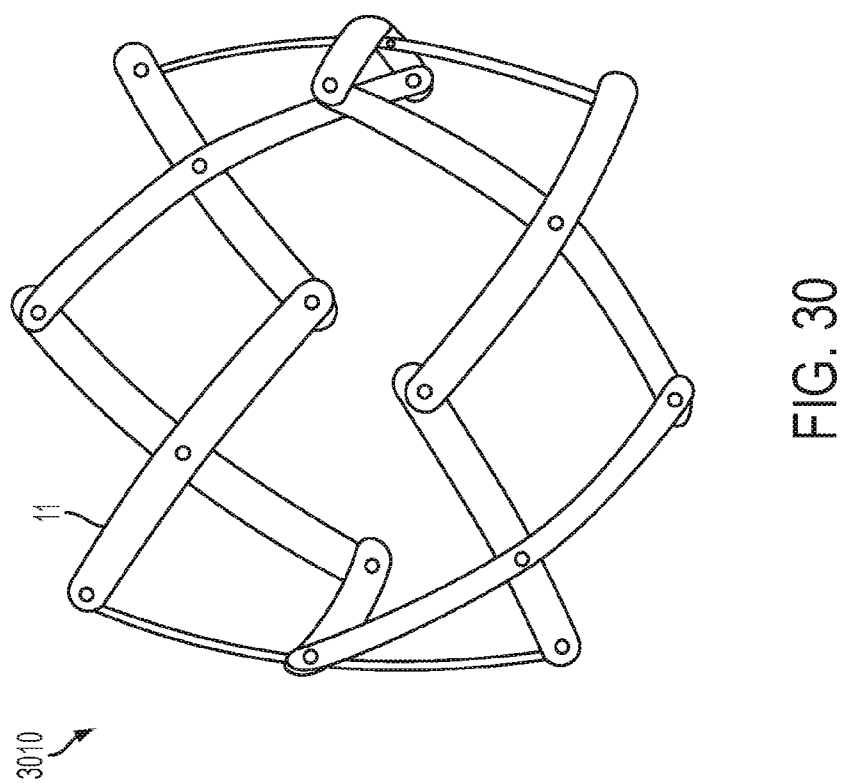
FIG. 30 illustrates a perspective view of a particular endoluminal support structure.

As can be seen, the support structure 10 (FIG. 1) may be fabricated by linking together a serial chain of scissor mechanisms. The chain may then be wrapped to join the last scissor mechanism with the first scissor mechanism in the chain. By actuating the linkage the links can be opened or closed, which results in expanding or compressing the stent 10 (FIG. 1). FIG. 1 shows a serial chain of scissor mechanisms such that there are eighteen struts 11, but other numbers of struts 11 can be used. FIG. 30, for example, shows a support structure 3010 with a serial chain of scissor mechanisms having twelve struts 11. As shown in FIG. 30, the struts 11 need not have orifices 13. In other variations, support structures having twelve struts 11 as in FIG. 30 may have orifices. This variation of support structure 3010 having twelve struts with orifices is shown as part of the combination structure in FIGS. 31A-I. FIG. 30 also shows struts 11 having a curvature, as described above. Support structure 3010, or support structures having other numbers or configurations of struts, can be reversibly expanded, reversibly compressed, fully expanded to form a ring, implanted, used with an actuator mechanism and control catheter assembly, and/or used to support a prosthetic valve in the same manner as support structure 10, described in detail below.

Returning to FIG. 1, by utilizing the rotatable joints 15, the diameter of the stent can be compressed for insertion through a biological lumen, such as an artery, to a selected position. The stent can then be expanded to secure the stent at the selected location within the lumen. Furthermore, after being expanded, the stent can be recompressed for removal from the body or for repositioning within the lumen.

Figure 3:
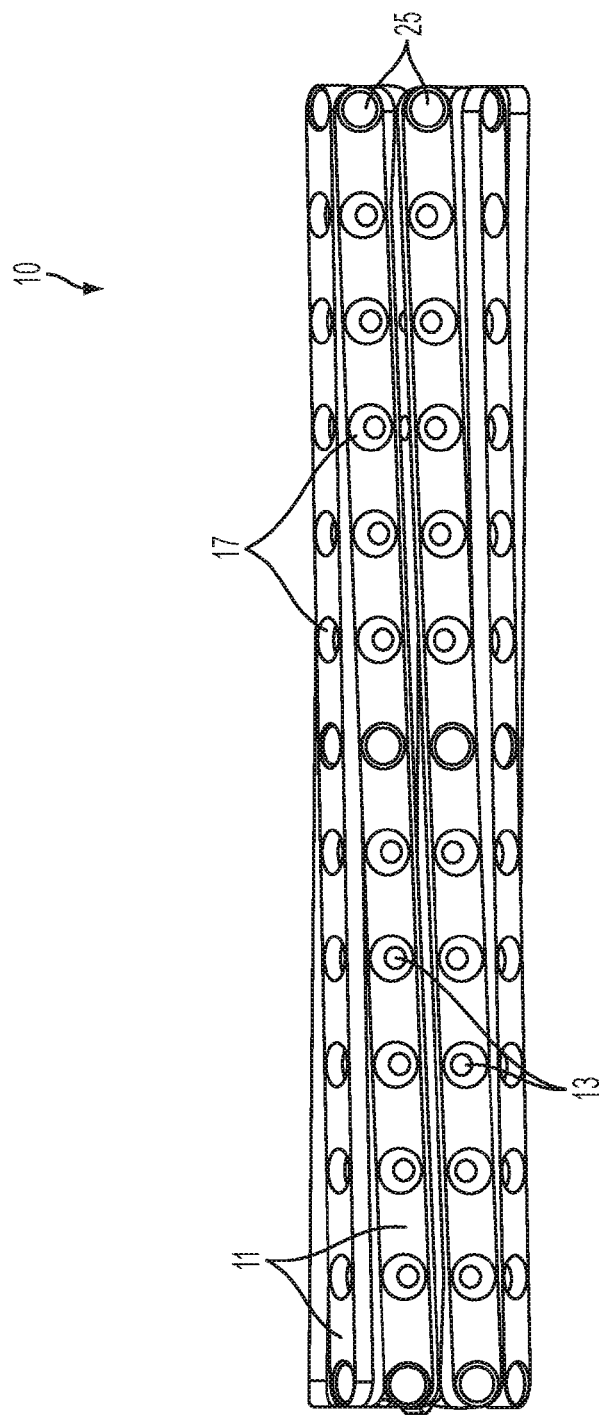
FIG. 3 is a perspective view of a compressed support structure of FIG. 1.

FIG. 3 is a perspective view of a compressed support structure of FIG. 1. When compressed, the stent 10 is at its maximum length and minimum diameter. The maximum length may be limited by the length of the strut members, which in a particular embodiment may be 15 mm. The minimum diameter may be limited by the width of the strut members, which in a particular embodiment may be about 0.052 inch. In compressed as shown in FIG. 3, the support structure is highly compact. However, the support structure may retain an open lumen through it while in the compressed state.

Figure 4:
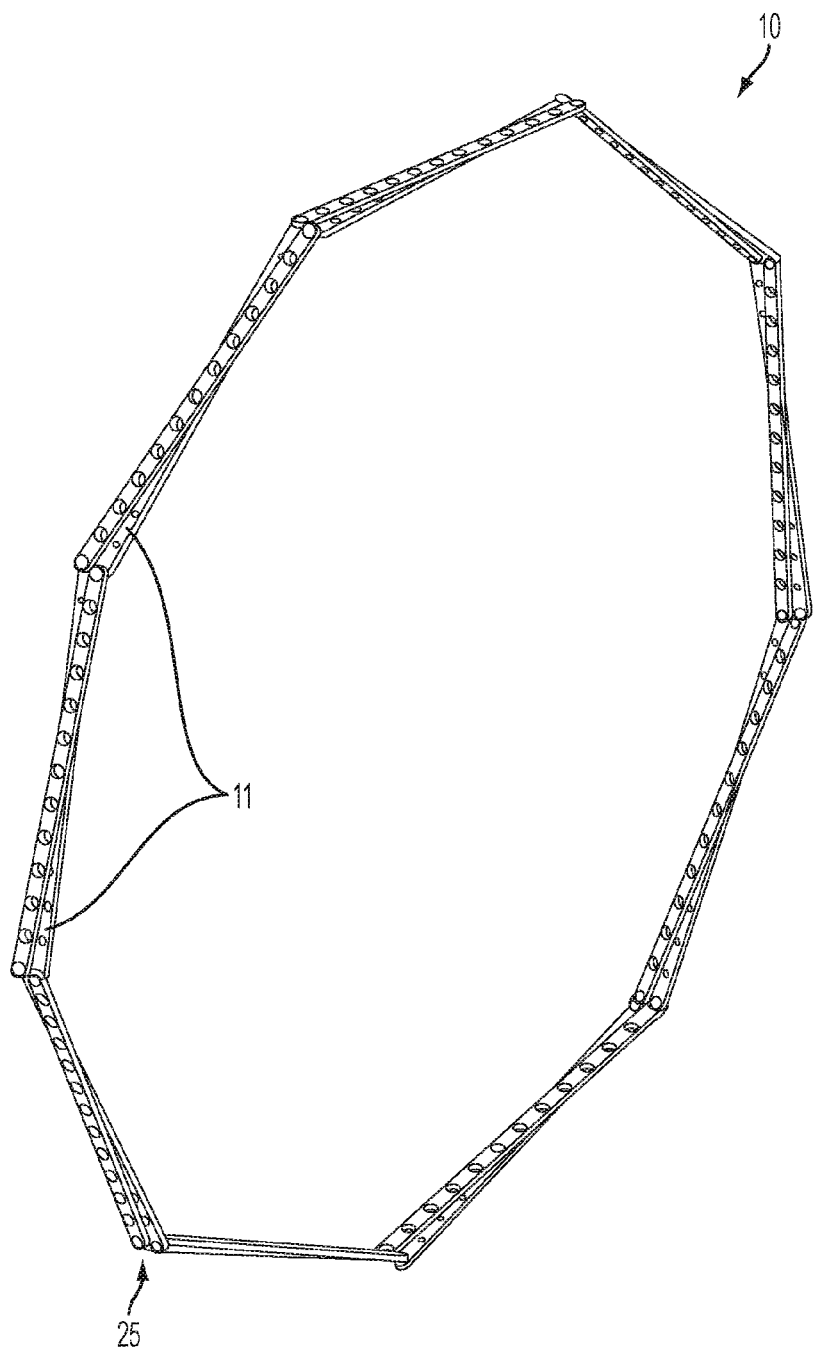
FIG. 4 is a perspective view of the support structure of FIG. 1 in a fully expanded state.

FIG. 4 is a perspective view of the support structure of FIG. 1 in a fully expanded state. As shown, the fully expanded support structure 10 forms a ring. Once in a fully expanded state, support structure 10 may enter a locked state such that radial inward pressure does not cause the support structure to re-compress and the support structure 10 is in an unstressed state. The ring formed can be used as an annuloplasty ring. In particular, if one end of the stent circumference is attached to tissue, the compression of the stent may enable the tissue to cinch. Because the stent may have the ability to have an incremental and reversible compression or expansion, the device could be used to provide an individualized cinching of the tissue to increase the competency of a heart valve. This could be a useful treatment for mitral valve diseases, such as mitral regurgitation or mitral valve prolapse.

While the support structure 10 may be able to be implanted in a patient during an open operative procedure, a closed procedure may also be desirable. As such, the support structure 10 may include an actuation mechanism to allow a surgeon to expand or compress the support structure from a location remote from the implant site. Due to the properties of a scissor linkage wrapped into a cylinder (FIG. 1), actuation mechanisms can exert force to expand the stent diameter by either increasing the distance between neighboring scissor joints, and decreasing the distance between the anchor joints.

Figure 5:
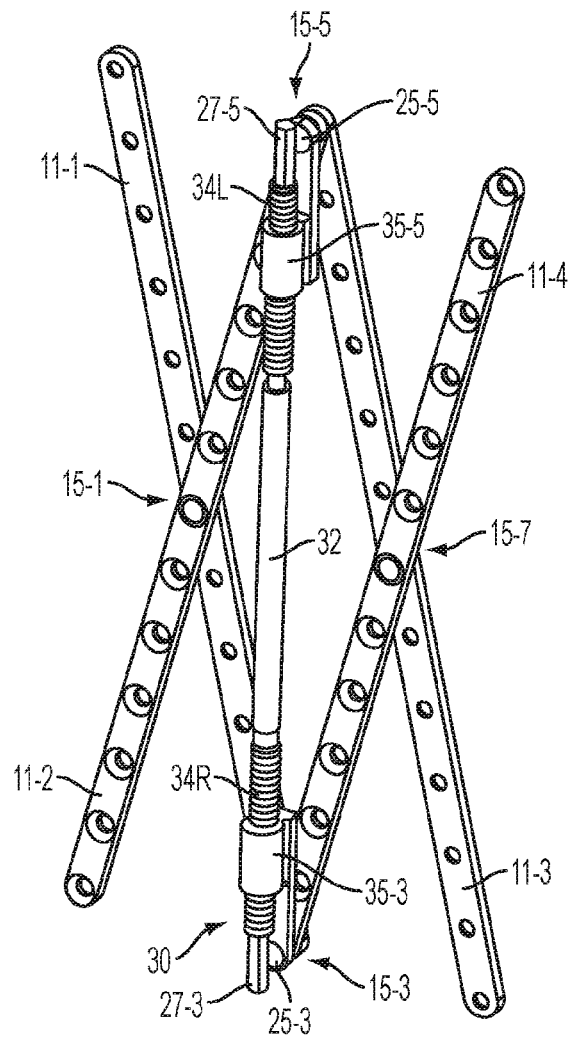
FIG. 5 is a perspective view of the support structure of FIG. 2 having a particular actuator mechanism.

FIG. 5 is a perspective view of the support structure of FIG. 2 having a particular actuator mechanism. As shown, the actuator mechanism 30 includes a dual-threaded rod 32 positioned on the inside of the support structure 10 (FIG. 1). It should be understood, however, that the actuator mechanism 30 can instead be positioned on the outside of the support structure 10. Whether positioned on the inside or outside, the actuator mechanism 30 may operate in the same way. The rod may include right-hand threads 34R on its proximal end and left-hand threads 34L on its distal end. The rod 32 may be mounted the anchor points 15-3, 15-5 using a pair of threaded low-profile support mounts 35-3, 35-5. Each end of the rod 32 may be terminated by a hex head 37-3, 37-5 for receiving a hex driver (not shown). As should be understood, rotating the rod 32 in one direction may urge the anchor points 25-3, 25-5 outwardly to compress the linkages while rotating the rod 32 in the opposite direction may urge the anchor points 25-3, 25-5 inwardly to expand the linkages.

Figure 6:
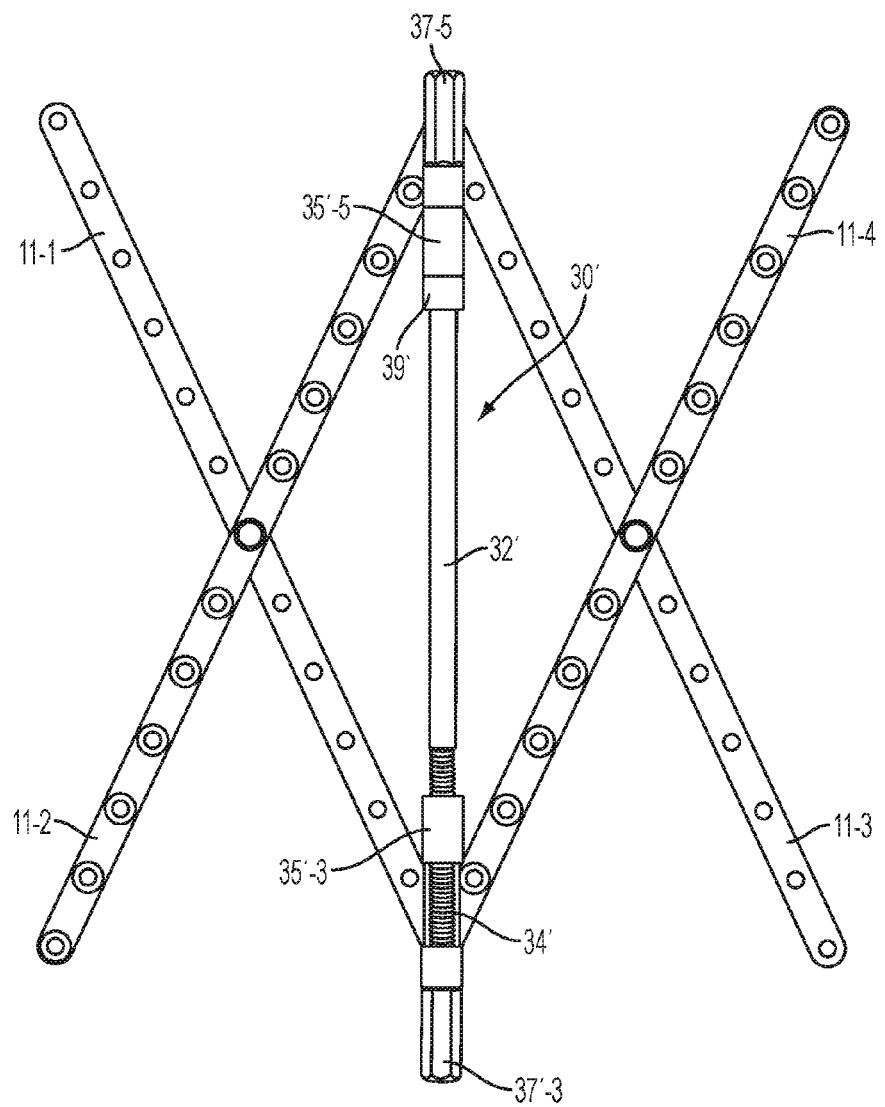
FIG. 6 is a perspective view of the support structure of FIG. 2 having another particular actuator mechanism.

FIG. 6 is a perspective view of the support structure of FIG. 2 having another particular actuator mechanism. As shown, the actuator mechanism 30' includes a single-threaded rod 32' positioned on the inside of the support structure 10 (FIG. 1). The rod 32' may include threads 34' on one of its ends. The rod 32' may be mounted to low profile anchor points 15-3, 15-5 using a pair of support mounts 35'-3, 35'-5, one of which is threaded to mate with the rod threads 34'. The unthreaded end of the rod 32' may include a retaining stop 39' that bears against the support mount 35'-5 to compress the support structure. Each end of the rod 32' can be terminated by a hex head 37'-3, 37'-5 for receiving a hex driver (not shown). Again, rotating the rod 32' in one direction may urge the anchor points 25-3, 25-5 outwardly to compress the linkages while rotating the rod 32' in the opposite direction may urge the anchor points 25-3, 25-5 inwardly to expand the linkages.

In addition, because the struts overlap, a ratcheting mechanism can be incorporated to be utilized during the sliding of one strut relative to the other. For example, the stent could lock at incremental diameters due to the interaction of features that are an integral part of each strut. An example of such features would be a male component (e.g. bumps) on one strut surface which mates with the female component (e.g. holes) on the surface of the neighboring strut surface, as the two struts slide pass one another. Such structures could be fabricated to have an orientation, such that they incrementally lock the stent in the expanded configuration as the stent is expanded. Such a stent could be expanded using a conventional balloon or other actuation mechanism described in this application.

Because the support structure 10 of FIGS. 5 and 6 may be configured to be implanted during a closed surgical procedure, the actuator mechanism may be able to be controlled remotely by a surgeon. In a typical procedure, the support structure 10 may be implanted through a body lumen, such as the femoral artery using a tethered endoluminal catheter. As such, the actuator mechanism 30 may be able to be controlled via the catheter.

Figure 7:
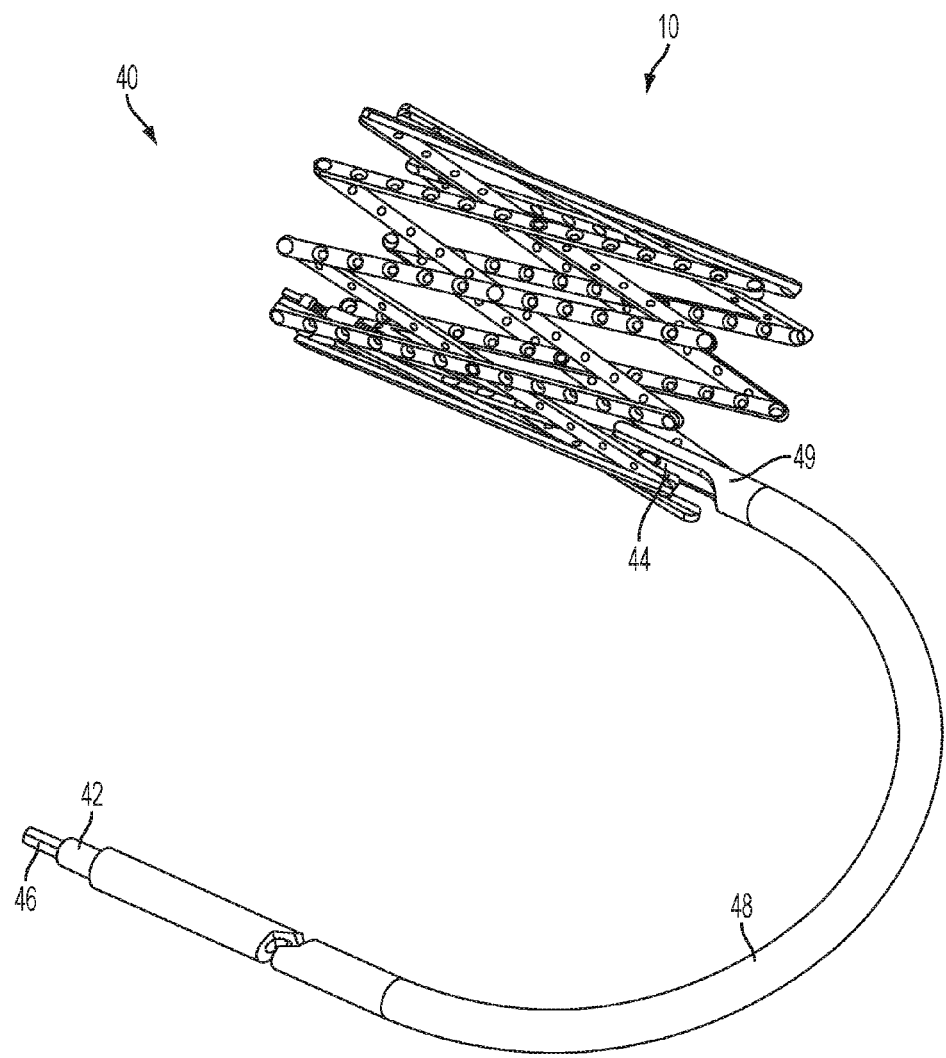
FIG. 7 is a perspective view of a particular support structure and control catheter assembly usable with the actuator mechanisms of FIGS. 5 and 6.

FIG. 7 is a perspective view of a particular support structure and control catheter assembly usable with the actuator mechanisms of FIGS. 5 and 6. The control catheter 40 may be dimensioned to be inserted with the support structure through a biological lumen, such as a human artery. As shown, the control catheter 40 includes a flexible drive cable 42 having a driver 44 on its distal end that removably mates with a hex head 37, 37' of the actuator mechanism (FIGS. 5 and 6). The proximal end of the cable 42 can include a hex head 46. In operation, the proximal hex head 46 of the cable 42 may be rotated by a surgeon, using a thumb wheel or other suitable manipulator (not shown). Rotation of the hex head 46 may be transferred by the cable 42 to the driver head 44 to turn the actuator rod 30, 30' (FIGS. 5 and 6).

The cable 42 may be encased by a flexible outer sheath 48. The distal end of the outer sheath 48 may include a lip or protuberance 49 shaped to interface with the support structure 10. When the cable 42 is turned, the outer sheath lip 49 may interact with the support structure 10 to counteract the resulting torque.

By employing threads, the rod may be self-locking to maintain the support structure in the desired diameter. In a particular embodiment, the rod 32, 32' may have a diameter of about 1.0 mm and a thread count of about 240 turns/inch. While a threaded rod and drive mechanism are described, other techniques can be employed to actuate the linkages depending on the particular surgical application. For example, the actuator mechanism can be disposed within the thickness of the strut members, instead of inside or outside of the stent. For example, worm gears or a rack and pinion mechanism can be employed as known in the art. One of ordinary skill in the art should recognize other endoluminal actuation techniques. In other situations, the support structure can be implanted during an open procedure, which may not require an external actuation mechanism.

Although there are other uses for the described support structure, such as drug delivery, a particular embodiment supports a prosthetic valve. In particular, the support structure may be used in combination with a prosthetic valve, such as for an aortic valve replacement.

Figure 8:
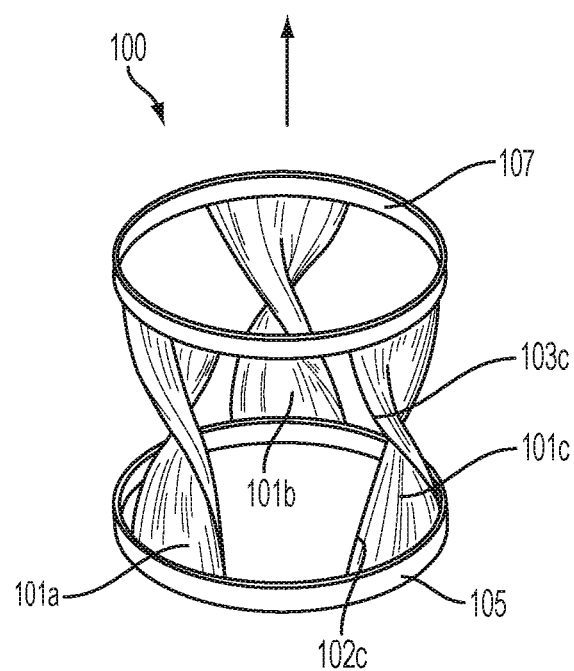
FIG. 8 is a perspective view of a particular rotating prosthetic valve assembly.

FIG. 8 is a perspective view of a particular rotating prosthetic valve assembly. The prosthetic valve 100 may comprise a three leaflet configuration shown in an open position. The leaflets may be derived from a biocompatible material, such as animal pericardium (e.g. bovine, porcine, equine), human pericardium, chemically treated pericardium, gluteraldehyde-treated pericardium, tissue engineered materials, a scaffold for tissue engineered materials, autologous pericardium, cadaveric pericardium, Nitinol, polymers, plastics, PTFE, or any other material known in the art.

The leaflets 101a, 101b, 101c may be attached to a stationary cylindrical member 105 and a non-stationary cylindrical member 107. One side of each leaflet 101 may be attached to the non-stationary cylindrical member 107. The opposing side of each leaflet 101 may be attached to the stationary cylindrical member 105. The attachment of each leaflet 101 may be in a direction generally perpendicular to the longitudinal axis of the cylindrical members 105, 107. In this embodiment, each leaflet 101 may be pliable, generally rectangular in shape, and may have a 180 degree twist between its attachments to stationary member 105 and non-stationary member 107. Each leaflet 101 may have an inner edge 102 and an outer edge 103, with the edges 102c, 103c of one leaflet 101c being referenced in the figure. As known in the art, the leaflets can be fabricated from either biological or non-biological materials, or a combination of both.

One way to actuate the valve to close may be by utilizing the forces exerted by the normal blood flow or pressure changes of the cardiac cycle. More specifically, the heart may eject blood through the fully open valve in the direction of the arrow shown in FIG. 8. Shortly thereafter, the distal or downstream blood pressure may start to rise relative to the proximal pressure across the valve, which may create a backpressure on the valve.

Figure 9:
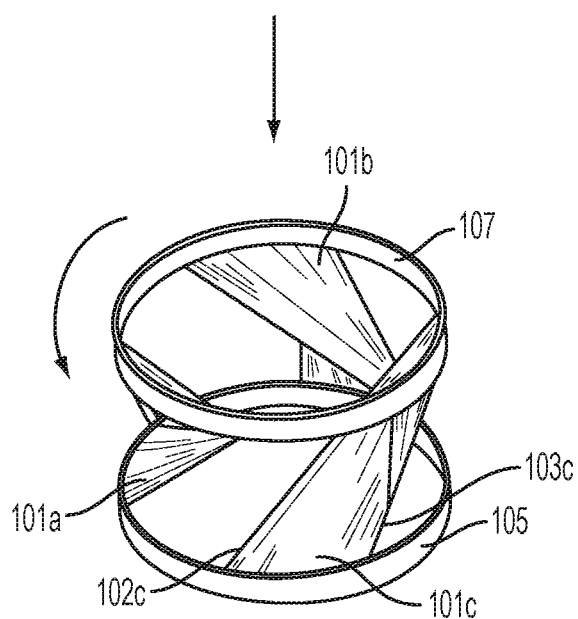
FIG. 9 is a perspective view of the valve assembly of FIG. 8 while being closed.

FIG. 9 is a perspective view of the valve assembly of FIG. 8 while being closed. That backpressure along the direction of the arrow may case the axially displacement of the leaflets 101 and non-stationary member 107 towards the stationary cylindrical member 105. As the leaflets 101 move from a vertical to horizontal plane relative to the longitudinal axis, a net counter-clockwise torque force may be exerted on the non-stationary member 107 and leaflets 101. The torque force may exert a centripetal force on the leaflets 101.

Figure 10:
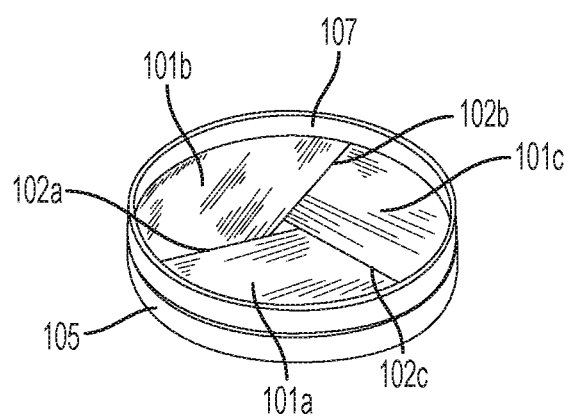
FIG. 10 is a perspective view of the valve assembly of FIG. 8 once completely closed.

FIG. 10 is a perspective view of the valve assembly of FIG. 8 once completely closed. Complete closure of the valve 100 may occur as the leaflets 101 displace to the center of the valve and the non-stationary cylindrical member 107 rests upon the stationary member 105, as shown.

The function of the valve 100 opening can be understood by observing the reverse of the steps of valve closing, namely following the sequence of drawings from FIG. 10 to FIG. 8.

In considering the valve 100 as an aortic valve replacement, it may remain closed as shown in FIG. 10, until the heart enters systole. During systole, as the myocardium forcefully contracts, the blood pressure exerted on the valve's proximal side (the side closest to the heart) may be greater than the pressure on the distal side (downstream) of the closed valve. This pressure gradient causes the leaflets 101 and non-stationary cylindrical member 107 to displace away from the stationary member 105 along the axial plane. The valve 100 may briefly assume the half-closed transition state shown in FIG. 9.

As the leaflets 101 elongate from a horizontal to vertical orientation along the axial plane, a net torque force may be exerted on the leaflets 101 and non-stationary cylindrical member 107. Since the valve 100 is opening, as opposed to closing, the torque force exerted to open the valve may be opposite to that exerted to close the valve. Given the configuration of embodiment shown in FIG. 9, the torque force that opens the valve would be in clockwise direction.

The torque forces may cause the leaflets 101 to rotate with the non-stationary member 107 around the longitudinal axis of the valve 100. This, in turn, may exert a centrifugal force on each leaflet 101. The leaflets 101 may undergo radial displacement away from the center, effectively opening the valve and allowing blood to flow away from the heart, in the direction shown by the arrow in FIG. 8.

To summarize, the valve may passively function to provide unidirectional blood flow by linking three forces. Axial, torque, and radial forces may be translated in a sequential and reversible manner, while encoding the directionality of prior motions. First, the axial force of blood flow and pressure may cause the displacement of the leaflets 101 and non-stationary members 107 relative to the stationary member 105 along the axial plane. This may be translated into a rotational force on the leaflets 101 and non-stationary member 107. The torque force, in turn, may displace the leaflets 101 towards or away from the center of the valve, along the radial plane, which may close or open the valve 100. The valve 100 passively follows the pathway of opening or closing, depending on the direction of the axial force initially applied to the valve by the cardiac cycle.

In the body, the stationary cylindrical member 105 may be secured and fixed in position at the implant site, while the non-stationary member 107 and distal ends of leaflets 101 may be free to displace along the axial plane. In using the prosthetic valve as an aortic valve replacement, the stationary member 105 could be secured in the aortic root. As the blood pressure or flow from the heart, increases, the valve 100 may change from its closed configuration to the open configuration, with blood ejecting through the valve 100.

Specific advantages of the rotating valve of FIGS. 8-10, along with further embodiments, are described in the above-incorporated parent provisional patent application.

Figure 11:
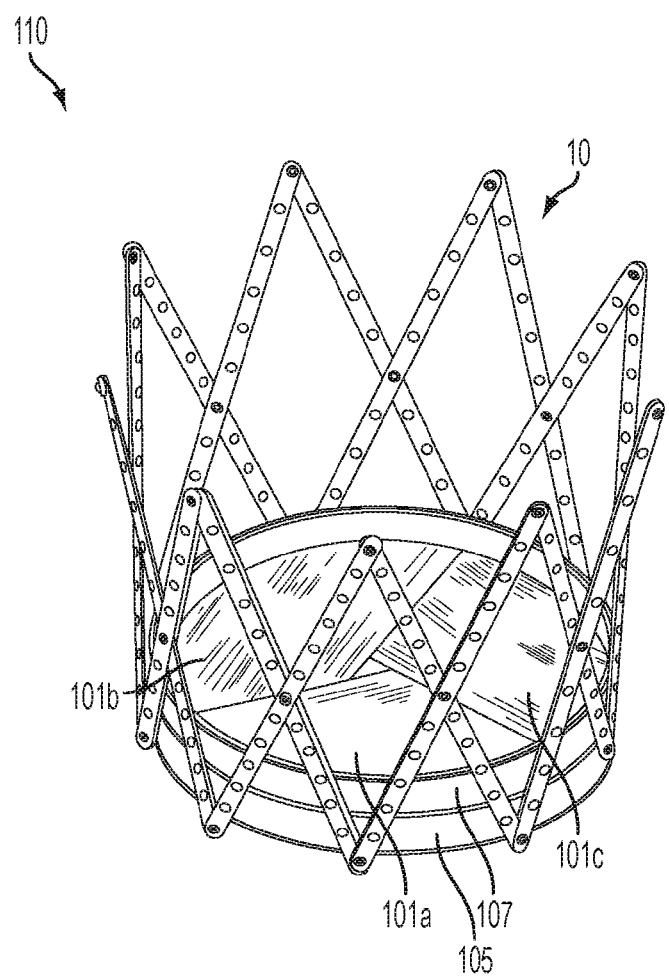
FIG. 11 is a perspective view of the valve of FIGS. 8-10 in combination with the support structure of FIG. 1.

FIG. 11 is a perspective view of the valve of FIGS. 8-10 in combination with the support structure of FIG. 1. As shown in the closed position, the valve's stationary member 105 is attached to the support structure 10. The valve's nonstationary member 107 may not be attached to the support structure 10. This may enable the non-stationary member 107 to displace along the axial plane along with the leaflets 101 during valve opening or closing. In this particular embodiment, the valve 100 may occupy a position that is closer to one end of the support structure 10, as shown.

Figure 12:
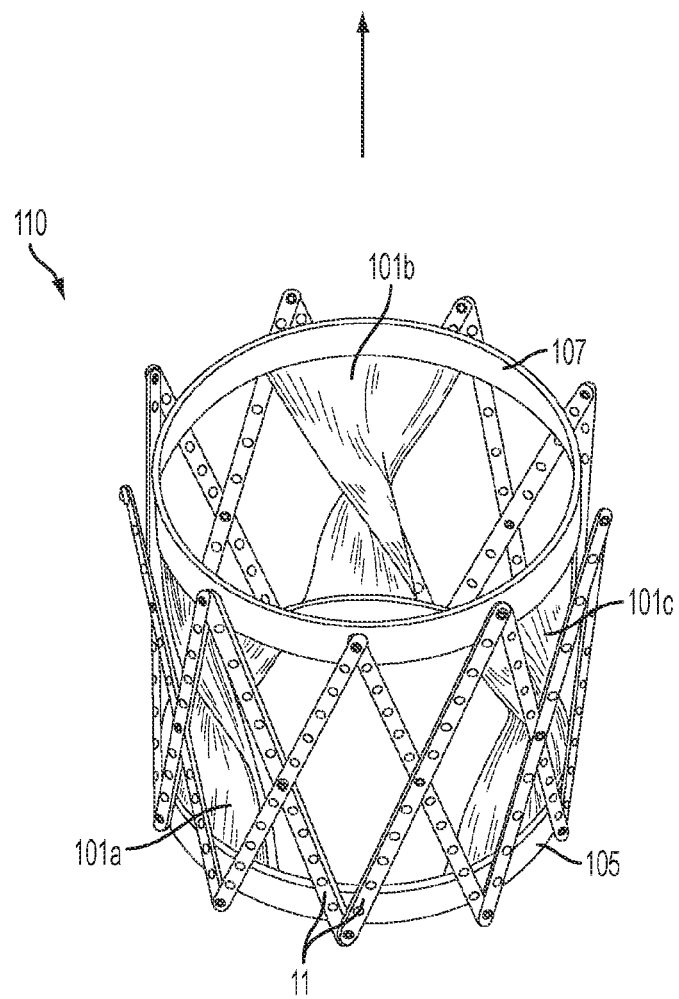
FIG. 12 is a perspective view of the valve of FIG. 11 in the open position.

FIG. 12 is a perspective view of the valve of FIG. 11 in the open position. As noted above, the non-stationary member 107 may not be attached to support structure 10, and may thus be free to displace along the axial plane, along with the leaflets 101. In this particular embodiment, during full opening, non-stationary member 107 and the leaflets 101 may remain within the confines of the support structure 10.

The stented valve 110 can be implanted during a closed procedure as described above. However, because of the operation of the non-stationary member within the body of the stent, the actuator mechanism to compress and expand the stent may not be disposed within the stent in such a case.

Further embodiments of the stented valve 110, positioning of the valve in the body, and procedures for implantation are described in the above-incorporated parent provisional patent application. In addition, a tissue valve can be draped on the support structure. Additional embodiments should be apparent to those of ordinary skill in the art.

Figure 13:
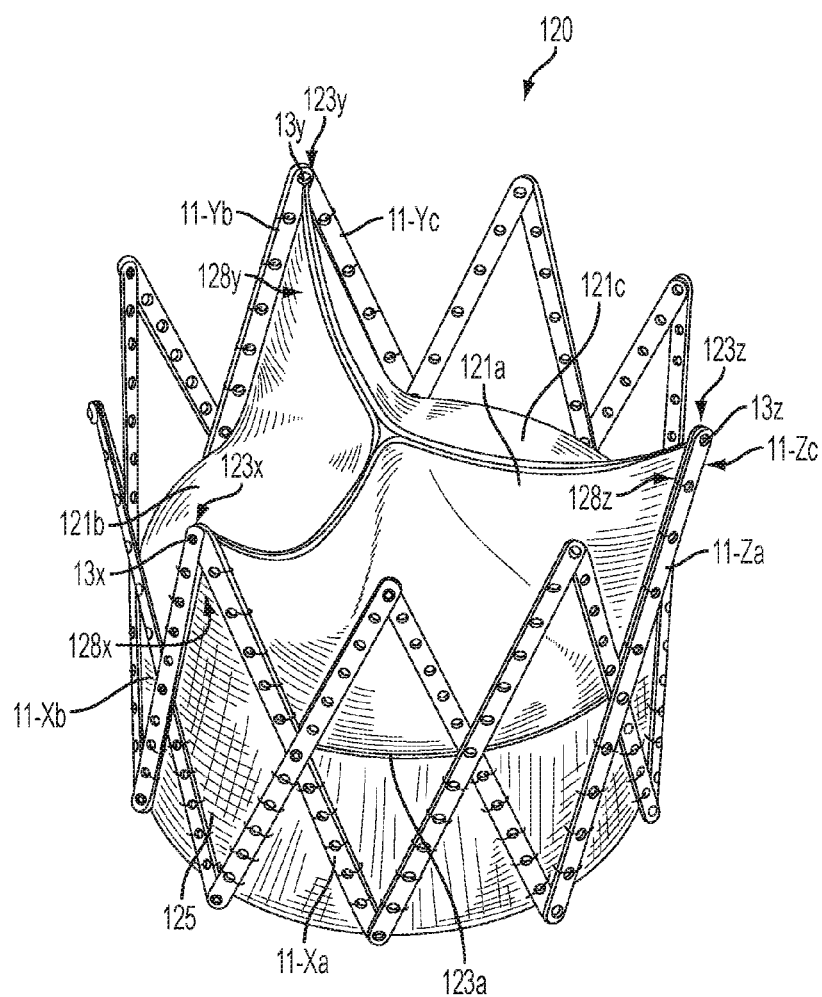
FIG. 13 is a perspective view of a traditional tissue valve mounted to the support structure of FIG. 1.

FIG. 13 is a perspective view of a traditional tissue valve mounted to the support structure of FIG. 1. As shown, a stented valve 120 may include a prosthetic tissue valve 121 attached to a support structure 10, such as that described above.

The tissue valve 121 may include three pliable semi-circular leaflets 121a, 121b, 121c, which can be derived from biocompatible materials as noted with reference to FIG. 8. Adjacent leaflets may be attached in pairs to commissures 123x, 123y, 123z on the support structure 10. In particular, the commissures 123x, 123y, 123z correspond to spaced-apart distal anchor points 13x, 13y, 13z on the support structure 10. In an 18-strut stent, the commissures may be attached the structure 10 via corresponding fasteners 25 at every third distal anchor point.

From the commissures, the leaflet sides may be connected to the adjacent diagonal struts. That is, the sides of the first leaflet 121a may be sutured to the struts 11-Xa and 11-Za, respectively; the sides of the second leaflet 121b may be sutured to the struts 11-Xb and 11-Yb, respectively; and the sides of the third leaflet 121c may be sutured to the struts 11-Yc and 11-Zc, respectively. Those sutures may end at the scissor pivot points on the diagonal struts.

In the configuration shown, neighboring struts 11 may be attached to one another in a manner that creates multiple arches 128 at the ends of the stent. Posts for leaflet attachment, or commissures, may be formed by attaching a corresponding leaflet to each of the struts that define a suitable arch 128x, 128y, 128z. In the configuration shown, there may be three leaflets 121a, 121b, 121c, each of which is attached to a strut along two of its opposing borders. The commissures may be formed by three equi-distant arches 128x, 128y, 128z in the stent.

The angled orientation of a strut in relationship to its neighboring strut may permit the leaflets 121a, 121b, 121c to be attached to the stent in a triangular configuration. This triangular configuration simulates the angled attachment of the native aortic leaflet. In the native valve this creates an anatomical structure between leaflets, known as the inter-leaflet trigone. Because the anatomical inter-leaflet trigone is believed to offer structural integrity and durability to the native aortic leaflets in humans, it may be advantageous to simulate this structure in a prosthetic valve.

One method of attachment of the leaflets to the struts is to sandwich the leaflet between a multi-ply strut. The multiple layers may then be held together by sutures, or the attachment may be sutureless. Sandwiching the leaflets between the struts may help to dissipate the forces on leaflets and prevent the tearing of sutures through the leaflets.

The remaining side of each leaflet 121a, 121b, 121c may be sutured annularly across the intermediate strut members as shown by a leaflet seam. The remaining open spaces between the struts can be draped by a biocompatible skirt 125 to help seal the valve against the implant site and thus limit paravalvular leakage. As shown, the skirt 125 may be shaped to cover those portions of the stent below and between the valve leaflets.

In more detail, the skirt 125 at the base of the valve may be a thin layer of material that lines the stent wall. The skirt material can be pericardial tissue, polyester, PTFE, or other material or combinations of materials suitable for accepting tissue in growth, including chemically treated materials to promote tissue growth or inhibit infection. The skirt layer may function to reduce or eliminate leakage around the valve, or "paravalvular leak." To that end, there are a number of ways to attach the skirt material layer to the stent, including:

- the skirt layer can be on the inside or the outside of the stent;
- the skirt layer can occupy the lower portion of the stent;
- the skirt layer can occupy the lower and upper portion of the stent;
- the skirt layer can occupy only the upper portion of the stent;
- the skirt layer can occupy the area between the struts that define the commissure posts;
- the skirt layer can be continuous with the leaflet material;
- the skirt layer can be sutured to the struts or a multitude of sites; or
- the skirt layer can be secured to the lower portion of the stent, and pulled or pushed up to cover the outside of the stent during the deployment in the body.

The above list is not necessarily limiting as those of ordinary skill in the art may recognize alternative draping techniques for specific applications.

Figure 14:
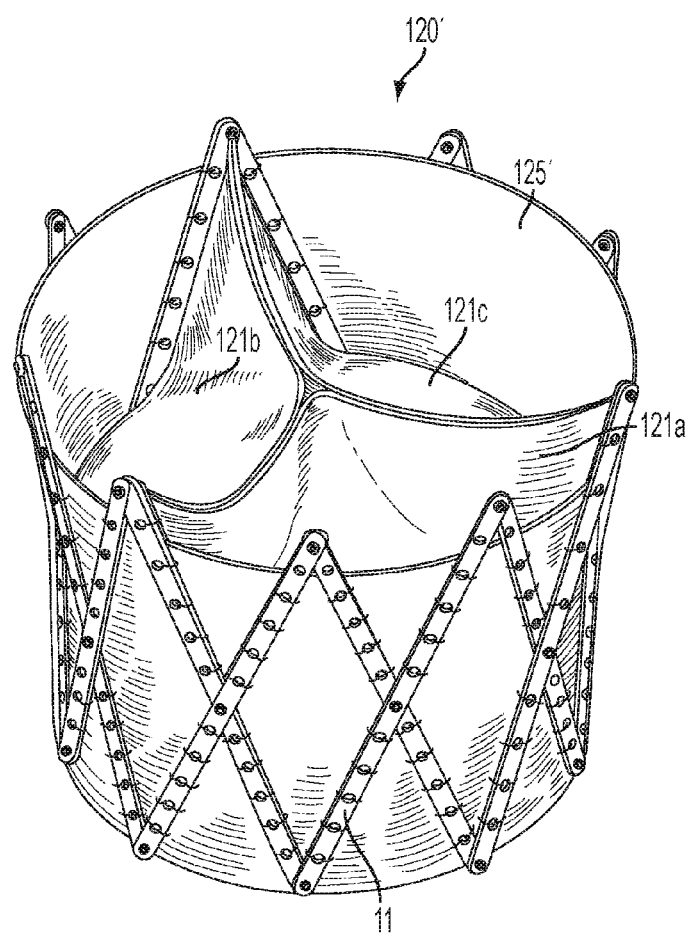
FIG. 14 is a perspective view of the valve structure of FIG. 13 having a full inner skirt.

FIG. 14 is a perspective view of the valve structure of FIG. 13 having a full inner skirt. A stented valve 120' may include a prosthetic tissue valve 121' having three leaflets 121a', 121b', 121c' attached to a support structure 10. A skirt layer 125' may cover the interior surface of the stent 10. As such, the valve leaflets 121a', 121b', 121c' may be sutured to the skirt layer 125'.

Figure 15:
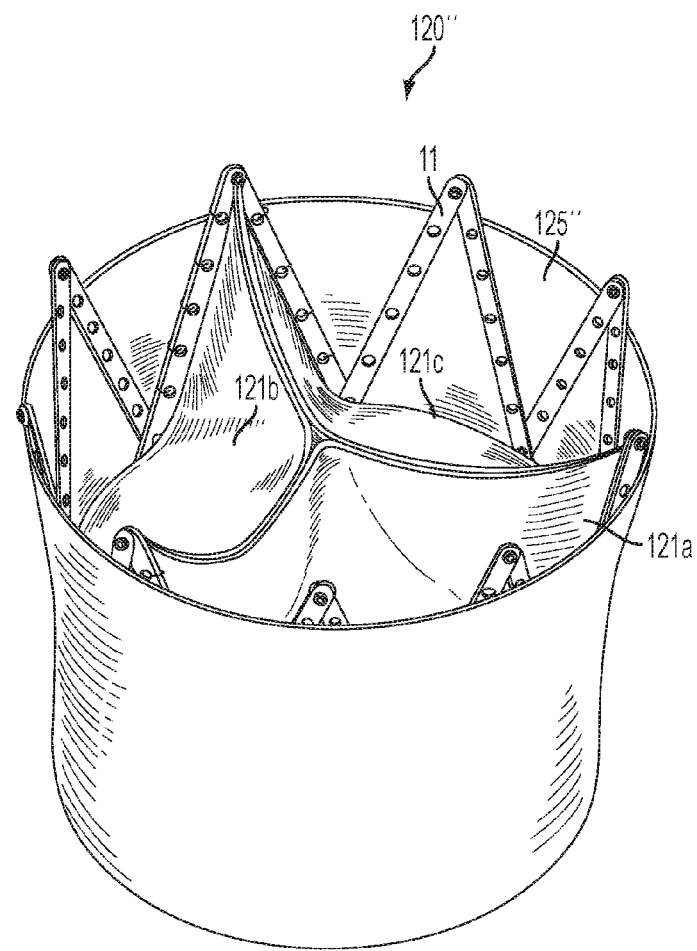
FIG. 15 is a perspective view of the valve structure of FIG. 13 having a full outer skirt.

FIG. 15 is a perspective view of the valve structure of FIG. 13 having a full outer skirt. A stented valve 120" may include a prosthetic tissue valve 121" having three leaflets 121a", 121b", 121c" attached to a support structure 10, such as that described in FIG. 13. A skirt layer 125" may cover the exterior surface of the stent 10.

The tissue valve structures 120, 120', 120" can also be implanted during a closed procedure as described above. However, the actuator mechanism to compress and expand the stent may be attached to avoid the commissure points and limit damage to the skirt layer 125, 125', 125", such as by mounting the actuator mechanism on the outer surface of the stent 10.

While the above-described embodiments have featured a support structure having linear strut bars and equal length scissor arms, other geometries may be employed. The resulting shape may be other than cylindrical and may have different performance characteristics in certain applications.

Figure 25:
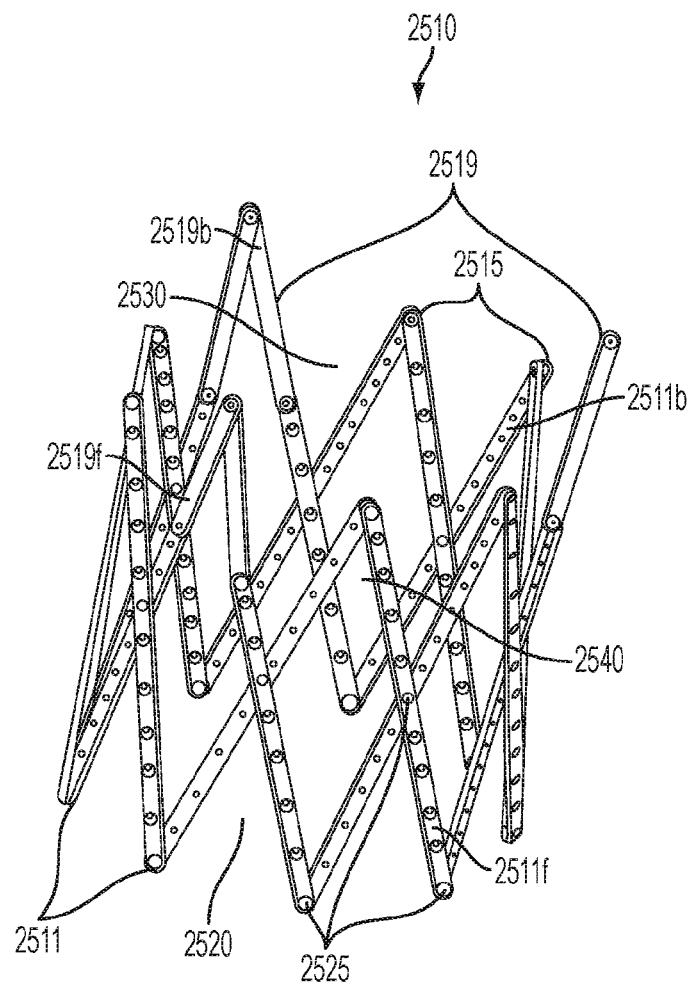
FIG. 25 is a perspective view of a particular endoluminal support structure.

For example, FIG. 25 is a perspective view of another support structure to which a traditional tissue valve may be mounted. The support structure may have a generally tubular shape comprising a proximal opening 2520, distal opening 2530, and a lumen 2540 therebetween. The tubular shape may be shorter and ring like as in the support structure 2510 in FIG. 25, or in other variations it may be elongate.

Like the support structure in FIG. 1, this support structure 2510 may include a plurality of longitudinal strut members 2511 and commissure strut members 2519 interconnected by a plurality articulations comprising pin or rotatable joints 2515. The commissure strut members 2519 and their articulations may permit regions of the support structure to extend further beyond the structure provided by the longitudinal strut members 2511, and which may expand and contract along with the configurational changes to the longitudinal strut members 2511, without generating significantly more resistance or stress in the structure, if any. As shown, there are eighteen struts 2511 and six struts 2519. The pin or rotatable joints 2515 may have an axis of rotation with a radial orientation and which may allow the interconnected strut members 2511 and 2519 to rotate relative to each other. One set of pin joints 2515 connecting longitudinal strut members 2511 may be located at the proximal ends of strut members 2511 in a plane aligned with the proximal opening 2520. A second set of pin joints 2511 connecting longitudinal strut members 2511 may be located at the distal ends of strut members 2511 in a plane aligned with the distal opening 2530. A third set of pin joints 2511 connecting longitudinal strut members 2511 may be located between the proximal opening 2520 and the distal opening 2530. A fourth set of pin joints 2511 connecting commissure strut members 2519 may be located distal to the plane of distal opening 2530. A fifth set of pin joints 2511 connecting longitudinal strut members 2511 to commissure strut members 2519 may be located proximal to the plane of distal opening 2530 between the third set of pin joints 2511 and the plane of distal opening 2530.

As in support structure 10 (FIG. 1), longitudinal strut members 2511 may be fabricated from a rigid or semi-rigid biocompatible material, such as plastics or other polymers and metal alloys, including stainless steel, tantalum, titanium, nickel-titanium (e.g. Nitinol), and cobalt-chromium (e.g.

ELGILOY). The dimensions of each strut can be chosen in accordance with its desired use. As shown, each longitudinal strut member 2511 is bar shaped and has a front surface 2511*f* and a back surface 2511*b*. In a particular embodiment, each strut member may be made from stainless steel, which may be about 0.001-0.100 inch thick. More particularly, each strut may be about 0.01 inch thick 300 series stainless steel. In another embodiment, each strut member may be made from cobalt-chromium (e.g. ELGILOY). While all struts 2511 are shown as being of uniform thickness, the thickness of a strut can vary across a strut, such as a gradual increase or decrease in thickness along the length of a strut. Furthermore, individual struts 2511 can differ in thickness from other individual struts 2511 in the same support structure. In a particular embodiment, each strut member 2511 may be about 0.01-0.25 inches wide. More particularly, each strut 2511 may be about 0.06 inches wide. While all struts 2511 are shown as being of a uniform width, a strut can vary in width along its length. Furthermore, an individual strut 2511 can have a different width than another strut 2511 in the same support structure 2510. The particular dimensions can be chosen based on the implant site. The strut lengths can vary from strut to strut within the same support structure, as is explained in detail below.

Commissure strut members 2519 may be fabricated from the same materials as described above for longitudinal strut members 2511 above, or in some variations they are fabricated from biocompatible materials having greater flexibility than the materials from which longitudinal strut members 2511 are fabricated. Such biocompatible materials can include plastics or other polymers and metal alloys, including stainless steel, Nitinol, cobalt-chromium, and the like. The dimensions of each commissure strut 2519 can be chosen in accordance with its desired use. As shown, each longitudinal strut member 2519 is bar shaped and has a front surface 2519*f* and a back surface 2519*b*. In a particular embodiment, each strut member can be made from stainless steel, which may be about 0.001-0.100 inch thick. More particularly, each strut may be about 0.01 inch thick 300 series stainless steel. In another embodiment, each strut member may be made from cobalt-chromium (e.g. ELGILOY). While all struts 2519 are shown as being of uniform thickness, the thickness of a strut can vary across a strut, such as a gradual increase or decrease in thickness along the length of a strut. Furthermore, individual struts 2519 can differ in thickness from other individual struts 2519 in the same support structure. In a particular embodiment, each strut member 2519 may be about 0.01-0.25 inches wide. More particularly, each strut 2519 may be about 0.06 inches wide. While all struts 2519 are shown as being of a uniform width, a strut can vary in width along its length. Furthermore, an individual strut 2519 can have a different width than another strut 2519 in the same support structure 2510. The particular dimensions can be chosen based on the implant site. The strut lengths can vary from strut to strut within the same support structure, as is explained in detail below.

The strut members can, however, optionally comprise different geometries. For instance, the longitudinal struts 2511 and commissure struts 2519 can be non-flat structures. In particular, the struts can include a curvature, such as in a concave or convex manner in relationship to the inner diameter of the support structure 2510. The struts can also be twisted. The nonflatness or flatness of the struts can be a property of the material from which they are constructed. For example the struts can exhibit shape-memory or heat responsive changes in shape to the struts during various states. Such states can be defined by the support structure in the compressed or expanded configuration. The struts can also exhibit changes in shape due to stressed on them while implanted. For instance, if used to support a prosthetic valve assembly as described in detail below, the stress on the commissure struts 2519 during the normal cardiac cycle may cause the commissure struts 2519 to permanently or temporarily bend or otherwise change shape. In variations in which the commissure strut members 2519 are fabricated from biocompatible materials having greater flexibility than the materials from which the longitudinal strut members 2511 are fabricated, if a force including a radially inward component is applied to the commissure strut members, they may flex inward, while the longitudinal strut members 2511 may not substantially deform.

Furthermore, the strut members 2511 and 2519 can have a smooth or rough surface texture. In particular, a pitted surface can provide tensile strength to the struts. In addition, roughness or pitting can provide additional friction to help secure the support structure at the implant site and encourage encapsulation of the support structure 2510 by tissue growth to further stabilize and support structure 2510 at the implant site over time.

In certain instances, the support structure 2510 could be comprised of struts that are multiple members stacked upon one another. Within the same stent, some struts could include elongated members stacked upon one another in a multi-ply configuration, and other struts could be one-ply, composed of single-thickness members. Within a single strut, there can be areas of one-ply and multi-ply layering of the members.

Each longitudinal strut member 2511 may also include a plurality of orifices 2513 spaced along the length of strut members 2511. On the front surface 2511*f*, orifices may be countersunk to receive the head of a fastener. The orifices 2513 are shown as being of uniform diameter and uniform spacing along the strut members 2511, but neither is required. FIG. 25 shows commissure strut members 2519 as not having orifices 2513 along their lengths. However, in other instances, the commissure strut members 2519 can have orifices 2513 along their lengths. Orifices 2513 on commissure strut members 2519 can similarly be countersunk on front surface 2519*f* to receive the head of a fastener. Orifices 2513 on commissure strut members 2519 can also similarly be of uniform diameter and uniform spacing along strut members 2519, but again neither is required. The orifices 2513 can receive fasteners as described in detail below, and then can provide an additional pathway for tissue growth-over to stabilize and encapsulate support structure 2510 over time. In FIG. 25, longitudinal strut members 2511-1 and 2511-4 (FIG. 26) have thirteen orifices 2513 and longitudinal strut members 2511-2 and 2511-3 (FIG. 26) have ten orifices 2513. There can, however, be more or fewer orifices on longitudinal strut members 2511.

Figure 26:
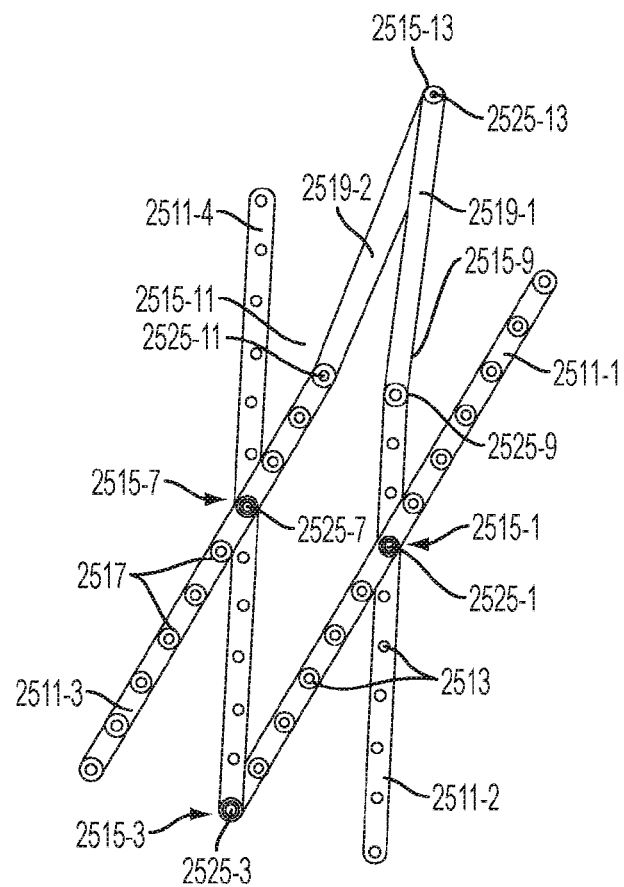
FIG. 26 is a perspective view of a six strut section of the structure of FIG. 25.

The strut members 2511 and 2519 may be arranged as a chain of four- and six-bar linkages, and wherein at least some, if not all, of the linkage sets share common struts with adjacent linkages and configuration changes to one linkage will generate complementary changes to the other linkages linked by common struts. Complementary changes, however, are not necessarily limited to linkages or struts with common struts. The four-bar linkages may have the same configuration as the four strut section of the stent of FIG. 1, shown in FIG. 2 and described in detail above. FIG. 26 is a perspective view of a six-bar linkage of the support structure of FIG. 25. As shown, two outer strut members 2511-1, 2511-3 overlap two inner strut members 2511-2, 2511-4, with their back surfaces in communication with each other. In addition, two commissure strut members—outer commissure strut member 2519-1 and inner commissure strut member 2519-2—can be connected to inner strut member 2511-2 and outer strut member 2511-3.

The strut members 2511, 2519 may be interconnected by rotatable or swivelable pivot fasteners 2525, such as rivets, extending through aligned orifices. It should be understood that other rotatable or swivelable fasteners 2525 can be employed such as screws, bolts, ball-in-socket structures, nails, or eyelets, and that the fasteners can be integrally formed in the struts 2511, 2519 such as a peened semi-sphere interacting with an indentation or orifice, or a male-female coupling.

In particular, the outer strut member 2511-1 may be rotatably or swivelably connected to the inner strut member 2511-2 by a pin joint 2515-1 using a rivet 2525-1, which utilizes orifices 2913. The pin joint 2525-1 may bisect outer strut member 2511-1. The pin joint 2525-1 may not bisect inner strut member 2511-2, but instead utilize an orifice 2513 that is offset distally from the longitudinal center of inner strut member 2511-2. It should be understood that the joint 2515-1 may utilize different orifices 2513 than the ones shown in FIG. 26.

The outer strut member 2511-3 may be rotatably connected to the inner strut member 2511-4 by a pin joint 2515-7 using a rivet 2525-7, which utilizes orifices 13. The pin joint 2525-7 may bisect inner strut member 2511-4. The pin joint 2525-7 may not bisect outer strut member 2511-3, but instead utilize an orifice 2513 that is offset distally from the longitudinal center on outer strut member 2511-3. It should be understood that the joint 2515-7 may utilize different orifices 2513 than the ones shown in FIG. 26.

In addition to the joint 2515-1, the outer strut member 2511-1 may be rotatably connected to the inner strut member 2511-4 by a proximal anchor pin joint 2515-3 using rivet 2525-3, located near the proximal ends of the strut members 2511-1, 2511-4. The inner strut member 2511-2 may also be rotatably connected to the commissure strut member 2519-1 by a pin joint 2515-9 using a rivet 2525-9, located near the distal end of inner strut member 2511-2 and the proximal end of commissure strut member 2519-1. Likewise, the outer strut member 2511-3 may be rotatably connected to the commissure strut member 2519-2 by a pin joint 2515-11 using a rivet 2525-11, located near the distal end of outer strut member 2511-3 and the proximal end of commissure strut member 2519-2. Commissure strut member 2519-1 may also be rotatably connected to commissure strut member 2519-2 by a distal anchor pin joint 2515-13 using rivet 2525-13, located near the distal ends of the commissure strut members 2519-1, 2519-2.

Strut members 2511, 2519 may have lengths chosen based on the implant site. In a particular embodiment, outer longitudinal strut 2511-1 and inner longitudinal strut 2511-4 may have approximately the same length, inner longitudinal strut 2511-2 and outer longitudinal strut 2511-3 may have approximately the same length, and commissure struts 2519-1, 2519-2 may have approximately the same length. In that embodiment the length of outer longitudinal strut 2511-1 and inner longitudinal strut 2511-4 may be greater than the length of inner longitudinal strut 2511-2 and outer longitudinal strut 2511-3. In that embodiment, the combined longitudinal length of longitudinal strut member 2511-2 and commissure strut member 2519-1 may be greater than the length of longitudinal strut member 2511-1 or longitudinal strut member 2511-4. In that embodiment, the combined longitudinal length of longitudinal strut member 2511-3 and commissure strut member 2519-2 may be greater than the length of longitudinal strut member 2511-1 or longitudinal strut member 2511-4. In some embodiments the combined length of longitudinal strut member 2511-2 and commissure strut member 2519-1 may be at least 20% longer than the length of longitudinal strut members 2511-1 or 2511-4. Similarly the combined longitudinal length of longitudinal strut member 2511-3 and commissure strut member 2519-2 may be at least 20% longer than the length of longitudinal strut members 2511-1 or 2511-4. Distal anchor pin joint 2515-13, located near the distal ends of commissure strut members 2519-1 and 2519-2 may extend beyond the plane of the distal opening 2530 by a longitudinal distance that is at least 20% of the longitudinal distance between the planes of the proximal opening 2520 and distal opening 2530. In one embodiment outer longitudinal strut 2511-1 and inner longitudinal strut 2511-4 may be about 0.250-3.00 inches long; inner longitudinal strut 2511-2 and outer longitudinal strut 2511-3 may be about 0.1-2.5 inches long; and commissure struts 2519-1, 2519-2 may be about 0.1-2.5 inches long. More particularly, outer longitudinal strut 2511-1 and inner longitudinal strut 2511-4 may be about 0.5 inches long; inner longitudinal strut 2511-2 and outer longitudinal strut 2511-3 may be about 0.375 inches long; and commissure struts 2519-1, 2519-2 may be about 0.2 inches long.

To reduce stress on the anchor rivets 2525-3, 2525-13, the proximal ends of struts 2511-1, 2511-4 and distal ends of commissure struts 2519-1, 2519-2 may be curved or twisted to provide a flush interface between the joined struts.

As can be seen in FIG. 25, the support structure 2510 may be fabricated by linking together a chain of individual six-strut sections (FIG. 26) and four-strut sections (FIG. 2). The chain may then be wrapped or otherwise connected back to itself to join the last section with the first section in the chain. As shown in FIG. 25, a chain of three six-strut sections and six four-strut sections may be joined, such that every third section is a six-strut section. It should be understood that different numbers of four-strut sections may be linked with the three six-strut sections. In some variations, the support structure may have zero four-strut sections and consist only of six-strut sections. As in the support structure 10 shown in FIG. 1, actuating the linkage may cause the links to be opened or closed, which may result in expanding or compressing the support structure 2510 (FIG. 25). When the support structure is in neither a fully expanded nor fully compressed state, the angle between commissure strut members 2519-1, 2519-2 at distal anchor pin joint 2515-13 may be less than the angle between two longitudinal strut members 2511 at an anchor pin joint 2515 located near the distal ends of the two longitudinal strut members 2511. The diameter of support structure 2510 can be chosen based on the implant site. In a particular embodiment for implantation at the mitral valve opening, the diameter may be about 0.5-1.55 inches. More particularly, the diameter may be about 0.8 inches.

Figure 28:
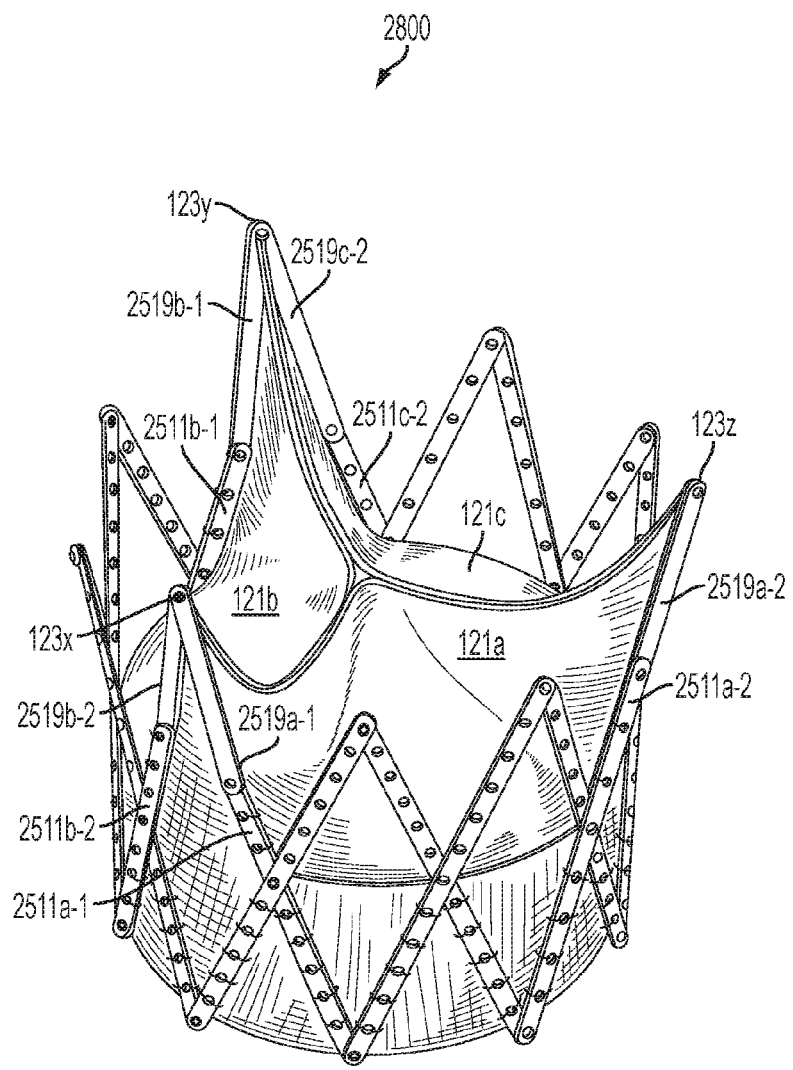
FIG. 28 is a schematic perspective view of a traditional tissue valve mounted to the structure of FIG. 25.

FIG. 28 is a perspective view of a traditional tissue valve mounted to the support structure of FIG. 25. As shown, a stented valve 2800 may include a prosthetic tissue valve 121, as described above, to a support structure 2510, as described above. Adjacent leaflets may be attached in pairs to commissures 123*x*, 123*y*, 123*z* on support structure 2510, which correspond to the distal pin joints 2515 located at the distal ends of commissure strut members 2519.

From the commissures, the leaflet sides may be connected to the adjacent struts. That is, the sides of the first leaflet 121*a* may be sutured to the struts 2511*a*-1, 2519*a*-1, 2511*a*-2, 2519*a*-2; the sides of the second leaflet 121*b* may be sutured to the struts 2511*b*-1, 2519*b*-1, 2511*b*-2, 2519*b*-2; and the sides of the third leaflet 121*c* may be sutured to the struts 2511*c*-1, 2519*c*-1, 2511*c*-2, 2519*c*-2. Those sutures end at the scissor pivot points 2515 on the longitudinal struts 2511.

Like the attachment of leaflets to support structure 10 shown in FIG. 13, the angled orientation of a strut in relationship to its neighboring strut may enable the leaflets 121*a*, 121*b*, 121*c* to be attached to the stent in a triangular configuration. This triangular configuration may simulate the angled attachment of the native leaflet and allow for anatomical draping of the tissue. In the native valve this creates an anatomical structure between leaflets, known as the inter-leaflet trigone. Because the anatomical inter-leaflet trigone is believed to offer structural integrity and durability to the native leaflets in humans, it is advantageous to simulate this structure in a prosthetic valve.

The tissue valve mounted to support structure shown in FIG. 25 may also be modified to sandwich the leaflets between multi-ply struts, and to drape the open spaces between the struts with a biocompatible skirt, as described in more detail above regarding FIGS. 14-15.

In another embodiment, the tissue valve 121 may be mounted to the support structure 2510 in a secure, sutureless manner. Leaflets 121*a*, 121*b*, 121*c* can be suturelessly attached at the distal tip of commissures 123*x*, 123*y*, 123*z*, and along the distal portion of struts 2511. In some variations, the leaflets 121*a*, 121*b*, 121*c* can also be suturelessly attached along struts 2519. More particularly, the sides of leaflet 121*a* may be suturelessly attached to the struts 2511*a*-1, 2511*a*-2; the sides of leaflet 121*b* may be suturelessly attached to the struts 2511*b*-1, 2511*b*-2; and the sides of leaflet 121*c* may be suturelessly attached to the struts 2511*c*-1, 2511*c*-2. In some variations, the sides of leaflet 121*a* can be suturelessly attached to the struts 2919*a*-1, 2519*a*-2; the sides of leaflet 121*b* can be suturelessly attached to the struts 2519*b*-1, 2519*b*-2; and the sides of leaflet 121*c* can be suturelessly attached to the struts 2519*c*-1, 2519*c*-2.

The sutureless attachments may be formed by draping the leaflets over the distal tips of commissures 123*x*, 123*y*, 123*z*; sandwiching the leaflets between struts at pivot joints; or sandwiching the leaflets between multi-ply struts. More particularly, the sides of leaflet 121*a* can be sandwiched between the commissure strut 2519*c*-1 and commissure strut 2519*a*-2 at the pivot joint at distal tip of commissure 123*z*; sandwiched between commissure strut 2519*a*-2 and longitudinal strut 2511*a*-2 at the connecting pivot joint; sandwiched between longitudinal strut 2511*a*-2 and the rotatably attached longitudinal strut 2511 at the middle pivot joint 2515; sandwiched between commissure strut 2519*a*-1 and commissure strut 2519*b*-2 at the pivot joint at distal tip of commissure 123*x*; sandwiched between commissure strut 2519*a*-1 and longitudinal strut 2511*a*-1 at the connecting pivot joint; and sandwiched between longitudinal strut 2511*a*-1 and the rotatably attached longitudinal strut 2511 at the middle pivot joint 2515. The rivets 2525 at these pivot joints may pass through the leaflet 121*a*.

The sides of leaflet 121*b* can be sandwiched between the commissure strut 2519*a*-1 and commissure strut 2519*b*-2 at the pivot joint at distal tip of commissure 123*x*; sandwiched between commissure strut 2519*b*-2 and longitudinal strut 2511*b*-2 at the connecting pivot joint; sandwiched between longitudinal strut 2511*b*-2 and the rotatably attached longitudinal strut 2511 at the middle pivot joint 2515; sandwiched between commissure strut 2519*b*-1 and commissure strut 2519*c*-2 at the pivot joint at distal tip of commissure 123*y*; sandwiched between commissure strut 2519*b*-1 and longitudinal strut 2511*b*-1 at the connecting pivot joint; and sandwiched between longitudinal strut 2511*b*-1 and the rotatably attached longitudinal strut 2511 at the middle pivot joint 2515. The rivets 2525 at these pivot joints may pass through the leaflet 121*b*.

The sides of leaflet 121*c* can be sandwiched between the commissure strut 2519*b*-1 and commissure strut 2519*c*-2 at the pivot joint at distal tip of commissure 123*y*; sandwiched between commissure strut 2519*c*-2 and longitudinal strut 2511*c*-2 at the connecting pivot joint; sandwiched between longitudinal strut 2511*c*-2 and the rotatably attached longitudinal strut 2511 at the middle pivot joint 2515; sandwiched between commissure strut 2519*c*-1 and commissure strut 2519*a*-2 at the pivot joint at distal tip of commissure 123*z*; sandwiched between commissure strut 2519*c*-1 and longitudinal strut 2511*c*-1 at the connecting pivot joint; and sandwiched between longitudinal strut 2511*c*-1 and the rotatably attached longitudinal strut 2511 at the middle pivot joint 2515. The rivets 2525 at these pivot joints may pass through the leaflet 121*c*.

In another embodiment, struts 2511*a*-1, 2511*a*-2, 2511*a*-3, 2511*b*-1, 2511*b*-2, 2511*b*-3, 2511*c*-1, 2511*c*-2, 2511*c*-3, 2519*a*-1, 2519*a*-2, 2519*a*-3, 2519*b*-1, 2519*b*-2, 2519*b*-3, 2519*c*-1, 2519*c*-2, 2519*c*-3 are multi-ply struts, and the leaflets 121*a*, 121*b*, 121*c* are sandwiched between the two or more layers of the struts. More particularly, one side of leaflet 121*a* may be sandwiched within the multi-ply strut making up commissure strut 2519*a*-1 and the multi-ply strut making up the distal portion of longitudinal strut 2511*a*-1, and the other side of leaflet 121*a* may be sandwiched within the multi-ply strut making up commissure strut 2519*a*-1 and the multi-ply strut making up the distal portion of longitudinal strut 2511*a*-2. One side of leaflet 121*b* may be sandwiched within the multi-ply strut making up commissure strut 2519*b*-1 and the multi-ply strut making up the distal portion of longitudinal strut 2511*b*-1, and the other side of leaflet 121*b* may be sandwiched within the multi-ply strut making up commissure strut 2519*b*-1 and the multi-ply strut making up the distal portion of longitudinal strut 2511*b*-2. One side of leaflet 121*c* may be sandwiched within the multi-ply strut making up commissure strut 2519*c*-1 and the multi-ply strut making up the distal portion of longitudinal strut 2511*c*-1, and the other side of leaflet 121*c* may be sandwiched within the multi-ply strut making up commissure strut 2519*c*-1 and the multi-ply strut making up the distal portion of longitudinal strut 2511*c*-2.

Figure 34:
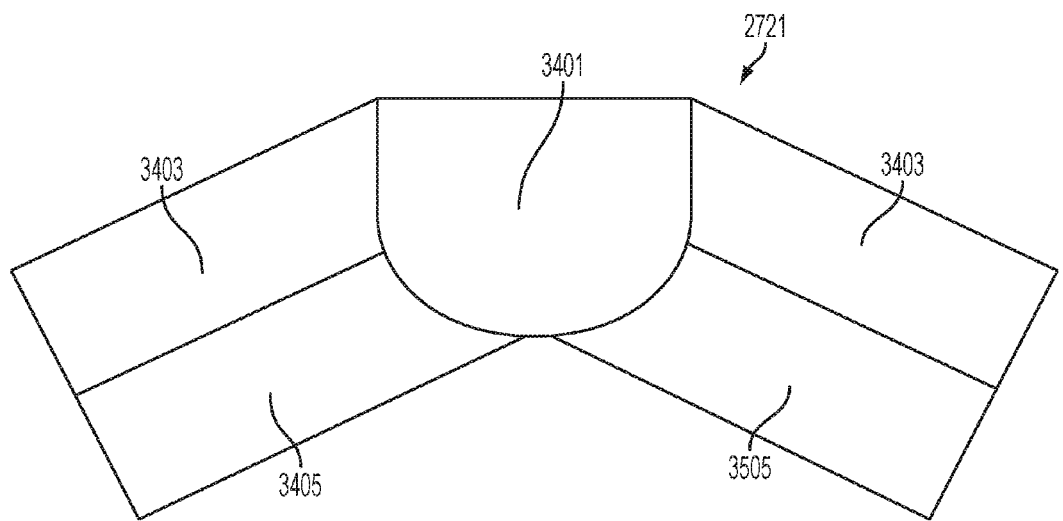
FIG. 34 is a schematic illustration of a valve leaflet.

In order to facilitate secure, suture-free leaflet attachment during fabrication through sandwiching of the leaflets between the struts, the leaflets 121*a*, 121*b*, 121*c* may comprise a shape as shown in FIG. 34 having a central region 3401 having a semicircular or paraboloid shape, with two rectangular regions extending from each side of the central region 3401. The upper rectangular regions 3403 may be sandwiched within multi-ply struts making up commissure struts 2519, and the lower rectangular regions 3405 may be sandwiched within multi-ply struts making up longitudinal struts 2511. After the upper regions 3403 and lower regions 3405 are sandwiched between the struts, the outer portions of the regions 3403, 3405 can be removed (e.g. by being cut off), leaving the central region 3401 suturelessly attached to the support structure 2510.

Figure 27A:
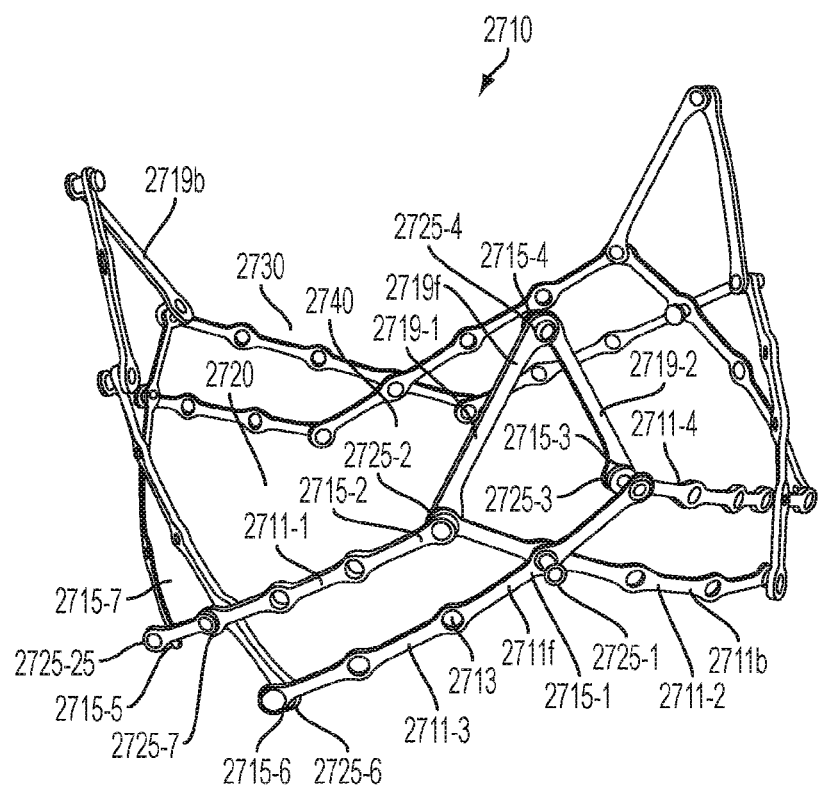
FIG. 27A is a perspective view of another embodiments of an endoluminal support structure.

In other embodiments, tissue valves may be mounted to the other support structures described herein, such as the support structure shown in FIGS. 13-15 and the support structure 2710 shown in FIG. 27A, in the sutureless manner described above.

FIG. 27A is a perspective view of another support structure to which a traditional tissue valve can be mounted. The support structure may have a tubular shape having a proximal opening 2720, distal opening 2730, and a lumen 2740 therebetween. The tubular shape may be shorter and ring like as in the support structure 2710 in FIG. 27A, or in other variations it may be elongate.

Like the support structures in FIGS. 1 and 25, support structure 2710 may include a plurality of longitudinal strut members 2711 and commissure strut members 2719 interconnected by a plurality of pin joints 2715. As shown, there are twelve struts 2711 and six struts 2719. The pin joints 2715 may have an axis of rotation with radial orientation, which may allow the interconnected strut members 2711 and 2719 to rotate relative to each other. One set of pin joints 2715 connecting longitudinal strut members 2711 may be located at the proximal ends of strut members 2711 in a plane aligned with proximal opening 2720. A second set of pin joints 2711 connecting longitudinal strut members 2711 to each other and to commissure strut members 2719 may be located at the distal ends of longitudinal strut members 2711 and the proximal ends of commissure strut members 2719 and in a plane aligned with the distal opening 2730. A third set of pin joints 2711 connecting longitudinal strut members 2711 may be located between the proximal opening 2720 and distal opening 2730 and proximal to the midpoint between the proximal opening 2720 and distal opening 2730. A fourth set of pin joints 2711 may be located between the proximal opening 2720 and distal opening 2730 and distal to the midpoint between the proximal opening 2720 and distal opening 2730. A fifth set of pin joints 2711 connecting commissure strut members 2719 may be located distal to the plane of distal opening 2530.

As in support structures 10 (FIG. 1) and 2510 (FIG. 25), longitudinal strut members 2711 may be fabricated from a rigid or semi-rigid biocompatible material, such as plastics or other polymers and metal allows, including stainless steel, tantalum, titanium, nickel-titanium (e.g. Nitinol), and cobalt-chromium (e.g. ELGILOY). The dimensions of each strut can be chosen in accordance with its desired use. As shown, each longitudinal strut member 2711 is bar shaped and has a front surface 2711*f* and a back surface 2711*b*. In a particular embodiment, each strut member may be made from stainless steel, which may be about 0.001-0.100 inch thick. More particularly, each strut may be about 0.01 inch thick 300 series stainless steel. In another embodiment, each strut member is made from cobalt-chromium (e.g. ELGILOY). While all struts 2711 are shown as being of uniform thickness, the thickness of a strut can vary across a strut, such as a gradual increase or decrease in thickness along the length of a strut. Furthermore, individual struts 2711 can differ in thickness from other individual struts 2711 in the same support structure. In a particular embodiment, each strut member 2711 may be about 0.01-0.25 inches wide. More particularly, each strut 2711 may be about 0.06 inches wide. While all struts 2711 are shown as being of a uniform width, a strut can vary in width along its length. Furthermore, an individual strut 2711 can have a different width than another strut 2711 in the same support structure 2710. The particular dimensions can be chosen based on the implant site. The strut lengths can vary from strut to strut within the same support structure, as is explained in detail below.

Commissure strut members 2719 may be fabricated from the same materials as described above for longitudinal strut members 2711 above, or in some variations they are fabricated from biocompatible materials having greater flexibility than the materials from which longitudinal strut members 2711 are fabricated. Such biocompatible materials can include the materials as described elsewhere herein. The dimensions of each commissure strut 2719 can be chosen in accordance with its desired use. As shown, each longitudinal strut member 2719 is bar shaped and has a front surface 2719*f* and a back surface 2719*b*. In a particular embodiment, each strut member may be made from stainless steel, which may be about 0.001-0.100 inch thick. More particularly, each strut may be about 0.01 inch thick 300 series stainless steel. While all struts 2719 are shown as being of uniform thickness, the thickness of a strut can vary across a strut, such as a gradual increase or decrease in thickness along the length of a strut. Furthermore, individual struts 2719 can differ in thickness from other individual struts 2719 in the same support structure. In a particular embodiment, each strut member 2719 may be about 0.010-0.250 inches wide. More particularly, each strut 2719 may be about 0.06 inches wide. While all struts 2719 are shown as being of a uniform width, a strut can vary in width along its length. Furthermore, an individual strut 2719 can have a different width than another strut 2719 in the same support structure 2710. The particular dimensions can be chosen based on the implant site. The strut lengths can vary from strut to strut within the same support structure, as is explained in detail below.

The strut members can however be of different geometries. For instance, the longitudinal struts 2711 and commissure struts 2719 can be non-flat structures. In particular, the struts can include a curvature, such as in a concave or convex manner in relationship to the inner diameter of the support structure 2710. The struts can also be twisted. The nonflatness or flatness of the struts can be a property of the material from which they are constructed. For example the struts can exhibit shape-memory or heat responsive changes in shape to the struts during various states. Such states can be defined by the support structure in the compressed or expanded configuration. The struts can also exhibit changes in shape due to stressed on them while implanted. For instance, if used to support a prosthetic valve assembly as described in detail below, the stress on the commissure struts 2719 during the normal cardiac cycle may cause the commissure struts 2719 to permanently or temporarily bend or otherwise change shape. In variations in which the commissure strut members 2719 are fabricated from biocompatible materials having greater flexibility than the materials from which the longitudinal strut members 2711 are fabricated, if a force including a radially inward component is applied to the commissure strut members, they may flex inward, while the longitudinal strut members 2711 may not substantially deform.

Furthermore, the strut members 2711 and 2719 can have a smooth or rough surface texture. In particular, a pitted surface can provide tensile strength to the struts. In addition, roughness or pitting can provide additional friction to help secure the support structure at the implant site and encourage encapsulation of the support structure 2710 by tissue growth to further stabilize and support structure 2710 at the implant site over time.

In certain instances, the support structure 2710 could be comprised of struts that are multiple members stacked upon one another. Within the same stent, some struts could include elongated members stacked upon one another in a multi-ply configuration, and other struts could be one-ply, composed of single-thickness members. Within a single strut, there can be areas of one-ply and multi-ply layering of the members.

Each longitudinal strut member 2711 may also include a plurality of orifices 2713 spaced along the length of strut members 2711. On the front surface 2711*f*, orifices may be countersunk to receive the head of a fastener. The orifices 2713 are shown as being of uniform diameter and uniform spacing along the strut members 2711, but neither is required. FIG. 27A shows commissure strut members 2719 as not having orifices 2713 along their lengths. However, in other instances the commissure strut members 2719 can have orifices 2713 along their lengths. Orifices 2713 on commissure strut members 2719 can similarly be countersunk on front surface 2719f to receive the head of a fastener. Orifices 2713 on commissure strut members 2719 can also similarly be of uniform diameter and uniform spacing along strut members 2719, but again neither is required. The orifices 2713 can receive fasteners as described in detail below, and then can provide an additional pathway for tissue growth-over to stabilize and encapsulate support structure 2710 over time. In FIG. 27A, longitudinal strut members 2711 have five orifices 2713. There can, however, be more or fewer orifices on longitudinal strut members 2711. For example, in another embodiment, longitudinal struts 2711-2, 2711-3 may have four orifices 2713, and longitudinal struts 2711-1, 2711-4 may have no orifices. In another embodiment, longitudinal struts 2711-2, 2711-3 may have no orifices, and longitudinal struts 2711-1, 2711-4 may have four orifices 2713.

The strut members 2711 and 2719 may be arranged as a chain of three six-strut elements. Each six-strut element may contain two outer strut members 2711-1, 2711-3, which overlap two inner strut members 2711-2, 2711-4, with their back surfaces in communication with each other. In addition, each inner and outer strut member may be connected to one of two commissure strut members—outer commissure strut member 2719-1 or inner commissure strut member 2719-2. The strut members 2711, 2719 may be interconnected by rotatable pivot fasteners 2725, such as rivets, extending through aligned orifices. It should be understood that other rotatable fasteners 2725 can be employed such as screws, bolts, ball-in-socket structures, nails, or eyelets, and that the fasteners can be integrally formed in the struts 2711, 2719 such as a peened semi-sphere interacting with an indentation or orifice, or a male-female coupling.

In particular, the outer strut member 2711-1 may be rotatably connected to the inner strut member 2711-2 by a distal pin joint 2715-2 using rivet 2725-2, located near the distal ends of the strut members 2711-1, 2711-2. The outer strut member 2711-3 may be rotatably connected to the inner strut member 2711-4 by a distal pin joint 2715-3 using rivet 2725-3, located near the distal ends of the strut members 2711-3, 2711-4. The outer strut member 2711-3 may also be rotatably connected to the inner strut member 2711-2 by a pin joint 2715-1 using a rivet 2725-1, which utilizes orifices 2713. The pin joint may be offset distally from the longitudinal center on both outer strut member 2711-3 and inner strut member 2711-2. It should be understood that the joint 2715-1 may utilize different orifices 2713 than the ones shown in FIG. 27A, including being offset proximally from the longitudinal center.

The commissure strut member 2719-1 may be rotatably connected at its proximal end to outer strut member 2711-1 and inner strut member 2711-2 at pin joint 2715-2 using rivet 2725-2. The commissure strut member 2719-2 may be rotatably connected at its proximal end to outer strut member 2711-3 and inner strut member 2711-4 at pin joint 2715-3 using rivet 2725-3.

Commissure strut member 2719-1 may be rotatably connected to commissure strut member 2719-2 by a distal anchor pin joint 2715-4 using rivet 2725-4, located near the distal ends of the commissure strut members 2719-1, 2719-2.

Strut members 2711, 2719 may have lengths chosen based on the implant site. In a particular embodiment, longitudinal strut members 2711 may all have approximately the same length, and commissure strut members 2719 may all have approximately the same length. In the variation shown in FIG. 27A, the commissure strut members 2719 have a shorter length than longitudinal strut members 2719. In other variations, the commissure strut members 2719 may be longer than longitudinal strut members 2719. In one embodiment longitudinal strut members 2711 may be about 0.25-3 inches long, and commissure strut members 2719 may be about 0.25-2 inches long. More particularly, longitudinal strut members 2711 may be about 1.75 inches long, and commissure strut members 2719 may be about 1 inch long.

To reduce stress on the anchor rivets 2525-4, 2525-5, and 2525-6, the proximal ends of longitudinal strut members 2711 and distal ends of commissure strut members 2719 can be curved or twisted to provide a flush interface between the joined struts.

As can be seen, the support structure 2710 may be fabricated by linking together a chain of three six-strut elements, and wherein at least some, if not all, of the linkage sets share common struts with adjacent linkages and configuration changes to one linkage will generate complementary changes to the other linkages linked by common struts. Complementary changes, however, are not necessarily limited to linkages or struts with common struts. Two such elements may be connected by rotatably connecting the outer strut member 2711-1 of a first element to the inner strut member 2711-2 of a second element by a proximal anchor pin joint 2715-5 using rivet 2715-5, located near the proximal ends of strut member 2711-1 of the first element and strut member 2711-2 of a second element. In addition, the outer strut member 2711-3 of the first element may be rotatably connected to the inner strut member 2711-4 of the second element by a proximal anchor pin joint 2715-6 using rivet 2725-6, located near the proximal ends of strut member 2711-3 of the first element and strut member 2711-4 of the second element. Outer strut member 2711-1 of the first element may also be rotatably connected to inner strut member 2711-4 of the second element by a pin joint 2715-7 using rivet 2725-7, which utilizes orifices 2713. The pin joint may be offset proximally from the longitudinal center on both the outer strut member 2711-1 and inner strut member 2711-4. It should be understood that joint 2715-7 may utilize different orifices 2713 than the ones shown in FIG. 27A, including being offset distally from the longitudinal center. A third element may be connected to the second element in the same manner as the second element is connected to the first element. The chain may then be wrapped to join the third element with the first element in the same manner.

When the support structure 2710 is in neither a fully expanded nor fully compressed state, the angles between the commissure strut members 2719-1, 2719-2 at distal anchor pin joint 2715-4 may be less than the angle between two longitudinal strut members 2711 at other anchor pin joints 2715-2, 2715-3, 2715-5, and 2715-6. In the embodiment in FIG. 27A the angles between two longitudinal strut members 2711 at anchor pin joints 2715-2, 2715-3, 2715-5, and 2715-6 are the same. In other embodiments the angles may be different. The diameter of support structure 2710 can be chosen based on the implant site. In a particular embodiment for implantation at the mitral valve opening, the diameter may be about 0.5-1.5 inches. More particularly, the diameter may be about 0.8 inches. In another embodiment for implantation at the aortic valve opening, the diameter may be larger than the diameter of an embodiment for implantation at the mitral valve opening. More particularly, the diameter may be about 0.5-2.0 inches. In a particular embodiment, the diameter may be about 1 inch. The diameter may be such that the valve is secured in the aortic valve opening by exerting a strong outward radial force against the tissue, forming a friction fit.

In an embodiment at the aortic valve opening, the overall height of the valve support structure may be less, than the overall height of an embodiment for implantation at the mitral valve. In an embodiment the height in the expanded configuration may be about 0.2-2.0 inches. More particularly, the height in the expanded configuration may be about 0.6 inches.

The support structure 2710 may be collapsible and may be able to be reversibly expanded or compressed by actuating the linkages to open or close the links. When radially inward pressure is applied to one or more longitudinal struts 2711, the support structure 2710 may compress. When radially outward pressure is applied to one or more longitudinal struts 2711, the support structure 2710 may expand.

Figure 27B:
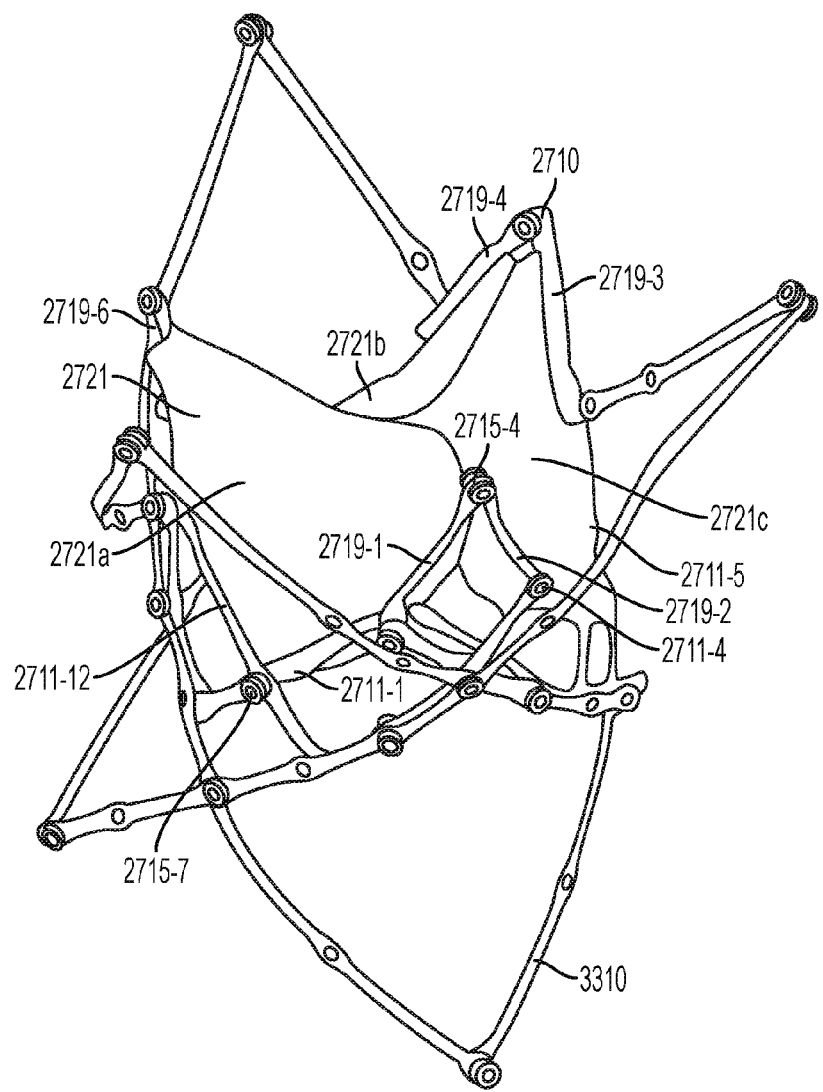
FIG. 27B is the structure of FIG. 27A with a tissue valve mounted to the structure in combination with the support structure in FIG. 33.

In another embodiment, a tissue valve 2721 may be mounted to the support structure 2710 in a secure, sutureless manner, as shown in FIG. 27B. The orientation of attached leaflets may bias the tissue valve 2721 closed. FIG. 27B shows the support structure of FIG. 27A (2710) with tissue valve 2721 attached to the structure of FIG. 33 (3310), which is described in more detail below. Leaflets 2721a, 2721b, 2721c may be suturelessly attached to the support structure 2710 along commissures 2719 and along the distal portion of struts 2711. The sutureless attachments may be formed by sandwiching the leaflets within multi-ply struts making up struts 2711, 2719. More particularly, one side of leaflet 2721a may be sandwiched within multi-ply struts making up commissure strut 2719-1 and the distal portion (the portion distal to joint 2715-7) of longitudinal strut 2711-1; and the other side of leaflet 2721a may be sandwiched within multi-ply struts making up commissure strut 2719-6 and the distal portion of longitudinal strut 2711-12. One side of leaflet 2721b may be suturelessly attached to commissure strut 2719-5 (not shown) and the distal portion of longitudinal strut 2711-9 (not shown); and the other side of leaflet 2721b may be suturelessly attached to commissure strut 2719-4 and the distal portion of longitudinal strut 2711-8 (not shown). One side of leaflet 2721c may be sandwiched within multi-ply struts making up commissure strut 2719-3 and the distal portion of longitudinal strut 2711-5; and the other side of leaflet 2721c may be suturelessly attached to commissure strut 2719-2 and the distal portion of longitudinal strut 2711-4.

In order to facilitate secure, suture-free leaflet attachment during fabrication through sandwiching of the leaflets between the struts, the leaflets 2721 may comprise a shape as shown in FIG. 34 having a central region 3401 having a semicircular or paraboloid shape, with two rectangular tabs extending from each side of the central region 3401. The upper rectangular tabs 3403 may be sandwiched within multi-ply struts making up commissure struts 2719, and the lower rectangular tabs 3405 may be sandwiched within multi-ply struts making up longitudinal struts 2711. After the upper tabs 3403 and lower tabs 3405 are sandwiched between the struts, the portions of the tabs 3403, 3405 may be removed, leaving the central region 3401 suturelessly attached to the support structure 2710. In another variation, the adjacent rectangular tabs 3403, 3405 may be attached to each other.

The support structure 2710 with attached leaflets 2721a, 2721b, 2721c may be collapsible and may be able to be reversibly expanded or compressed by actuating the linkages to open or close the links. When radially inward pressure is applied to the longitudinal struts 2711, the support structure 2710 may collapse into a narrow profile.

Figure 16:
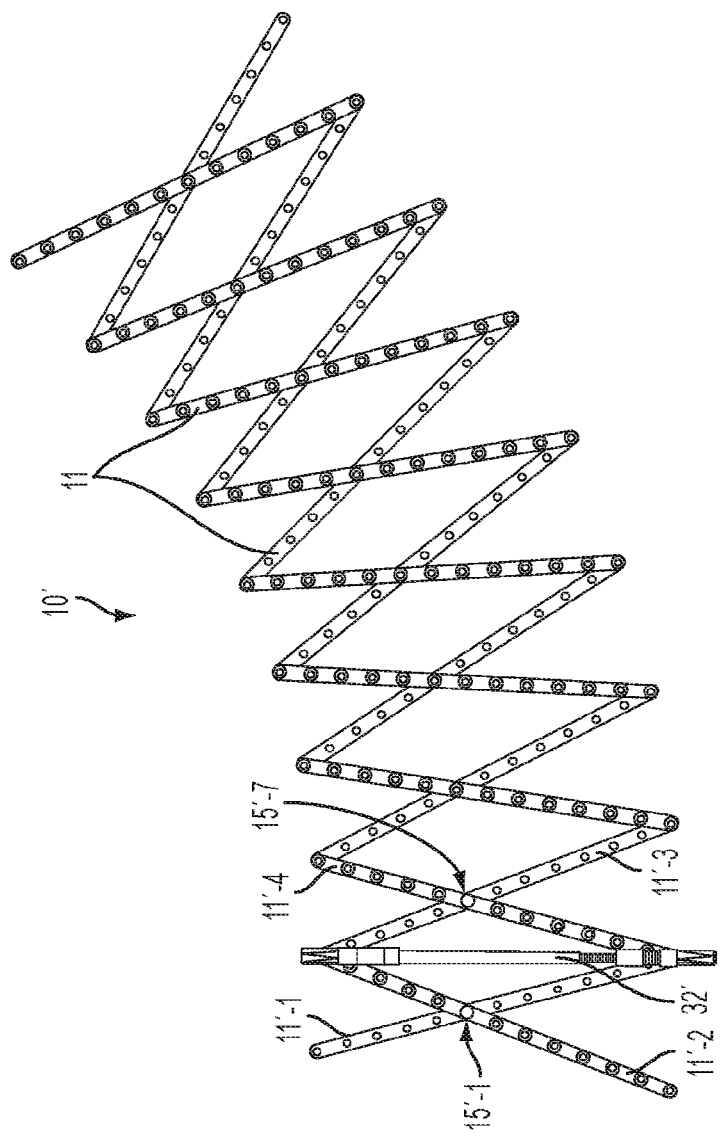
FIG. 16 is a perspective view of the arrangement of strut members in a conical-shaped support structure configuration.

FIG. 16 is a perspective view of the arrangement of strut members in a conical-shaped support structure configuration. In the conical structure 10', the strut members 11 may be arranged as shown in FIG. 2, except that the middle scissor pivots may not bisect the struts. In particular, the middle scissor pivots (e.g. 15'-1, 15'-7) may divide the joined strut members (e.g. 11'-1, 11'-2 and 11'-3, 11'4) into unequal segments of 5/12 and 7/12 lengths. When fully assembled, the resulting support structure may thus conform to a conical shape when expanded. For illustration purposes, the stent 10' is shown with a single-threaded actuator rod 32' (FIG. 6), but it is not a required element for this stent embodiment.

The stent 10' can also assume a cone shape in its expanded configuration by imposing a convex or concave curvature to the individual strut members 11 that comprise the stent 10'. This could be achieved by using a material with memory, such as shape-memory or temperature sensitive Nitinol.

A valve can be orientated in the cone-shaped stent 10' such that the base of the valve was either in the narrower portion of the cone-shaped stent, with the nonbase portion of the valve in the wider portion of the cone. Alternatively, the base of the valve can be located in the widest portion of the stent with the non-base portion of the valve in the less-wide portion of the stent.

The orientation of a cone-shaped stent 10' in the body can be either towards or away from the stream of blood flow. In other body lumens (e.g. respiratory tract or gastrointestinal tract), the stent could be orientated in either direction, in relationship to the axial plane.

Figure 17:
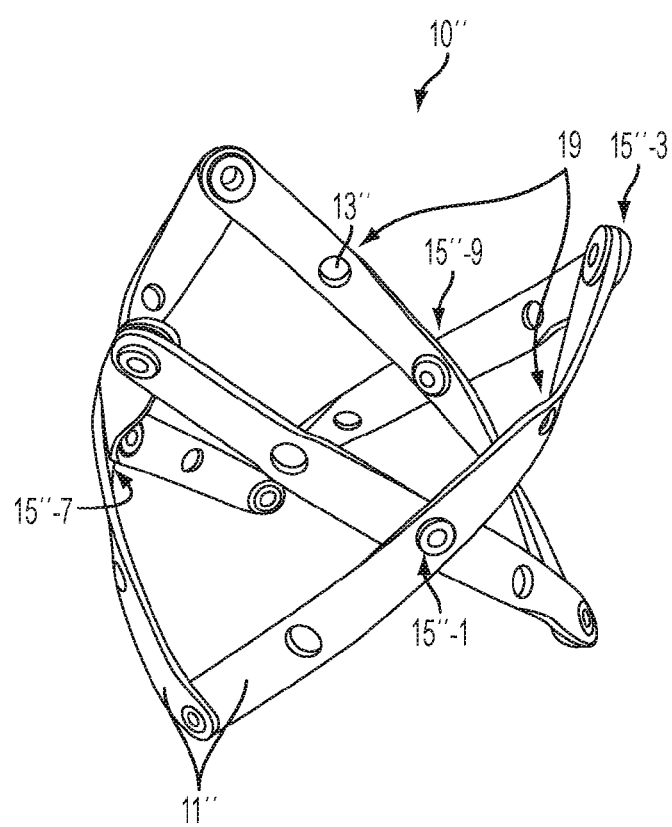
FIG. 17 is a perspective view of an hourglass-shaped support structure configuration.

FIG. 17 is a perspective view of an hourglass-shaped support structure configuration. In this configuration, the circumference around the middle pivot points 15"-1, 15"-7, 15"-9 (the waist) may be less than the circumference at either end of the stent 10". As shown, the hourglass shaped support structure 10" is achieved by reducing the number of strut members 11" to six and shortening the strut members 11" in comparison to prior embodiments. As a result of the shortening, there may be fewer orifices 13" per strut member 11". Because of the strut number and geometry, each strut member 11" may include a twist at points 19" along there longitudinal planes. The twists may provide a flush interface between joined strut 15"-3.

An hourglass stent configuration could also be achieved by imposing concave or convex curvatures in individual bars 11". The curvature could be a property of the materials (e.g. shape-memory or heat-sensitive Nitinol). The curvature could be absent in the compressed stent state and appear when the stent is in its expanded state.

Figure 29A:
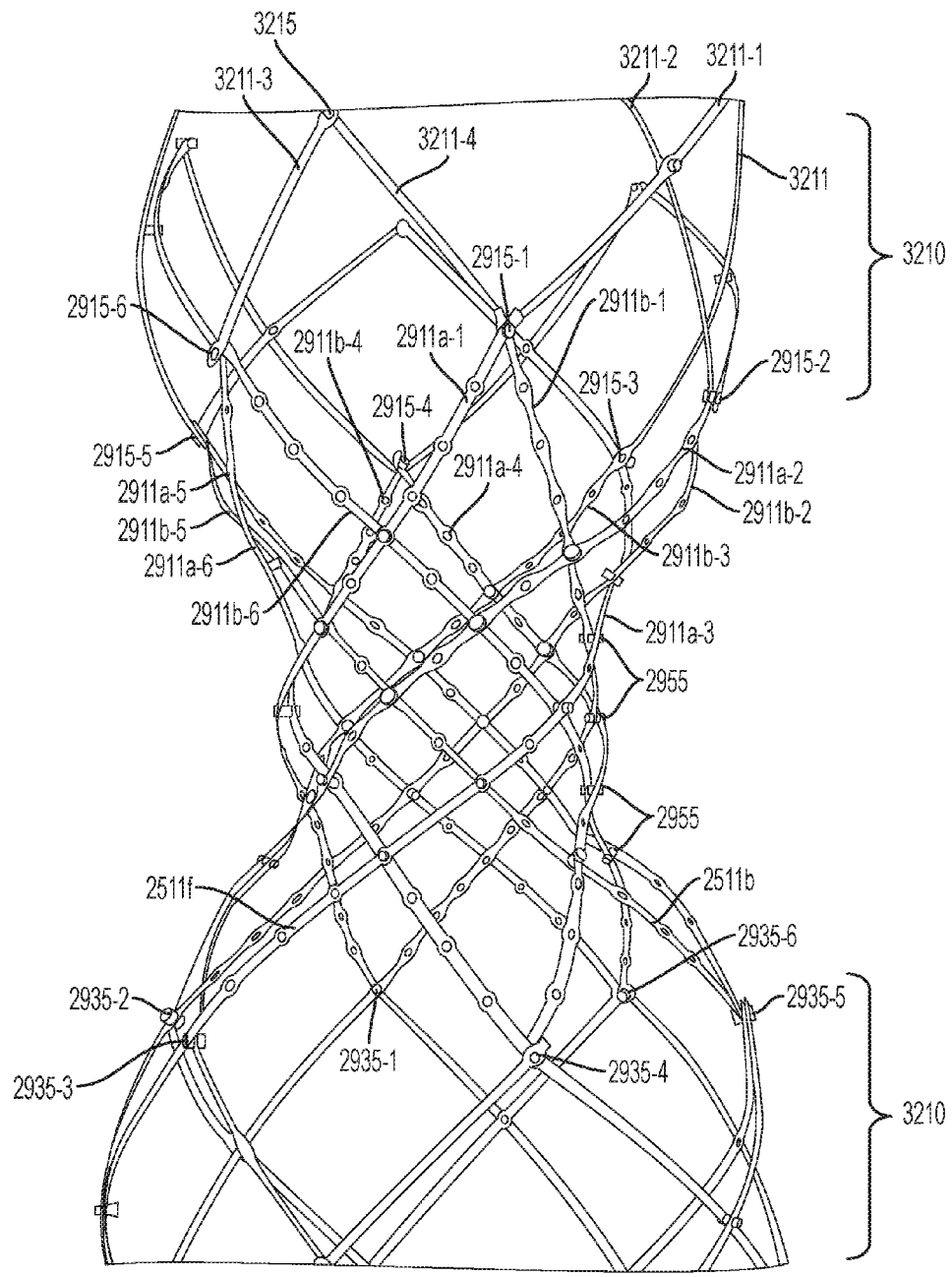
FIG. 29A depicts an hourglass securing support structure with attached deployment structure.

FIG. 29A is another expandable hourglass-shaped securing structure configuration. Hourglass structure 2910 may have a proximal opening 2920, distal opening 2930, and a lumen 2940 therebetween (not indicated). Near the proximal opening 2920 the hourglass structure 2910 may have a proximal tapered section 2950. Near the distal opening 2930 the hourglass structure 2910 may have a distal tapered section 2960. Between the proximal tapered section 2950 and distal tapered section 2960, near the longitudinal middle of the hourglass structure 2910, may be a narrow section 2970 whose diameter may be smaller than the diameters of proximal tapered section 2950 and distal tapered section 2960. As shown, the securing structure 2910 may include a plurality of strut members 2911a, 2911b interconnected by a plurality of pin joints 2915. The strut members 2911a, 2911b may comprise a curved or helical configuration that span the general length of the hourglass structure, wherein each strut may comprise a proximal and distal region with a relatively wider curvature, and a middle region with a relatively tighter curvature. The helical configuration of the struts may be right or left-handed, as described in greater detail below. The curvatures of the proximal and distal region may or may not be the same. In particular, the pin joints 15 may allow the interconnected strut members 2911 to rotate relative to each other. The pin joints may have an axis of rotation with a radial orientation. As shown there are six strut members 2911a and six strut members 2911b. However, in other variations the hourglass structure 2910 may have other numbers of strut members. For instance, in one variation the hourglass structure 2910 may have three strut members 2911*a* and three strut members 2911*b*.

Hourglass structure 2910 may be configured such that it can act as a securing body to be secured within a location within the body. In particular, structure 2910 can be configured to be placed near the location of the mitral valve in the heart, with the narrow section 2970 in the location of the mitral valve opening, proximal tapered section 2950 located in the left atrium, and distal tapered section 2960 located in the left ventricle. In a particular embodiment for implantation at the mitral valve opening, the diameter at the narrow section 2970 may be about 0.5-1.5 inches. More particularly, the diameter may be about 0.8 inches. The diameter at the proximal tapered section 2950 may be about 1-3 inches. More particularly, the diameter may be about 1.75 inches. The diameter at the distal tapered section 2960 may be about 1-3 inches. More particularly, the diameter may be about 1.75 inches. This hourglass configuration may allow the structure to be secured in the mitral valve opening without requiring a strong outward force to hold the structure in place.

As shown in FIG. 29A, deployment structure 3210 may also be attached to the proximal and/or distal ends of the hourglass structure 2910. In the variation in FIG. 29A, deployment structures 3210 may be connected to both the proximal and distal ends of hourglass structure 2910, and their ends may deflect outward from the proximal and distal ends of hourglass structure 2910. Deployment structure 3210 may comprise a serial chain of scissor mechanisms comprising a plurality of longitudinal strut members 3211 rotatably interconnected by a plurality of pin joints 2915. As shown, there are twelve struts 3211. In another variation, hourglass structure 2910 may not have deployment structures 3210 attached to its proximal and distal ends. Hourglass structure 2910 may also have only one deployment structure 3210 that is attached to either its proximal or distal end.

Strut members 2911*a*, 2911*b* and 3211 may be fabricated from a rigid or semi-rigid biocompatible material as described elsewhere herein. In some variations, strut members 3211 of deployment structure 3210 may be fabricated from a biocompatible material having greater flexibility than the materials from which strut members 2911*a*, 2911*b* are fabricated. The greater flexibility may allow the deployment struts 3211 inwardly deflectable. The dimensions of each strut can be chosen in accordance with its desired use. As shown, each longitudinal strut member 2911*a*, 2911*b* has a front surface 2511*f* and a back surface 2511*b*. In a particular embodiment, each strut member may be made from stainless steel, which is about 0.001-0.100 inch thick. More particularly, each strut may be about 0.01 inch thick 300 series stainless steel. In other variations, the deployment struts 3211 may be thinner than the struts 2911*a*, 2911*b*, which may increase flexibility of the deployment struts 3211. While all struts 2911*a*, 2911*b* and 3211 are shown as being of uniform thickness, the thickness of a strut can vary across a strut, such as a gradual increase or decrease in thickness along the length of a strut. Furthermore, individual struts 2911*a*, 2911*b* and 3211 can differ in thickness from other individual struts 2911*a*, 2911*b* and 3211 in the same support structure. In a particular embodiment, each strut member 2911*a*, 2911*b* and 3211 may be about 0.01-0.25 inches wide. More particularly, each strut 2911*a*, 2911*b* and 3211 may be about 0.06 inches wide. While all struts 2911*a*, 2911*b* and 3211 are shown as being of a uniform width, a strut can vary in width along its length. Furthermore, an individual strut 2911*a*, 2911*b* and 3211 can have a different width than another strut 2911*a*, 2911*b* and 3211 in the same support structure. The particular dimensions can be chosen based on the implant site. The strut lengths can vary from strut to strut within the same support structure, as is explained in detail below.

Each of strut members 2911*a*, 2911*b* may have a helical shape with the helical axis aligned with the central axis of the securing structure 2910. Strut members 2911*a* may be right-handed helices, and strut members 2911*b* may be left-handed helices. The diameter of the helical shape may also vary along the length of the strut members such that the circumferences at the longitudinal center of the strut members 2911*a*, 2911*b* may be less than the circumferences at the proximal and distal ends of the strut members 2911*a*, 2911*b*. The nonflatness or flatness of the struts can be a property of the material from which they are constructed. For example, the struts can exhibit shape-memory or heat-responsive changes in shape to the struts during various states. Such states can be defined by the stent in the compressed or expanded configuration.

As shown, each strut member 3211 is bar shaped. The strut members can however be of different geometries. For example, instead of a uniform width, a strut 3211 can vary in width along its length. Furthermore, an individual strut 3211 can have a different width than another strut in the same deployment structure. Similarly, the strut lengths can vary from strut to strut within the same deployment structure. The particular dimensions can be chosen based on the implant site. Furthermore, the struts 3211 can be non-flat structures. In particular, the struts 3211 can include a curvature, such as in a concave, as in FIG. 29A, or convex manner in relationship to the inner diameter of the deployment structure. The struts 3211 can also be twisted. The nonflatness or flatness of the struts 3211 can be a property of the material from which they are constructed. For example, the struts 3211 can exhibit shape-memory or heat-responsive changes in shape to the struts during various states. Such states can be defined by the deployment structure in the compressed or expanded configuration.

Furthermore, the strut members 2911*a*, 2911*b* and 3211 can have a smooth or rough surface texture. In particular, a pitted surface can provide tensile strength to the struts. In addition, roughness or pitting can provide additional friction to help secure the support structure at the implant site and encourage encapsulation of the securing structure 2910 and deployment structure 3210 by tissue growth to further stabilize and securing structure 2910 at the implant site over time.

In certain instances, the securing structure 2910 and deployment structure 3210 could be comprised of struts that are multiple members stacked upon one another. Within the same stent, some struts could include elongated members stacked upon one another in a multi-ply configuration, and other struts could be one-ply, composed of single-thickness members. Within a single strut, there can be areas of one-ply and multi-ply layering of the members.

Each strut member 2911*a*, 2911*b* may also include a plurality of orifices 2913 spaced along the length of the strut member 2911*a* or 2911*b*. On the front surface, the orifices may be countersunk 2917 to receive the head of a fastener. In a particular embodiment, there may be seventeen equally spaced orifices 2913 along the length of each strut member 2911*a*, 2911*b*, but more or fewer orifices can be used. The orifices 2913 are shown as being of uniform diameter and uniform spacing along the strut member 2911*a* or 2911*b*, but neither is required. FIG. 29A shows deployment structure 3210 strut members 3211 as not having orifices 2513 along their lengths. However, in other instances the strut members 3211 can have orifices 2513 along their lengths.

The strut members 2911*a*, 2911*b* may be arranged such that the helical axes of all strut members 2911*a*, 2911*b* are aligned and are interconnected by rotatable pivot fasteners 2925, such as rivets, extending through aligned orifices 2913. It should be understood that other rotatable fasteners 2925 can be employed such as screws, bolts, ball-in socket structures, nails, or eyelets, and that the fasteners can be integrally formed in the struts 11 such as a peened semi-sphere interacting with an indentation of orifice, or a male-female coupling. In addition to receiving a fastener, the orifices 2913 also provide an additional pathway for tissue growth-over to stabilize and encapsulate the securing structure 2910 over time.

As shown in FIG. 29A, each right-handed helical strut member 2911*a* is an outer strut member. Each left-handed helical strut member 2911*b* is an inner strut member. Each outer, right-handed individual strut member 2911*a* may be rotatably connected to an individual inner, left-handed strut member 2911*b* strut member, with their back surfaces in oriented toward each other.

In particular, each outer, right-handed strut member 2911*a* may be rotatably connected to an inner, left-handed strut member 2911*b* by a distal anchor pin joint 2915 by rivet 2925, located near the distal ends of the strut members 2911*a*, 2911*b*, and a proximal anchor pin joint 2935 by rivet 2945, located near the proximal ends of the strut members 2911*a*, 2911*b*. Each outer, right-handed strut member 2911*a* may also be rotatably connected to each of the five remaining inner, left-handed strut members 2911*b* via a scissor pin joint 2955.

More specifically, outer, right-handed strut member 2911*a*-1 may be rotatably connected to inner, left-handed strut member 2911*b*-1 by a distal anchor pin joint 2915-1 by rivet 2925-1 (not shown), located near the distal ends of the strut members 2911*a*-1, 2911*b*-1. Outer, right-handed strut member 2911*a*-1 may also be rotatably connected to inner, left-handed strut member 2911*b*-1 by a proximal anchor pin joint 2935-1 by rivet 2945-1 (not shown), located near the distal ends of the strut members 2911*a*-1, 2911*b*-1.

In addition, proximal to pin joint 2915-1, outer, right-handed strut member 2911*a*-1 may be rotatably connected via scissor pin joint 2955 to inner, left-handed strut member 2911*b*-6. Proximal to its connection with strut member 2911*b*-6, strut member 2911*a*-1 may be rotatably connected via scissor pin joint 2955 to inner, left-handed strut member 2911*b*-5. Proximal to its connection with strut member 2911*b*-5, strut member 2911*a*-1 may be rotatably connected via scissor pin joint 2955 to inner, left-handed strut member 2911*b*-4. Proximal to its connection with strut member 2911*b*-4, strut member 2911*a*-1 may be rotatably connected via scissor pin joint 2955 to inner, left-handed strut member 2911*b*-3. Proximal to its connection with strut member 2911*b*-3, strut member 2911*a*-1 may be rotatably connected via scissor pin joint 2955 to inner, left-handed strut member 2911*b*-2. Proximal to the connection between strut members 2911*a*-1 and 2911*b*-2 may be the proximal anchor pin joint 2935-1. Each scissor pin joint 2955 described above may be separated longitudinally from each other pin joint 2955 along strut member 2911*a*-1 by one open orifice 2913. Distal pin joint 2915-1 may be separated longitudinally along strut member 2911*a*-1 from the scissor pin joint between strut members 2911*a*-1 and 2911*b*-6 by three open orifices 2913. Proximal pin joint 2935-1 may be separated longitudinally along strut member 2911*a*-1 from the scissor pin joint between strut members 2911*a*-1 and 2911*b*-2 by three open orifices 2913.

In addition, proximal to pin joint 2915-1, inner, left-handed strut member 2911*b*-1 may be rotatably connected via scissor pin joint 2955 to outer, right-handed strut member 2911*a*-2. Proximal to its connection with strut member 2911*a*-2, strut member 2911*b*-1 may be rotatably connected via scissor pin joint 2955 to outer, right-handed strut member 2911*a*-3. Proximal to its connection with strut member 2911*a*-3, strut member 2911*b*-1 may be rotatably connected via scissor pin joint 2955 to outer, right-handed strut member 2911*a*-4. Proximal to its connection with strut member 2911*a*-4, strut member 2911*b*-1 may be rotatably connected via scissor pin joint 2955 to outer, right-handed strut member 2911*a*-5. Proximal to its connection with strut member 2911*a*-5, strut member 2911*b*-1 may be rotatably connected via scissor pin joint 2955 to outer, right-handed strut member 2911*a*-6. Proximal to the connection between strut members 2911*b*-1 and 2911*a*-6 may be the proximal anchor pin joint 2935-1. Each scissor pin joint 2955 described above may be separated longitudinally from each other pin joint 2955 along strut member 2911*b*-1 by one open orifice 2913. Distal pin joint 2915-1 may be separated longitudinally along strut member 2911*b*-1 from the scissor pin joint between strut members 2911*b*-1 and 2911*a*-2 by three open orifices 2913. Proximal pin joint 2935-1 may be separated longitudinally along strut member 2911*b*-1 from the scissor pin joint between strut members 2911*b*-1 and 2911*a*-6 by three open orifices 2913. It should be noted that the spacings shown in FIG. 29A are not required; spacing may be by more or fewer orifices.

Similar patterns of articulations exist between the remaining outer, right-handed strut members 2911*a* and inner, left-handed strut members 2911*b*. More specifically, outer, right-handed strut member 2911*a*-2 may be rotatably connected to inner, left-handed strut member 2911*b*-2 by a distal anchor pin joint 2915-2 by rivet 2925-2 (not shown), located near the distal ends of the strut members 2911*a*-2, 2911*b*-2. Outer, right-handed strut member 2911*a*-2 may also be rotatably connected to inner, left-handed strut member 2911*b*-2 by a proximal anchor pin joint 2935-2 by rivet 2945-2 (not shown), located near the distal ends of the strut members 2911*a*-2, 2911*b*-2.

In addition, proximal to pin joint 2915-2, outer, right-handed strut member 2911*a*-2 may be rotatably connected via scissor pin joint 2955 to inner, left-handed strut member 2911*b*-1. Proximal to its connection with strut member 2911*b*-1, strut member 2911*a*-2 may be rotatably connected via scissor pin joint 2955 to inner, left-handed strut member 2911*b*-6. Proximal to its connection with strut member 2911*b*-6, strut member 2911*a*-2 may be rotatably connected via scissor pin joint 2955 to inner, left-handed strut member 2911*b*-5. Proximal to its connection with strut member 2911*b*-5, strut member 2911*a*-2 may be rotatably connected via scissor pin joint 2955 to inner, left-handed strut member 2911*b*-4. Proximal to its connection with strut member 2911*b*-4, strut member 2911*a*-2 may be rotatably connected via scissor pin joint 2955 to inner, left-handed strut member 2911*b*-3. Proximal to the connection between strut members 2911*a*-2 and 2911*b*-3 may be the proximal anchor pin joint 2935-2. Each scissor pin joint 2955 described above may be separated longitudinally from each other pin joint 2955 along strut member 2911*a*-2 by one open orifice 2913. Distal pin joint 2915-2 may be separated longitudinally along strut member 2911*a*-2 from the scissor pin joint between strut members 2911*a*-2 and 2911*b*-1 by three open orifices 2913. Proximal pin joint 2935-2 may be separated longitudinally along strut member 2911*a*-2 from the scissor pin joint between strut members 2911*a*-2 and 2911*b*-3 by three open orifices 2913.

In addition, proximal to pin joint 2915-2, inner, left-handed strut member 2911*b*-2 may be rotatably connected via scissor pin joint 2955 to outer, right-handed strut member 2911a-3. Proximal to its connection with strut member 2911a-3, strut member 2911b-2 may be rotatably connected via scissor pin joint 2955 to outer, right-handed strut member 2911a-4. Proximal to its connection with strut member 2911a-4, strut member 2911b-2 may be rotatably connected via scissor pin joint 2955 to outer, right-handed strut member 2911a-5. Proximal to its connection with strut member 2911a-5, strut member 2911b-2 may be rotatably connected via scissor pin joint 2955 to outer, right-handed strut member 2911a-6. Proximal to its connection with strut member 2911a-6, strut member 2911b-2 may be rotatably connected via scissor pin joint 2955 to outer, right-handed strut member 2911a-1. Proximal to the connection between strut members 2911b-2 and 2911a-1 may be the proximal anchor pin joint 2935-2. Each scissor pin joint 2955 described above may be separated longitudinally from each other pin joint 2955 along strut member 2911b-2 by one open orifice 2913. Distal pin joint 2915-2 may be separated longitudinally along strut member 2911b-2 from the scissor pin joint between strut members 2911b-2 and 2911a-3 by three open orifices 2913. Proximal pin joint 2935-2 may be separated longitudinally along strut member 2911b-2 from the scissor pin joint between strut members 2911b-2 and 2911a-1 by three open orifices 2913. It should be noted that the spacings shown in FIG. 29A are not required; spacing may be by more or fewer orifices.

Outer, right-handed strut member 2911a-3 may be rotatably connected to inner, left-handed strut member 2911b-3 by a distal anchor pin joint 2915-3 by rivet 2925-3 (not shown), located near the distal ends of the strut members 2911a-3, 2911b-3. Outer, right-handed strut member 2911a-3 may also be rotatably connected to inner, left-handed strut member 2911b-3 by a proximal anchor pin joint 2935-3 by rivet 2945-3 (not shown), located near the distal ends of the strut members 2911a-3, 2911b-3.

In addition, proximal to pin joint 2915-3, outer, right-handed strut member 2911a-3 may be rotatably connected via scissor pin joint 2955 to inner, left-handed strut member 2911b-2. Proximal to its connection with strut member 2911b-2, strut member 2911a-3 may be rotatably connected via scissor pin joint 2955 to inner, left-handed strut member 2911b-1. Proximal to its connection with strut member 2911b-1, strut member 2911a-3 may be rotatably connected via scissor pin joint 2955 to inner, left-handed strut member 2911b-6. Proximal to its connection with strut member 2911b-6, strut member 2911a-3 may be rotatably connected via scissor pin joint 2955 to inner, left-handed strut member 2911b-5. Proximal to its connection with strut member 2911b-5, strut member 2911a-3 may be rotatably connected via scissor pin joint 2955 to inner, left-handed strut member 2911b-4. Proximal to the connection between strut members 2911a-3 and 2911b-4 may be the proximal anchor pin joint 2935-3. Each scissor pin joint 2955 described above may be separated longitudinally from each other pin joint 2955 along strut member 2911a-3 by one open orifice 2913. Distal pin joint 2915-3 may be separated longitudinally along strut member 2911a-3 from the scissor pin joint between strut members 2911a-3 and 2911b-2 by three open orifices 2913. Proximal pin joint 2935-3 may be separated longitudinally along strut member 2911a-3 from the scissor pin joint between strut members 2911a-3 and 2911b-4 by three open orifices 2913.

In addition, proximal to pin joint 2915-3, inner, left-handed strut member 2911b-3 may be rotatably connected via scissor pin joint 2955 to outer, right-handed strut member 2911a-4. Proximal to its connection with strut member 2911a-4, strut member 2911b-3 may be rotatably connected via scissor pin joint 2955 to outer, right-handed strut member 2911a-5. Proximal to its connection with strut member 2911a-5, strut member 2911b-3 may be rotatably connected via scissor pin joint 2955 to outer, right-handed strut member 2911a-6. Proximal to its connection with strut member 2911a-6, strut member 2911b-3 may be rotatably connected via scissor pin joint 2955 to outer, right-handed strut member 2911a-1. Proximal to its connection with strut member 2911a-1, strut member 2911b-3 may be rotatably connected via scissor pin joint 2955 to outer, right-handed strut member 2911a-2. Proximal to the connection between strut members 2911b-3 and 2911a-2 may be the proximal anchor pin joint 2935-3. Each scissor pin joint 2955 described above may be separated longitudinally from each other pin joint 2955 along strut member 2911b-3 by one open orifice 2913. Distal pin joint 2915-3 may be separated longitudinally along strut member 2911b-3 from the scissor pin joint between strut members 2911b-3 and 2911a-4 by three open orifices 2913. Proximal pin joint 2935-3 may be separated longitudinally along strut member 2911b-3 from the scissor pin joint between strut members 2911b-3 and 2911a-2 by three open orifices 2913. It should be noted that the spacings shown in FIG. 29A are not required; spacing may be by more or fewer orifices.

Outer, right-handed strut member 2911a-4 may be rotatably connected to inner, left-handed strut member 2911b-4 by a distal anchor pin joint 2915-4 by rivet 2925-4 (not shown), located near the distal ends of the strut members 2911a-4, 2911b-4. Outer, right-handed strut member 2911a-4 may also be rotatably connected to inner, left-handed strut member 2911b-4 by a proximal anchor pin joint 2935-4 by rivet 2945-4 (not shown), located near the distal ends of the strut members 2911a-4, 2911b-4.

In addition, proximal to pin joint 2915-4, outer, right-handed strut member 2911a-4 may be rotatably connected via scissor pin joint 2955 to inner, left-handed strut member 2911b-3. Proximal to its connection with strut member 2911b-3, strut member 2911a-4 may be rotatably connected via scissor pin joint 2955 to inner, left-handed strut member 2911b-2. Proximal to its connection with strut member 2911b-2, strut member 2911a-4 may be rotatably connected via scissor pin joint 2955 to inner, left-handed strut member 2911b-1. Proximal to its connection with strut member 2911b-1, strut member 2911a-4 may be rotatably connected via scissor pin joint 2955 to inner, left-handed strut member 2911b-6. Proximal to its connection with strut member 2911b-6, strut member 2911a-4 may be rotatably connected via scissor pin joint 2955 to inner, left-handed strut member 2911b-5. Proximal to the connection between strut members 2911a-4 and 2911b-5 may be the proximal anchor pin joint 2935-4. Each scissor pin joint 2955 described above may be separated longitudinally from each other pin joint 2955 along strut member 2911a-4 by one open orifice 2913. Distal pin joint 2915-4 may be separated longitudinally along strut member 2911a-4 from the scissor pin joint between strut members 2911a-4 and 2911b-3 by three open orifices 2913. Proximal pin joint 2935-4 may be separated longitudinally along strut member 2911a-4 from the scissor pin joint between strut members 2911a-4 and 2911b-5 by three open orifices 2913.

In addition, proximal to pin joint 2915-4, inner, left-handed strut member 2911b-4 may be rotatably connected via scissor pin joint 2955 to outer, right-handed strut member 2911a-5. Proximal to its connection with strut member 2911a-5, strut member 2911b-4 may be rotatably connected via scissor pin joint 2955 to outer, right-handed strut member 2911a-6. Proximal to its connection with strut member 2911a-6, strut member 2911b-4 may be rotatably connected via scissor pin joint 2955 to outer, right-handed strut member 2911*a*-1. Proximal to its connection with strut member 2911*a*-1, strut member 2911*b*-4 may be rotatably connected via scissor pin joint 2955 to outer, right-handed strut member 2911*a*-2. Proximal to its connection with strut member 2911*a*-2, strut member 2911*b*-4 may be rotatably connected via scissor pin joint 2955 to outer, right-handed strut member 2911*a*-3. Proximal to the connection between strut members 2911*b*-4 and 2911*a*-3 may be the proximal anchor pin joint 2935-4. Each scissor pin joint 2955 described above may be separated longitudinally from each other pin joint 2955 along strut member 2911*b*-4 by one open orifice 2913. Distal pin joint 2915-4 may be separated longitudinally along strut member 2911*b*-4 from the scissor pin joint between strut members 2911*b*-4 and 2911*a*-5 by three open orifices 2913. Proximal pin joint 2935-4 may be separated longitudinally along strut member 2911*b*-4 from the scissor pin joint between strut members 2911*b*-4 and 2911*a*-3 by three open orifices 2913. It should be noted that the spacings shown in FIG. 29A are not required; spacing may be by more or fewer orifices.

Outer, right-handed strut member 2911*a*-5 may be rotatably connected to inner, left-handed strut member 2911*b*-5 by a distal anchor pin joint 2915-5 by rivet 2925-5 (not shown), located near the distal ends of the strut members 2911*a*-5, 2911*b*-5. Outer, right-handed strut member 2911*a*-5 may be also rotatably connected to inner, left-handed strut member 2911*b*-5 by a proximal anchor pin joint 2935-5 by rivet 2945-5 (not shown), located near the distal ends of the strut members 2911*a*-5, 2911*b*-5.

In addition, proximal to pin joint 2915-5, outer, right-handed strut member 2911*a*-5 may be rotatably connected via scissor pin joint 2955 to inner, left-handed strut member 2911*b*-4. Proximal to its connection with strut member 2911*b*-4, strut member 2911*a*-5 may be rotatably connected via scissor pin joint 2955 to inner, left-handed strut member 2911*b*-3. Proximal to its connection with strut member 2911*b*-3, strut member 2911*a*-5 may be rotatably connected via scissor pin joint 2955 to inner, left-handed strut member 2911*b*-2. Proximal to its connection with strut member 2911*b*-2, strut member 2911*a*-5 may be rotatably connected via scissor pin joint 2955 to inner, left-handed strut member 2911*b*-1. Proximal to its connection with strut member 2911*b*-1, strut member 2911*a*-5 may be rotatably connected via scissor pin joint 2955 to inner, left-handed strut member 2911*b*-6. Proximal to the connection between strut members 2911*a*-5 and 2911*b*-6 may be the proximal anchor pin joint 2935-5. Each scissor pin joint 2955 described above may be separated longitudinally from each other pin joint 2955 along strut member 2911*a*-5 by one open orifice 2913. Distal pin joint 2915-5 may be separated longitudinally along strut member 2911*a*-5 from the scissor pin joint between strut members 2911*a*-5 and 2911*b*-4 by three open orifices 2913. Proximal pin joint 2935-5 may be separated longitudinally along strut member 2911*a*-5 from the scissor pin joint between strut members 2911*a*-5 and 2911*b*-6 by three open orifices 2913.

In addition, proximal to pin joint 2915-5, inner, left-handed strut member 2911*b*-5 may be rotatably connected via scissor pin joint 2955 to outer, right-handed strut member 2911*a*-6. Proximal to its connection with strut member 2911*a*-6, strut member 2911*b*-5 may be rotatably connected via scissor pin joint 2955 to outer, right-handed strut member 2911*a*-1. Proximal to its connection with strut member 2911*a*-1, strut member 2911*b*-5 may be rotatably connected via scissor pin joint 2955 to outer, right-handed strut member 2911*a*-2. Proximal to its connection with strut member 2911*a*-2, strut member 2911*b*-5 may be rotatably connected via scissor pin joint 2955 to outer, right-handed strut member 2911*a*-3. Proximal to its connection with strut member 2911*a*-3, strut member 2911*b*-5 may be rotatably connected via scissor pin joint 2955 to outer, right-handed strut member 2911*a*-4. Proximal to the connection between strut members 2911*b*-5 and 2911*a*-4 may be the proximal anchor pin joint 2935-5. Each scissor pin joint 2955 described above may be separated longitudinally from each other pin joint 2955 along strut member 2911*b*-5 by one open orifice 2913. Distal pin joint 2915-5 may be separated longitudinally along strut member 2911*b*-5 from the scissor pin joint between strut members 2911*b*-5 and 2911*a*-6 by three open orifices 2913. Proximal pin joint 2935-5 may be separated longitudinally along strut member 2911*b*-5 from the scissor pin joint between strut members 2911*b*-5 and 2911*a*-4 by three open orifices 2913. It should be noted that the spacings shown in FIG. 29A are not required; spacing may be by more or fewer orifices.

Outer, right-handed strut member 2911*a*-6 may be rotatably connected to inner, left-handed strut member 2911*b*-6 by a distal anchor pin joint 2915-6 by rivet 2925-6 (not shown), located near the distal ends of the strut members 2911*a*-6, 2911*b*-6. Outer, right-handed strut member 2911*a*-6 may also be rotatably connected to inner, left-handed strut member 2911*b*-6 by a proximal anchor pin joint 2935-6 by rivet 2945-6 (not shown), located near the distal ends of the strut members 2911*a*-6, 2911*b*-6.

In addition, proximal to pin joint 2915-6, outer, right-handed strut member 2911*a*-6 may be rotatably connected via scissor pin joint 2955 to inner, left-handed strut member 2911*b*-5. Proximal to its connection with strut member 2911*b*-5, strut member 2911*a*-6 may be rotatably connected via scissor pin joint 2955 to inner, left-handed strut member 2911*b*-4. Proximal to its connection with strut member 2911*b*-4, strut member 2911*a*-6 may be rotatably connected via scissor pin joint 2955 to inner, left-handed strut member 2911*b*-3. Proximal to its connection with strut member 2911*b*-3, strut member 2911*a*-6 may be rotatably connected via scissor pin joint 2955 to inner, left-handed strut member 2911*b*-2. Proximal to its connection with strut member 2911*b*-2, strut member 2911*a*-6 may be rotatably connected via scissor pin joint 2955 to inner, left-handed strut member 2911*b*-1. Proximal to the connection between strut members 2911*a*-6 and 2911*b*-1 may be the proximal anchor pin joint 2935-6. Each scissor pin joint 2955 described above may be separated longitudinally from each other pin joint 2955 along strut member 2911*a*-6 by one open orifice 2913. Distal pin joint 2915-6 may be separated longitudinally along strut member 2911*a*-6 from the scissor pin joint between strut members 2911*a*-6 and 2911*b*-5 by three open orifices 2913. Proximal pin joint 2935-6 may be separated longitudinally along strut member 2911*a*-6 from the scissor pin joint between strut members 2911*a*-6 and 2911*b*-1 by three open orifices 2913.

In addition, proximal to pin joint 2915-6, inner, left-handed strut member 2911*b*-6 may be rotatably connected via scissor pin joint 2955 to outer, right-handed strut member 2911*a*-1. Proximal to its connection with strut member 2911*a*-1, strut member 2911*b*-6 may be rotatably connected via scissor pin joint 2955 to outer, right-handed strut member 2911*a*-2. Proximal to its connection with strut member 2911*a*-2, strut member 2911*b*-6 may be rotatably connected via scissor pin joint 2955 to outer, right-handed strut member 2911*a*-3. Proximal to its connection with strut member 2911*a*-3, strut member 2911*b*-6 may be rotatably connected via scissor pin joint 2955 to outer, right-handed strut member 2911*a*-4. Proximal to its connection with strut member 2911*a*-4, strut member 2911*b*-6 may be rotatably connected via scissor pin joint 2955 to outer, right-handed strut member 2911a-5. Proximal to the connection between strut members 2911b-6 and 2911a-5 may be the proximal anchor pin joint 2935-6. Each scissor pin joint 2955 described above may be separated longitudinally from each other pin joint 2955 along strut member 2911b-6 by one open orifice 2913. Distal pin joint 2915-6 may be separated longitudinally along strut member 2911b-6 from the scissor pin joint between strut members 2911b-6 and 2911a-1 by three open orifices 2913. Proximal pin joint 2935-6 may be separated longitudinally along strut member 2911b-6 from the scissor pin joint between strut members 2911b-6 and 2911a-5 by three open orifices 2913. It should be noted that the spacings shown in FIG. 29A are not required; spacing may be by more or fewer orifices.

Strut members 3211 of deployment structures 3210 are arranged as a chain of four-bar linkages. The strut members 3211 are rotatably interconnected at joints 3215 by rotatable pivot fasteners 3225, such as rivets. It should be understood that other rotatable fasteners 3225 can be employed such as screws, bolts, ball-in-socket structures, nails, or eyelets, and that the fasteners can be integrally formed in the struts 3211 such as a peened semi-sphere interacting with an indentation or orifice, or a male-female coupling.

In each four-bar linkage, two outer strut members 3211 may overlap two inner strut members 3211, with their back surfaces in communication with each other. In particular, first strut member 3211-1 may be rotatably connected to the second strut member 3211-2 by a middle pin joint 3215 using rivet 3225 that bisects the strut members 3211-1, 3211-2. Similarly, the third strut member 3211-3 may be rotatably connected to bisect the four strut member 3211-4 by a middle pin joint 3215 using rivet 3225. As shown, the resulting scissor arms are of equal length. It should also be understood that the scissor arms may be of unequal length.

The second strut member 3211-2 may also be rotatably connected to the third strut member 3211-3 by a distal anchor pin joint 3215, located near the distal ends of the strut members 3211-2, 3211-3. Similarly, the first strut member 3211-1 may be rotatably connected to the fourth strut member 3211-4 by a proximal anchor pin joint 3215 located near the proximal ends of the strut members 3211-1, 3211-4. The curved shape of struts 3211 may reduce the stresses on the anchor rivets 3225 by providing a flush interface between the joined struts.

As can be seen, the deployment structure 3210 may be fabricated by linking together a serial chain of scissor mechanisms. The chain may then be wrapped to join the last scissor mechanism with the first scissor mechanism in the chain. The diameter of deployment structure 3210 may be approximately the same as the diameter of the proximal tapered section 2950 of hourglass structure 2910 or the distal tapered section 2960 of hourglass structure 2910. The deployment structure 3210 may be rotatably attached to the hourglass structure 2910 at the distal or proximal anchor pin joints 3215 of deployment structure 3210 and the proximal anchor pin joints 2935 or distal anchor pin joints 2915 of hourglass structure 2910. In another embodiment, the strut members 3211 of deployment structure 3210 may extend along the distal and proximal strut portions of helical struts 2911 of hourglass securing structure 2910, overlapping with the distal and proximal portions of helical struts 2911. In such an embodiment, the overlapping of the strut members 3211 with the distal and proximal portions of helical struts 2911 may allow greater flexibility in the deployment structure.

The hourglass structure 2910 can be expanded or compressed by actuating the linkages to open or close the links. The deployment structure 3210 can also be expanded or compressed by actuating the linkages to open or close the links. When deployment structure 3210 is attached to hourglass structure 2910, the attachment may be such that by actuating the linkages on either hourglass structure 2910 or deployment structure 3210, the combination is expanded or compressed.

Figure 33:
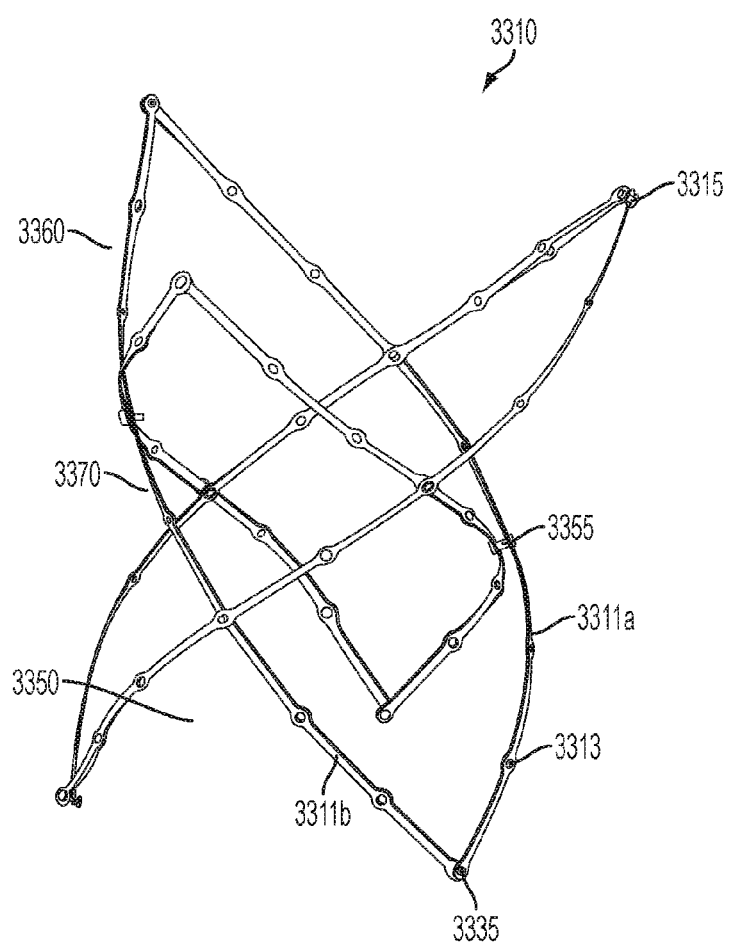
FIG. 33 is a side view of an embodiment of an hourglass securing support structure.

An alternative embodiment of a securing structure is shown in FIG. 33. In this embodiment 3310, six curved struts may be joined into three interconnected leaflets to form a structure which may have, like the securing structure of FIG. 29A, an hourglass shape such that a middle section 3370 has a narrower diameter than the distal and proximal sections and may be configured to be attached to a valve support structure, and a distal section 3360 and a proximal section 3350 with larger diameters configured to hold the securing structure 3310 in place. The embodiment of FIG. 33 may be dimensioned to be secured in the aortic valve opening. In one embodiment, the diameter at the proximal and distal sections 3350, 3360 may be about 1-3 inches. More particularly, the diameter may be about 2 inches. The diameter at the narrow section 3370 may be about 0.5-2.0 inches. More particularly, the diameter may be about 1 inch.

The embodiment shown in FIG. 33 may be made up of six curved struts, which may have a helical shape. The struts may comprise three right-handed helical struts 3311a, and three left-handed helical struts 3311b. Each of the three right-handed helical struts 3311a may be connected at both its distal and proximal ends to the same left-handed strut 3311b, at proximal pivot joint 3335 and distal pivot joint 3315, forming three pairs of struts, each pair forming a curved leaflet shape. Each of the three right-handed helical struts 3311a may also be connected to the two remaining left-handed helical struts 3311b at two middle pivot joints 3355. As shown, there are two open orifices 3313 between the proximal pivot joint and the proximal-most middle joint; two open orifices 3313 between the distal pivot joint and the distal-most middle joint; and one open orifice between the two middle pivot joints, but in other variations there may be other numbers of orifices or no orifices.

It should be noted that any of the above-described support structures can be extended beyond the anchor joints at either of both ends of the stent. By coupling a series of stents in an end-to-end chain fashion, additional stent lengths and geometries can be fabricated. In particular, an hourglass-shaped stent could be achieved by joining two cone-shaped stents at their narrow ends. The hourglass shape can also be modified by assembling the middle scissor pivots off center as shown in FIG. 14.

Certain variations of the above-described support structures can also be combined. FIGS. 31A-E show one combination, which may include variations of hourglass structure 2910 (FIG. 29A), deployment structures 3210, a valve support structure 2710 (FIG. 27A), and two support structures 3010 (FIG. 30) that act as opposing self-locking rings. In this combination structure, the central axes of the hourglass structure 2910, valve support structure 2710, and support structures 3010 may be aligned. Valve support structure 2710 may be secured to hourglass structure 2910 near the longitudinal center of hourglass structure 2910 within the lumen 2940 of hourglass structure 2910. The narrow section 2970 of hourglass structure 2910 may have a circumference configured to circumscribe the valve securing structure 2910. Support structures 3010 may be secured to hourglass structure 2910 within the lumen 2940 of hourglass structure 2910. One support structure 3010 may be secured near proximal tapered section 2950 and one support structure 3010 may be secured near distal tapered section 2960 of hourglass structure 2910. As shown in FIGS. 31A-E, the combination structure may be dimensioned for catheter delivery. In one embodiment, the total length of the combination structure may be about 5-20 cm in length. In another embodiment, the total length of the combination structure may be about 6-16 cm in length. In another embodiment, the total length of the combination structure may be about 8-14 cm in length.

Figure 29B:
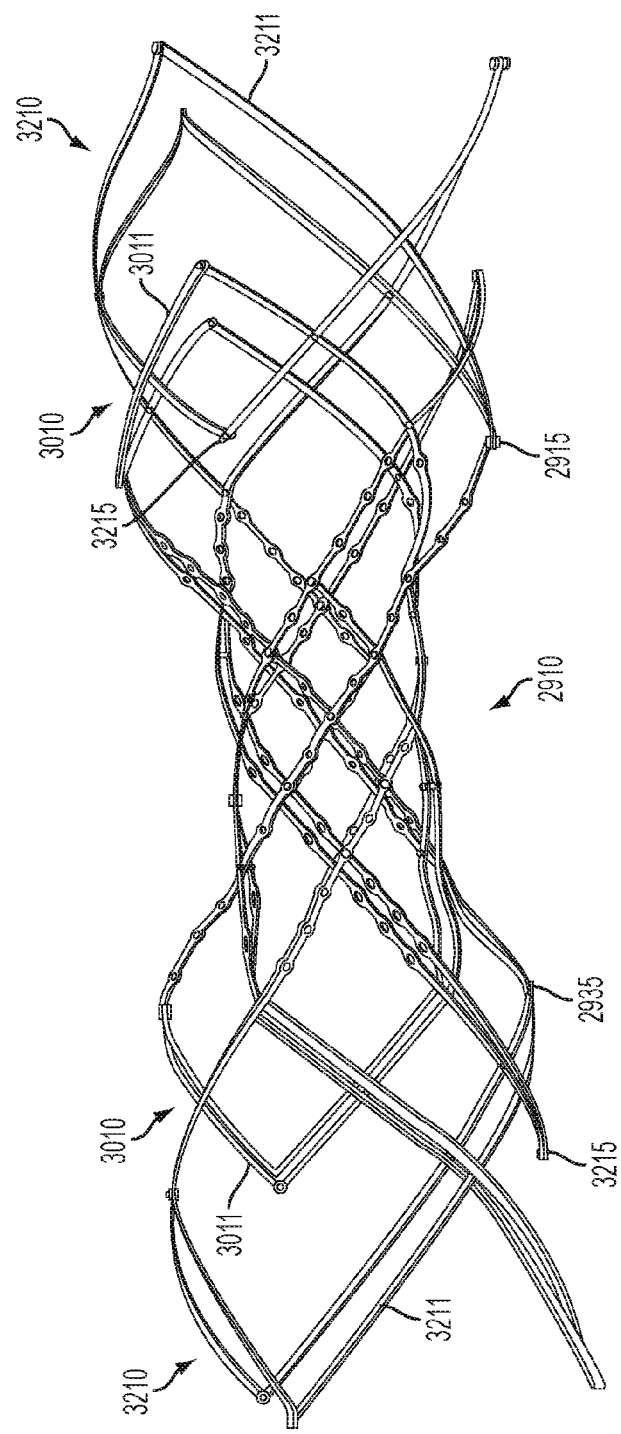
FIG. 29B depicts another embodiment of an hourglass securing support structure with attached locking rings and deployment structure.

In another embodiment, shown in FIG. 29B without valve support structure 2710, support structures 3010 may be secured to hourglass structure 2910 such that the proximal joints 2935 of hourglass structure 2910 are rotatably connected to distal joints 3215 of support structure 3010, and the distal joints 2915 of hourglass structure 2910 are rotatably connected to the proximal joints 3215 of a second support structure 3010. Thus, rather than the support structures 3010 being placed within the length of hourglass structure 2910 as in the embodiment shown in FIG. 29A, the support structures 3010 in the embodiment shown in FIG. 29B may be located beyond the length of the hourglass structure 2910. In the embodiment shown in FIG. 29B, one deployment structure 3210 may be attached each of the two support structures 3010. As shown, the strut members 3211 of deployment structure 3210 may overlap with the strut members 3011 of support structure 3010 from the outermost joint 3215 to the middle pin joint 3215. The overlap between strut members 3211 and 3011 may allow greater flexibility in the deployment structure. The combination structures may have other properties that allow for greater flexibility in the deployment structure. For example, as shown in FIG. 29B, hourglass structure 2910 may not have all the segments of helical struts 2911 that are shown in FIG. 29A. In the embodiment shown in FIG. 29B, the hourglass structure 2910 may not contain the portion of outer, right-handed strut member 2911a-1 extending from the distal anchor pin joint 2915-1 to the scissor pin joint connection 2955 with inner, left-handed strut member 2911b-6; and the hourglass structure 2910 may not contain the portion of inner, left-handed strut member 2911b-1 extending from the distal anchor pin joint 2915-1 to the scissor pin joint connection 2955 with outer, right-handed strut member 2511a-2. The omission of these segments of the helical struts may allow greater flexibility in the deployment structure. In other embodiments, in addition or alternatively, other segments of the helical struts may also be omitted.

Figure 31A:
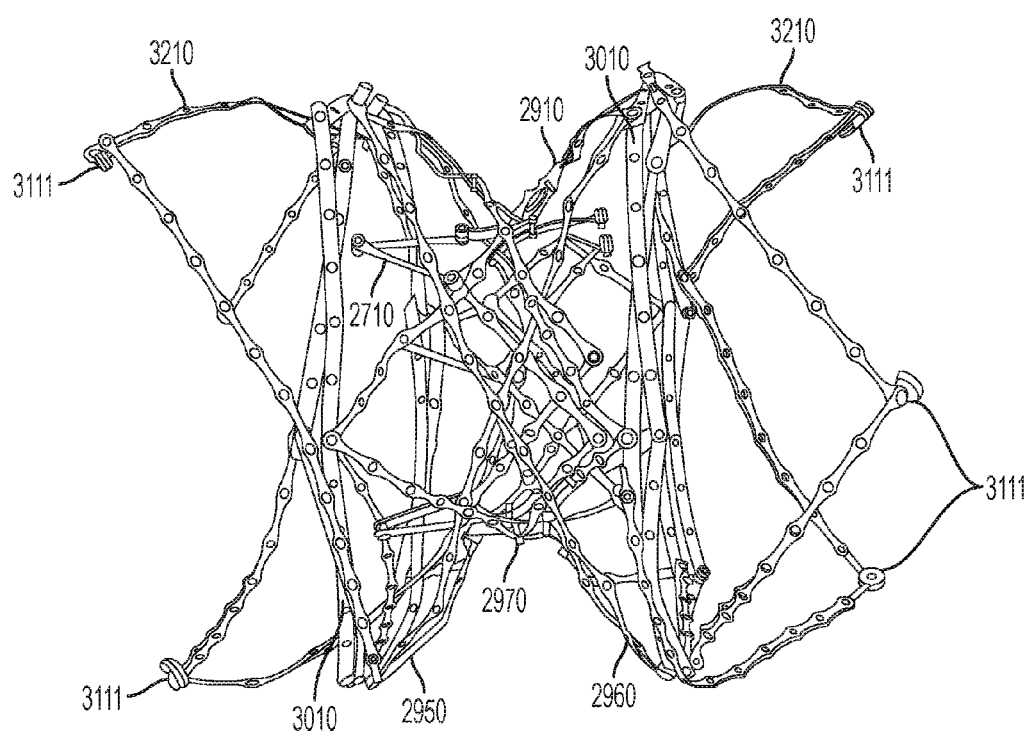
FIG. 31A is a combined structure with the hourglass support structure of FIG. 29A, support structure of FIG. 27A, and support structures of FIG. 1, shown in an expanded state.
Figure 31B:
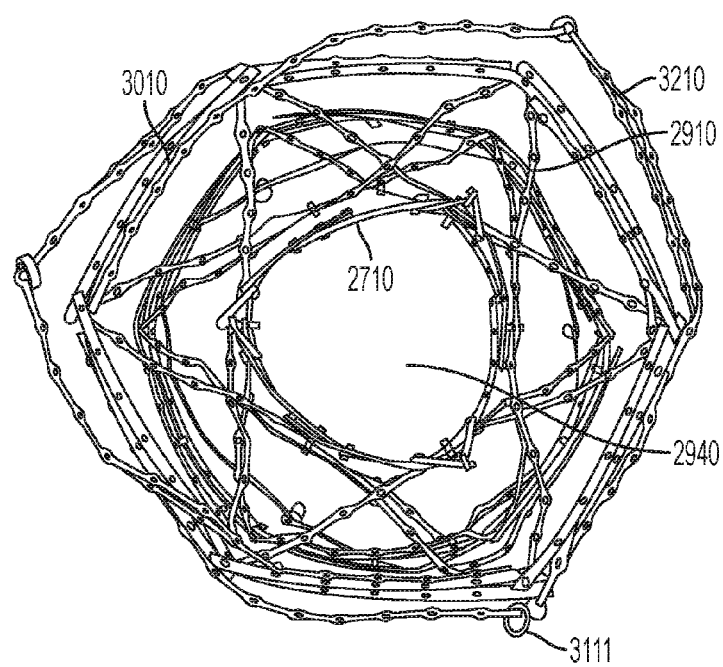
FIG. 31B is an axial view of the structure of FIG. 31A.
Figure 31C:
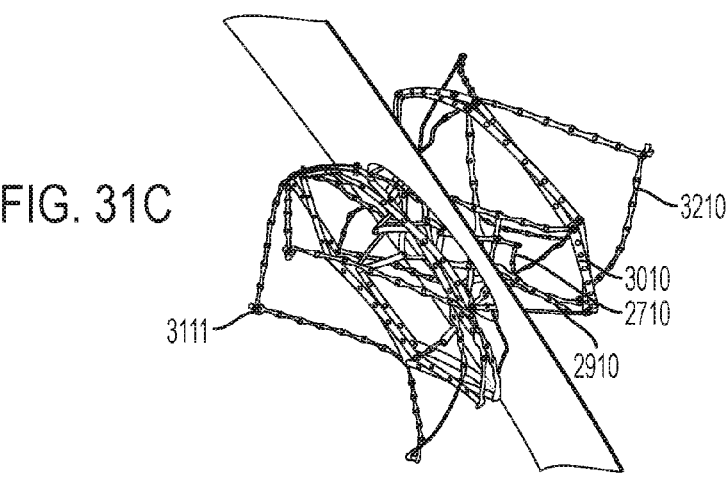
FIGS. 31C and 31D are various side perspective views the combined structure of FIG. 31A deployed through an opening.
Figure 31D:
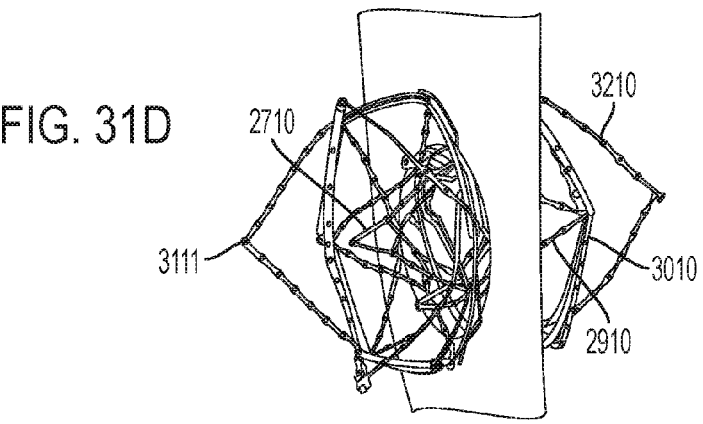
Figure 31E:
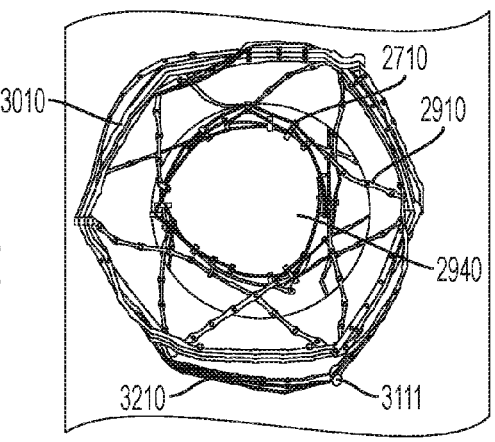
FIG. 31E is an axial view of the combination of FIG. 31A deployed through the opening.
Figure 31G:
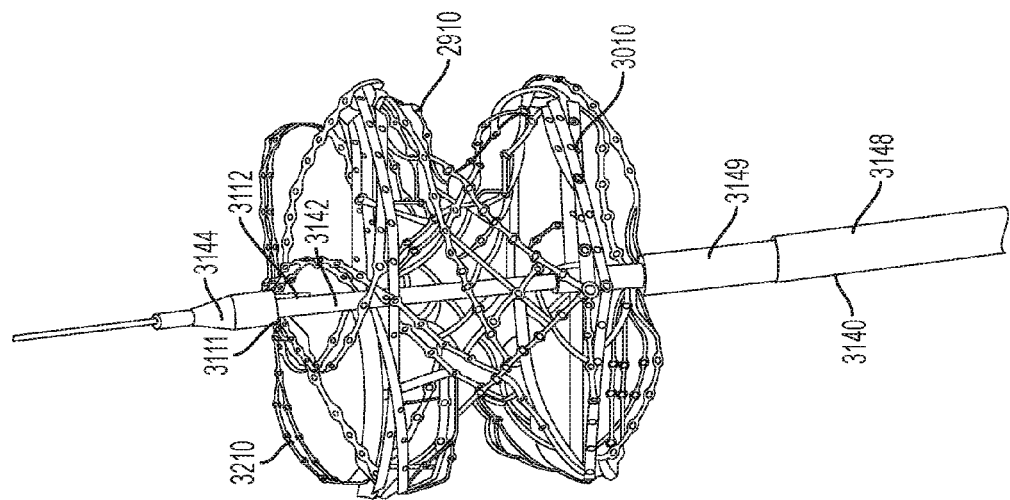
FIGS. 31F and 31G are side perspective views of the combined structure in FIG. 31A coupled to a control catheter assembly, in an expanded state.
Figure 31F:
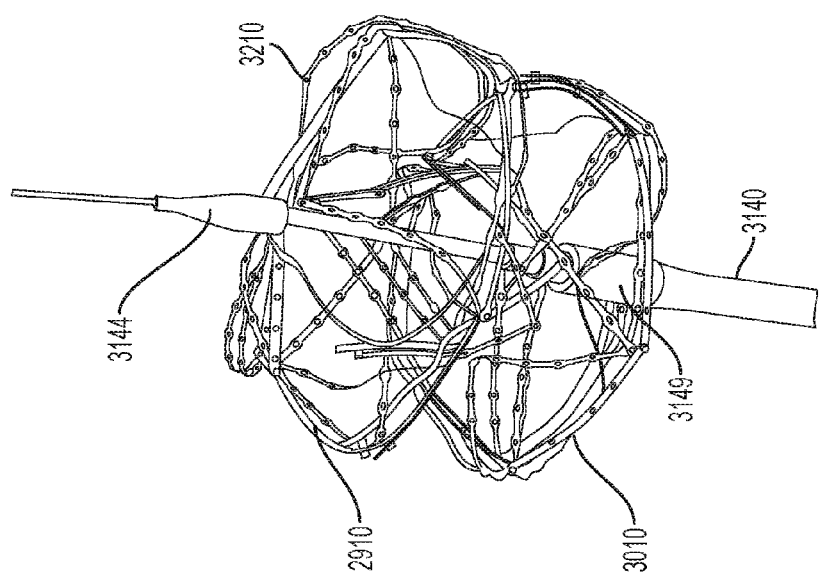
Figure 31H:
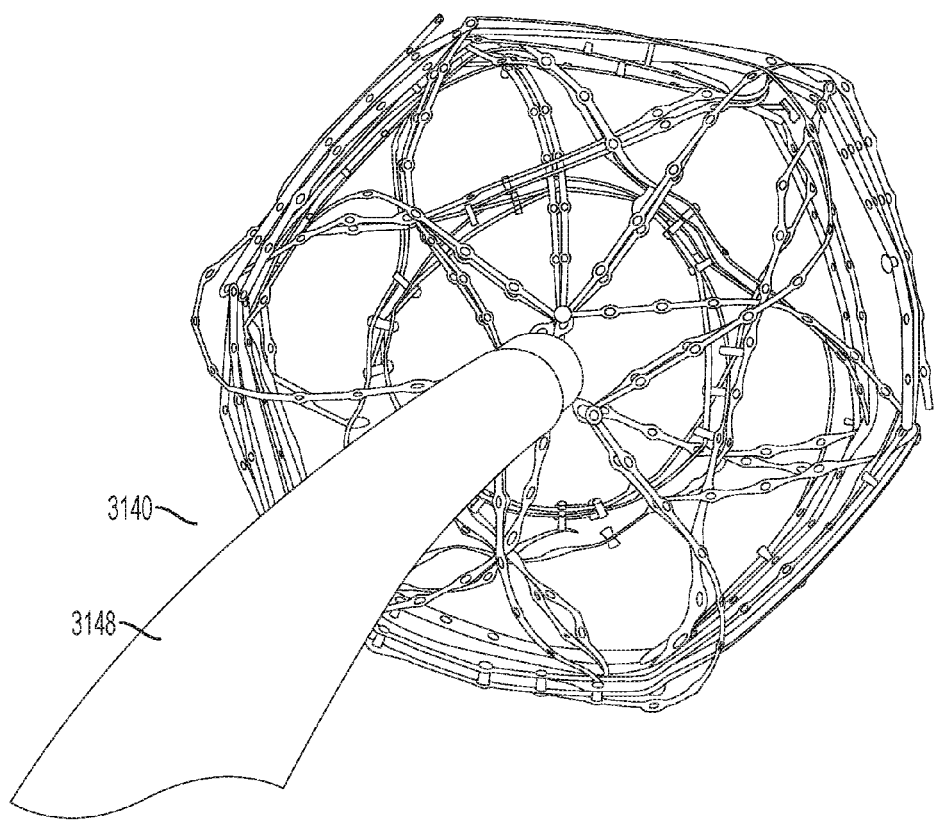
FIG. 31H is an axial view of the combined structure in FIGS. 31F and 31G.
Figure 31I:
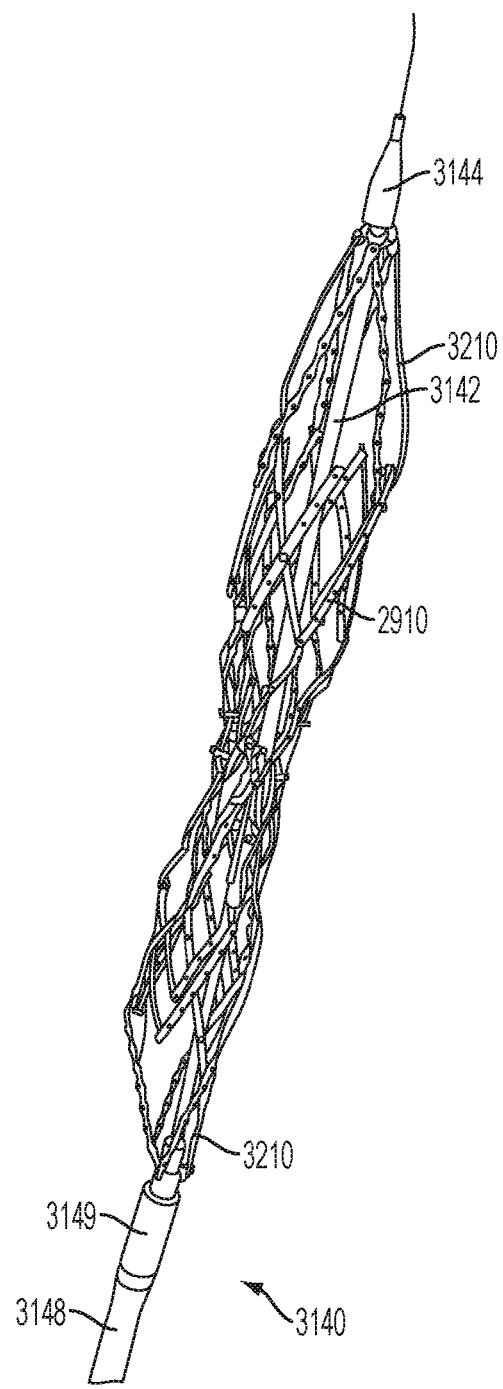
FIG. 31I is the combination of FIG. 31A, with control catheter assembly, in a collapsed state.

The combination structure may also include attachment rings 3111 secured to proximal pin joints 2915 of proximal deployment structure 3210 and distal pin joints 2915 of distal deployment structure 3210, as shown in FIG. 31G. The attachment rings 3111 may be secured to proximal pin joints 2915 by loops, wherein both ends of the loops may be attached to the proximal joints 2915. The attachment rings 3111 may be secured to distal pin joints 2915 by loops, wherein both ends of the loops may be attached to the distal joints 2915. In one embodiment, the loops may be formed from a flat bar-shaped member having a rectangular cross-section folded to create a loop, and the attachment rings 3111 may be formed from a wire having a circular cross-section wrapped into a ring shape, and the cross-sectional area of the wire may be smaller than the cross-sectional area of the bar-shaped member. The attachment rings 3111 can spin and rotate freely within the loops.

Figure 35A:
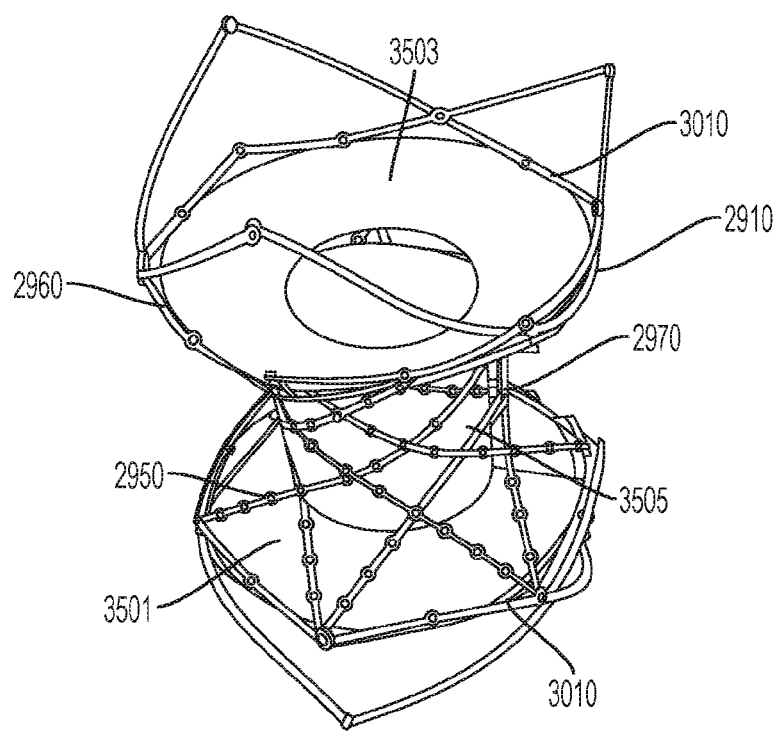
FIGS. 35A to 35C depict various embodiments of support structures with skirts.

The combination structure may also include one or more skirts. The skirt may be a thin layer of material that lines the structure. The skirt material can be pericardial tissue, polyester, PTFE, or other material or combinations of materials suitable for accepting tissue in growth, including chemically treated materials to promote tissue growth or inhibit infection. The skirt may function to reduce or eliminate leakage around the valve, or "paravalvular leak," and in particular, may have increased sealing when greater pressure is applied to the skirt. In some embodiments, there may be a skirt at the proximal tapered section 2950 of hourglass structure 2910 and at the distal tapered section 2960 of hourglass structure 2910. In other embodiments, for example the one shown in FIG. 35A (shown without valve support structure 2710), there may be a skirt 3501 at the proximal tapered section 2950 of hourglass structure 2910, a skirt 3503 at the distal tapered section 2960 of hourglass structure 2910, and a skirt 3505 at the narrow section 2970 of hourglass structure 2910. In some embodiments, skits 3501, 3503, 3505 may be contiguous with each other; in other embodiments, kits 3501, 3503, 3505 may be separate. In some embodiments, the skirt elements may be located on the outside of the hourglass structure; in other embodiments, the skirt elements may be located on the inside of the hourglass structure. In other embodiments, the skirt elements may be sandwiched between multi-ply struts in the hourglass structure. In some embodiments, the skirt material may line the full circumference of the proximal tapered section 2950, distal tapered section 2960, and narrow section 2970 of hourglass structure 2910, as shown in FIG. 35A.

Figure 35B:
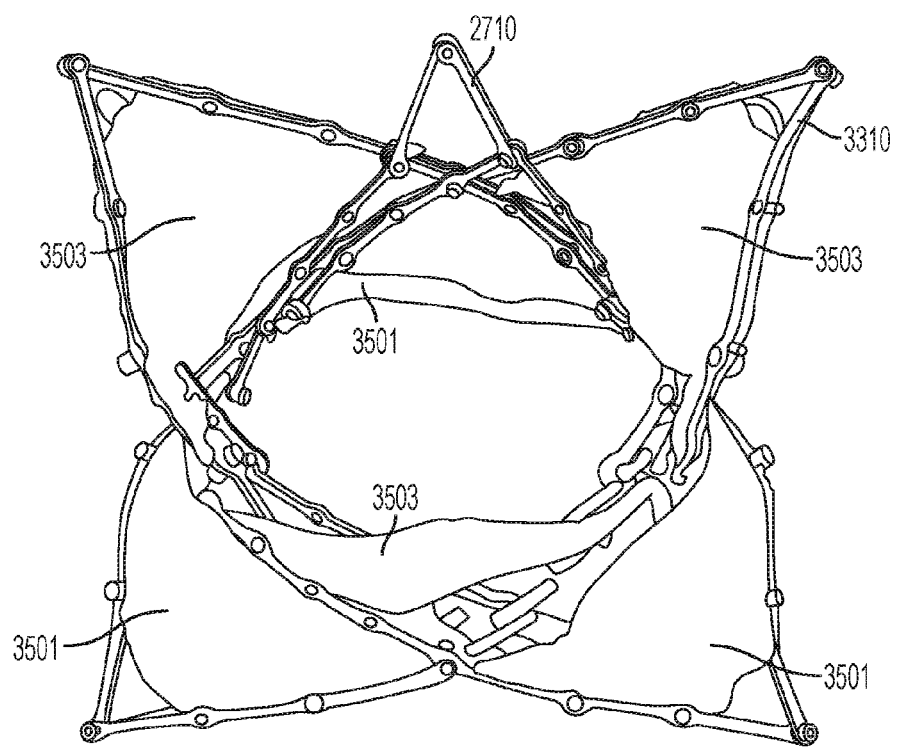
Figure 35C:
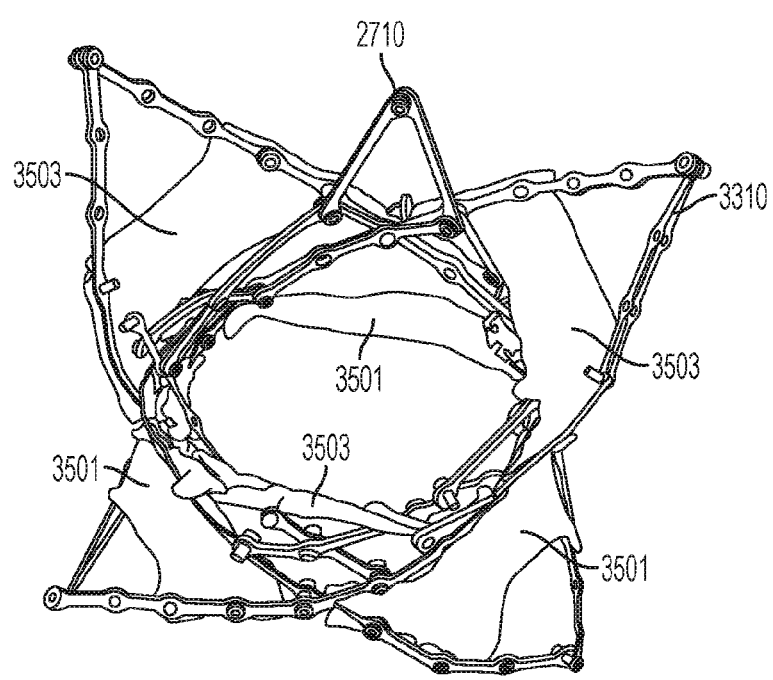
Figure 35D:
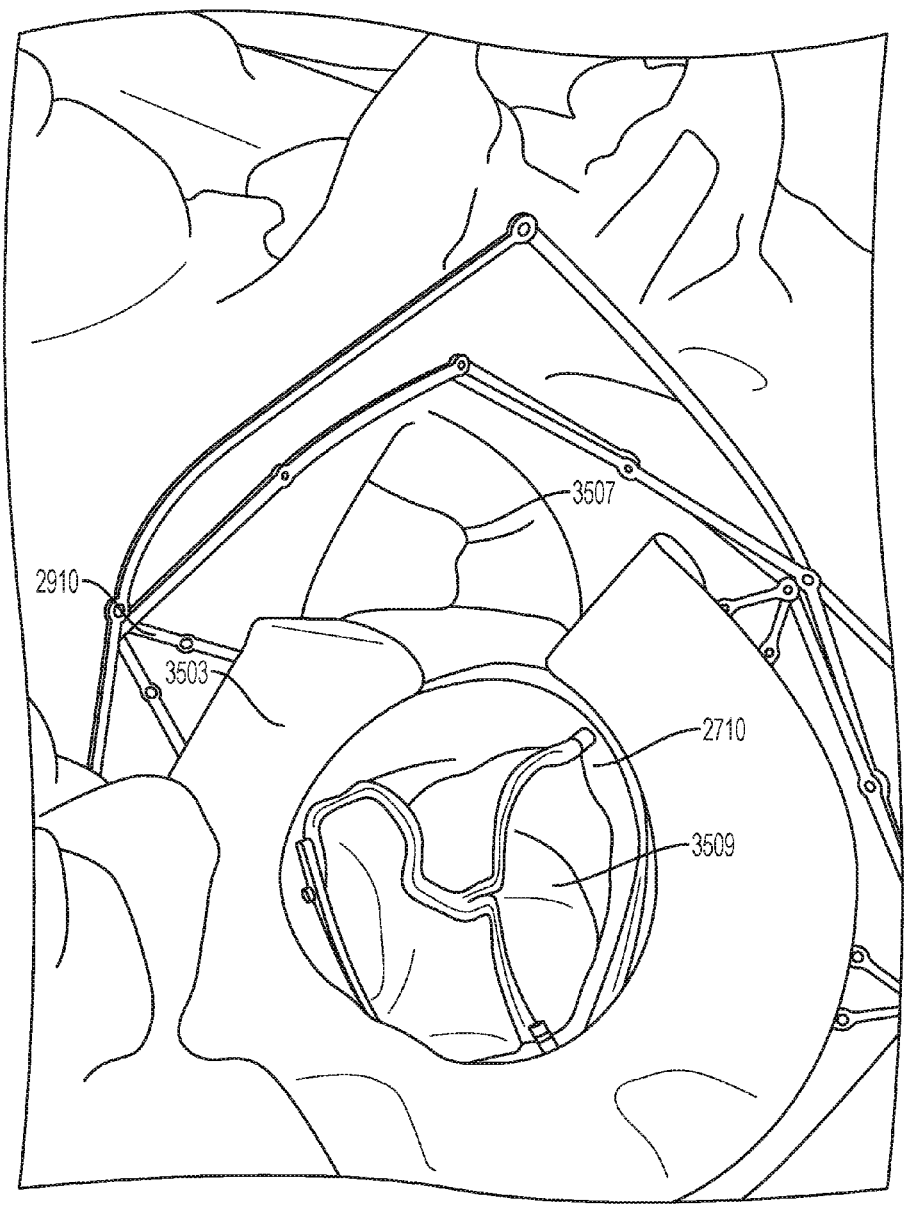
FIGS. 35D and 35E are ventricular and atrial views of a support structure with a skirt implanted in a cadaver heart at the mitral valve position, respectively.
Figure 35E:
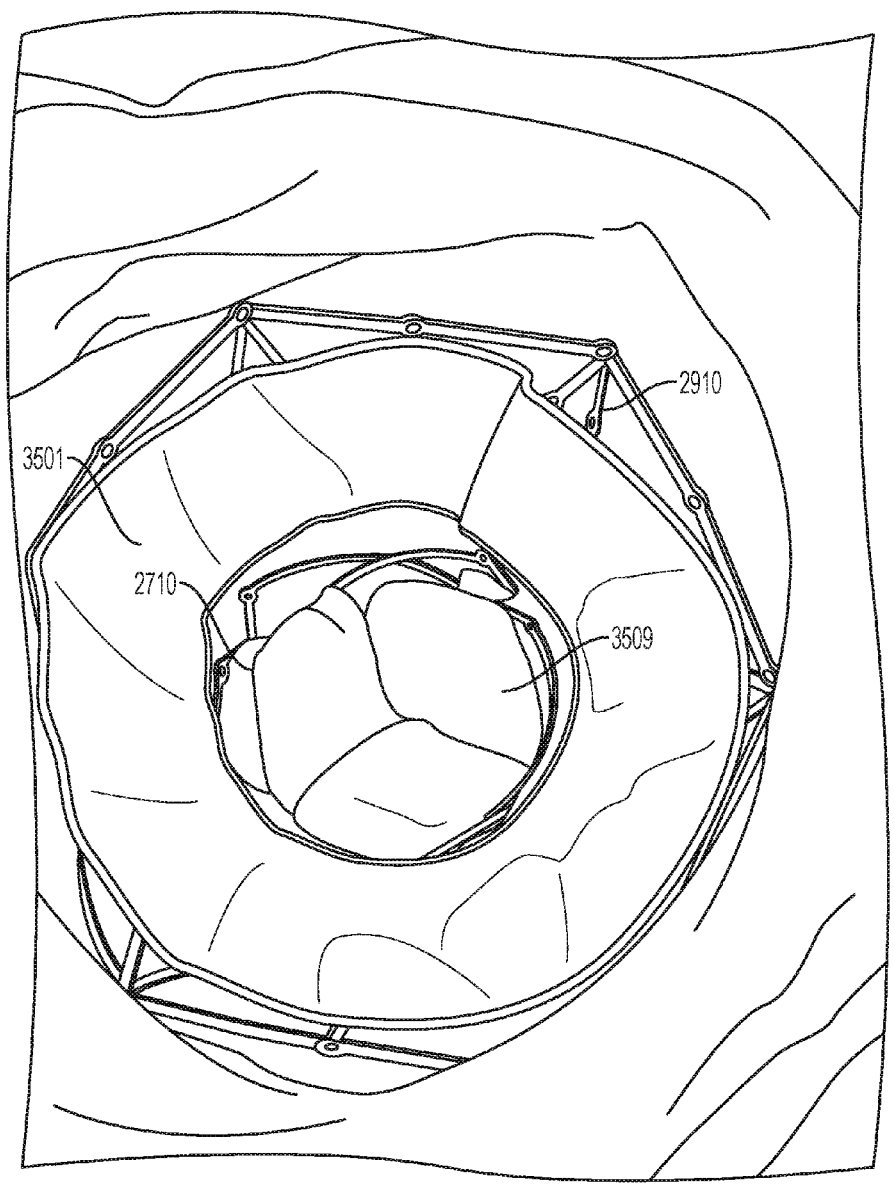

In other embodiments, the skirt may line only a portion of the full circumference of the proximal tapered section 2950, distal tapered section 2960, and narrow section 2970 of hourglass structure 2910. For example, as shown in FIG. 35D, the skirt 3503 lining the distal tapered section 2960 may contain an opening 3507 to preserve an aortic outflow tract. FIG. 35D shows a combination structure, including tissue valve 3509, implanted in the mitral opening from a ventricular view. In the embodiment in FIG. 35D, the opening 3507 in the skirt material corresponds with an open region in the support structure (i.e. a region without a strut), which in turn corresponds with the aortic outflow tract. FIG. 35E is an atrial view of the same structure implanted in the mitral opening, showing the proximal end of the same embodiment. As shown in FIG. 35E, the skirt 3501 lining the proximal tapered section 2950 may line the full circumference of the proximal tapered section 2950. In other embodiments, the skirt may be made up of several separate, non-contiguous regions. For example, FIG. 35B shows an embodiment of the combination structure of FIG. 27B, having a securing structure 3310 connected to a valve support structure 2710. The skirt in the embodiment in FIG. 35B has six separate regions 3501a, 3501b, 3501c, 3503a, 3503b, 3503c. The skirt regions 3503a, 3503b, 3503c are attached to the upper portion of each of the three the leaflets in the portion extending above the valve support structure 2710. The skirt regions 3501a, 3501b, 3501c are attached to the upper portions of each of the three leaflets in the portion extending below the valve support structure 2710. In some variations, such as the one shown in FIG. 35B, the skirt material may extend approximately 75-95% toward the distal joint between the two struts forming each leaflet. In other variations, the skirt regions may be smaller. For example, in the embodiment in FIG. 35C, the skirt material may extend approximately 40-60% toward the distal joint between the two struts forming each leaflet.

Although FIGS. 31A to 31E illustrate one combination of the structures, the structures described here can be used in other combinations, or other variations of these structures can be combined. For instance, a combination may include variations of hourglass structure 2910 (FIG. 29A), two deployment structures 3210 (FIG. 29A), valve support structure 2510 (FIG. 25) and prosthetic valve 121, and/or two support structures 10 (FIG. 1). Another combination may include the hourglass securing support structure 3310 of FIG. 33, a variation of the valve support structure 2510 (FIG. 27A) dimensioned for placement in the aortic valve opening, and/or a prosthetic valve 121. In another variation, a combination may have other locking mechanisms instead of support structure 3010 that act as locking rings. For instance, the locking mechanism may be a drive screw, a shim axially interwoven between the inner and outer struts of hourglass structure 2910, or a plug placed into one of the cells formed by the struts in the combination structure.

The combination can be reversibly expanded and compressed. The structures 2910, 2710, 3210, and 3010 can be secured and aligned such that by actuating the linkages on one of the four structures, the entire combination of four structures is expanded or compressed. The combination can be locked by expanding it into a fully expanded state, wherein support structure 3010 enters a locked state such that radially inward pressure does not cause the support structure 3010 to re-compress. Having support structure 3010 in a locked state can also prevent further movement of the combination. The combination or individual structures may also be locked in a fully expanded state through other means. For instance, in one variation the support structure of FIG. 27A (2710) may enter a locked state when it enters a fully expanded state, wherein radially inward pressure does not cause the support structure 2710 to re-compress. Once in a locked state, the hourglass configuration may allow the structure to be secure din the mitral valve opening without requiring a strong outward force to hold the structure in place.

A surgeon can expand or compress the combination from a location remote from the implant site using an actuation mechanism. The actuator mechanism can exert force to expand the combination diameter by either increasing the distance between neighboring scissor joints, or decreasing the distance between the anchor joints in any one of the structures in the combination. In one variation, the actuator mechanism can be the same as actuator mechanism 30 described in detail above. One control catheter assembly 40 usable with the actuator mechanism is described in detail above.

Figure 32:
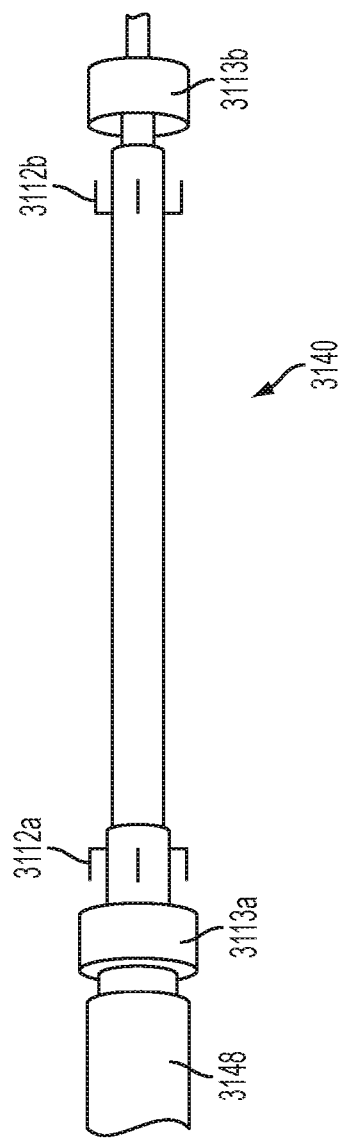
FIG. 32 is a side view of a control catheter assembly.

FIGS. 31F-I show the combination of FIGS. 31A-E with control catheter assembly 3140. Control catheter assembly 3140 can be dimensioned to be inserted with the combination structure through a biological lumen, such as a human artery. As shown in FIG. 32, the control catheter assembly 3140 has a flexible outer sheath 3148 encasing four nested catheters. One nested catheter may have L-shaped hooks 3112a, wherein the open end of the hook may be proximally facing. Another nested catheter may have L-shaped hooks 3112b, wherein the open end of the hook may be distally facing. The distally facing hooks may be located distal to the proximally facing hooks. The L-shaped hooks 3112 may be configured such that the attachment rings 3111 can be looped around the hooks 3112. Another nested catheter may have attached end cap 3113a, wherein the end cap's opening may be distally facing and may be configured to fit over the ends of the proximally facing L-shaped hooks 3112a. Another nested catheter may have attached end cap 3113b, wherein the end cap's opening may be proximally facing and may be configured to fit over the ends of the distally facing L-shaped hooks 3112b. The end caps 3113 may be configured such that if attachment rings 3111 are looped around hooks 3112, placing the end caps over the L-shaped hooks 3112 may secure the attachment rings 3111 over the hooks 3112. Each of the four nested catheters may be independently moveable relative to the others, or the four catheters may be able to be moved concertedly. The proximal ends of the catheters may contain screw locks to allow for concerted movement. In particular, in one embodiment the catheter comprising end cap 3113a may be able to be screw-locked to the catheter comprising hooks 3112a; and the catheter comprising end cap 3113b may be able to be screw-locked to the catheter comprising hooks 3112b. In another embodiment, all four catheters can be configured to screw-locked together. In another embodiment, hooks 3112 can have other shapes.

The combination structure shown in FIGS. 31A-I or other combinations can be attached to the control catheter assembly by looping the attachment rings 3111 on the distal end of the deployment structure 3210 over the distally facing L-shaped hooks 3112b and securing the attachment rings to the hooks using the end caps 3113b; and looping the attachment rings 3111 on the proximal end of the combination structure over the proximally facing L-shaped hooks 3112a and securing the attachment rings to the hooks using the end caps 3113a. In another embodiment, the combination structure can be attached to the control catheter assembly by looping the attachment rings 3111 on the proximal end of the combination structure over the distally facing L-shaped hooks 3112b and securing the attachment rings to the hooks using the end caps 3113b; and looping the attachment rings 3111 on the distal end of the combination structure over the proximally facing L-shaped hooks 3112a and securing the attachment rings to the hooks using the end caps 3113a. When the attachment rings 3111 are secured to the control catheter assembly, the deployment struts 3211 of deployment structure 3210 are centrally deflected to allow attachment to the catheter control assembly.

The orientation in which the combination structure is attached to the control catheter assembly may depend on the method of delivery. In one embodiment, the combination structure may comprise a prosthetic mitral valve and may be delivered through the femoral artery; in another embodiment, a combination structure may comprise a prosthetic aortic valve and may be delivered through the femoral artery. In such embodiments the proximal end of the combination structure may be attached to the proximally facing L-shaped hooks 3112a. In another embodiment, the combination structure may comprise a prosthetic mitral valve and may be delivered transseptally, either through the superior vena cava or through the inferior vena cava; in another embodiment, a combination structure may comprise a prosthetic aortic valve and may be delivered transseptally, either through the superior vena cava or through the inferior vena cava; in such embodiments the proximal end of the combination structure may be attached to the proximally facing L-shaped hooks 3112a. In another embodiment the combination structure may comprise a prosthetic mitral valve and may be delivered transapically; in another embodiment, a combination structure may comprise a prosthetic aortic valve and may be delivered transapically; in such embodiments the proximal end of the combination structure may be attached to the distally facing L-shaped hooks 3112b.

The combination structure shown in FIGS. 31A-I and other combination structures may be encased in a flexible sheath during insertion and delivery. The sheath may be removed before or during use of the actuator mechanism to expand the diameter. In one variation, the sheath is removed during the expansion of the diameter, and as a result, the distal portion of the combination structure no longer covered by the sheath may expand, while the proximal portion of the combination structure still covered by the sheath may remain compressed until the sheath is fully removed.

The combination structure shown in FIGS. 31A-I and other combination structures may be highly flexible. Flexibility may be desirable during delivery of the structure, particularly in an embodiment in which the structure is delivered transseptally. In some instances, the flexibility of the combination structure may be varied by varying the spacing between strut members. More particularly, the flexibility may be able to be increased by increasing the spacing between strut members and/or increasing the longitudinal distance along strut members between joints.

The combination structure may be able to be expanded and compressed by moving the catheters to change the distance between distally-facing L-shaped hooks 3112b and proximally-facing L-shaped hooks 3112a. Shown in collapsed state in FIG. 31I, the distance between the distally-facing L-shaped hooks 3112b and proximally-facing L-shaped hooks 3112a may be at a maximum. The combination structure may be able to be then expanded into the expanded state, shown in FIGS. 31F-H, by retracting the catheters with the proximally facing hooks 3112b and corresponding end cap 3113b towards the distally facing hooks 3112a. The hourglass structure 2910, valve support structure 2710, and support structure 3010 may be fully radially deployed while the deployment structure 3210 remains attached to the control catheter assembly. The combination structure may also be able to be recollapsed by manipulating the catheters to move proximally facing hooks 3112a and corresponding end cap 3113a away from the distally facing hooks 3112b and end cap 3113b. The catheters may be able to be retracted and lengthened by a surgeon at a location remote from the implant site. The ability to reversibly expand and collapse the combination structure may allow the device to be re-positioned by the surgeon. The surgeon may also use the control catheter assembly to rotate or retrieve the structure.

By manipulating the catheters such that the combination structure enters a fully expanded state, support structures 3010 may enter a locked state, described in more detail above, which may in turn cause the combination structure to enter a locked state. In the locked state, inward radial pressure or axial pressure may not cause the combination structure to re-collapse. The combination structure may then be able to be released from the control catheter assembly by sliding the end caps 3113 off the hooks 3112, which may allow attachment rings 3111 to slip off hooks 3112.

FIGS. 18A and 18B depict another embodiment of an articulated tubular structure 1800, wherein at least one of the inner and outer struts 1802, 1804 of the structure 1800 extend beyond the end articulations 1806, 1808 of the struts 1802, 1804. As depicted in FIG. 18B, when the structure 1800 is in a collapsed state, the struts 1802, 1804 may have a generally linear configuration and comprising a slightly offset but generally longitudinal orientation (with respect to the longitudinal axis of the structure 1800). In the expanded stated depicted in FIG. 18A, the middle segments 1810, 1812 of the struts 1802, 1804 may assume an arcuate configuration (e.g. segment of a helix) with an acute angle relative to the longitudinal axis of the structure 1800. As depicted in FIG. 18A (and also depicted in FIG. 1), in the expanded state, each of the outer struts 1816 may generally comprise the same angled orientation, relative to a perimeter of the structure, transverse the longitudinal axis of the structure 1800, while each of the inner struts 1814 may comprise the opposite angled orientation relative to the perimeter. The end segments 1814, 1816 of the struts 1802, 1804, however, may only be supported on one end at the end articulations 1806, 1808, and therefore may comprise a generally linear configuration with a tangential angle orientation relative to the adjacent middle segment 1810, 1812. The end segments 1814, 1816, overall can provide the structure 1800 with first and second perimeters that are larger than a middle perimeter of the structure 1800, e.g. a parabolic shape. The relative size differences between the first and second perimeters and the middle perimeter may be affected by the length of the end segments 1814, 1816 and the degree of expansion provided to the structure 1800, with relatively smaller size difference associated with smaller degrees of expansion and larger size differences (e.g. a more accentuated parabolic shape vs. a more cylindrical shape) at larger degrees of expansion.

Figure 19A:
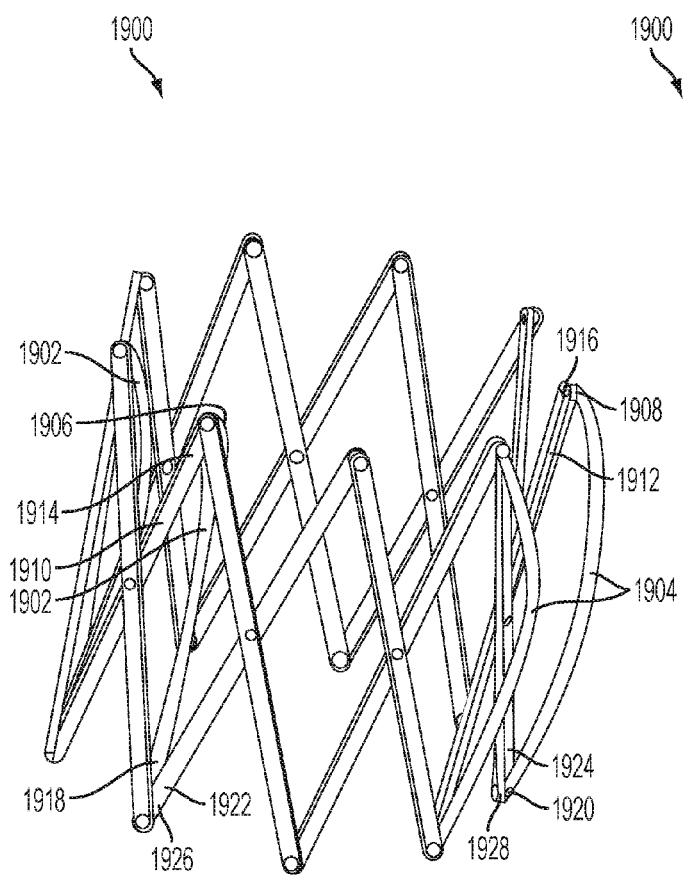
FIGS. 19A and 19B are perspective and side elevational views, respectively, of one embodiment of an articulated support structure comprising inner and outer bow struts.
Figure 19B:
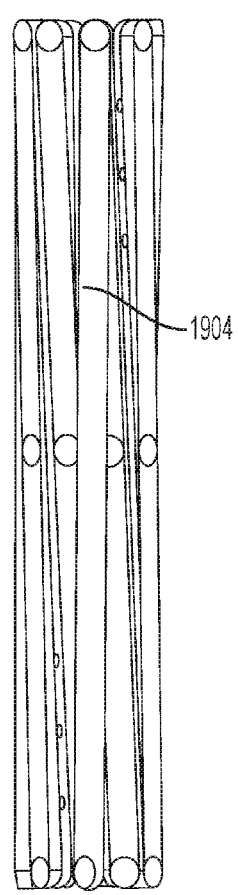

In another embodiment, illustrated in FIGS. 19A and 19B, the articulated structure 1900 may further comprise either inner 1902 and/or outer 1904 bow struts. For illustrative purposes, only selected struts 1902, 1904 are depicted on structure 1900, but a plurality of each type of bow strut 1902, 1904 is contemplated, up to every available location on the structure 1900. Each bow strut 1902, 1904 may comprise a first end 1906, 1908 attached to an inner or outer strut 1910, 1912 at their respective first ends 1914, 1916, and a second end 1918, 1920 attached to a different inner or outer strut 1922, 1924 at their respective opposite ends 1926, 1928. Typically, but not always, the different inner or outer strut 1922, 1924 may be immediately or directed adjacent to the original strut 1910, 1912. Alternatively, instead of being attached at the opposite ends 1926, 1928 of the different strut 1922, 1924, the bow struts may be attached to a middle position or a middle articulation of the struts 1922, 1924 (including but not limited to any of the middle articulations of the multi-level articulated structure 2000 in FIG. 20, discussed below). As shown in FIG. 19B, the exemplary outer strut 1904 may comprise a generally linear configuration when the structure 1900 is in a collapsed state, but in the expanded state depicted in FIG. 19A, the first end 1906, 1908 and second ends 1918, 1920 of the bow struts 1902, 1904 come closer together, causing the bow struts 1902, 1904 to bow radially inward or outward, respectively. In some variations, the bow struts 1902, 1904 may be used to circumferentially retain other structures (not shown) between the inner bow struts 1902, 1904 and the primary struts 1910, 1912, 1922, 1924. In one example, the other structure may comprise a tubular balloon, resilient seal, skirt, or elongate therapy delivery mechanism (e.g. electrodes, drug elution or drug infusion, etc.).

Figure 20:
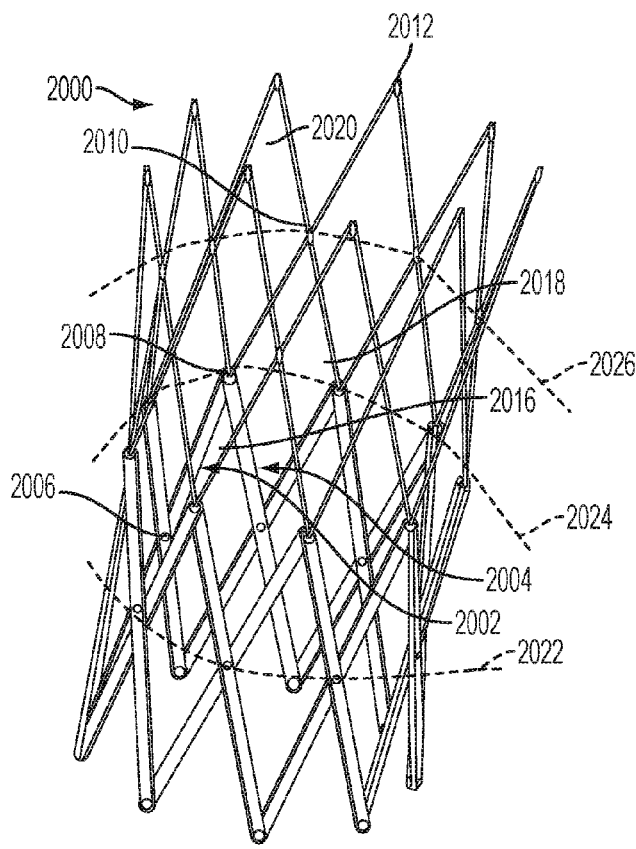
FIG. 20 depicts a perspective view of an embodiment of a self-expanding articulated structure comprising a multi-level configuration.

FIG. 20 depicts another example of an articulated structure comprising tubular articulated structure 2000 comprising longer struts 2002, 2004 with more than one middle articulation 2006, 2008, 2010, in addition to their end articulations 2012, 2014. With these additional features, the struts 2002, 2004 may be arranged to provide two or more sets of cells 2016, 2018, 2020 aligned along different perimeters 2022, 2024, 2026. In addition, to providing longer structures 2000, is was surprisingly discovered that the use of longer struts 2002, 2004 wherein at least two sets of cells 2016, 2018 are formed, the structure 2000 may be capable of self-expansion without additional mechanisms or forces acting on the struts 2002, 2004 of the structure 2000. Although not wishing to be bound by the hypothesis, it is believed that this intrinsic self-expansion property of structure 2000 may be the result of greater total degree of curvature in the struts 2002, 2004 when in the collapsed state, which results in greater stress and strain acting on the struts 2002, 2004 that sufficient high that then can overcome resistance of the collapsed state to relatively straighten to the expanded state, reducing its potential energy. Even more surprising, it was found that embodiments of structure wherein the struts comprise two middle articulations and two sets of aligned cells (one each less than the embodiment depicted in FIG. 20), the structure may have an intrinsically stable collapsed state wherein the net frictional forces resisting expansion exceed expansion forces of the struts, but if the structure is slightly expanded from the collapsed state to a point where the net frictional forces of the structure are relatively lower (e.g. less overlapping surface area between the inner and outer struts), the structure may still have at least some self-expansion ability. In contrast, the embodiment depicted in FIGS. 1 and 3 may be configured to be inherently stable at any configuration it is placed in, e.g. full collapse, partial collapse/expansion, and full expansion.

Figure 21:
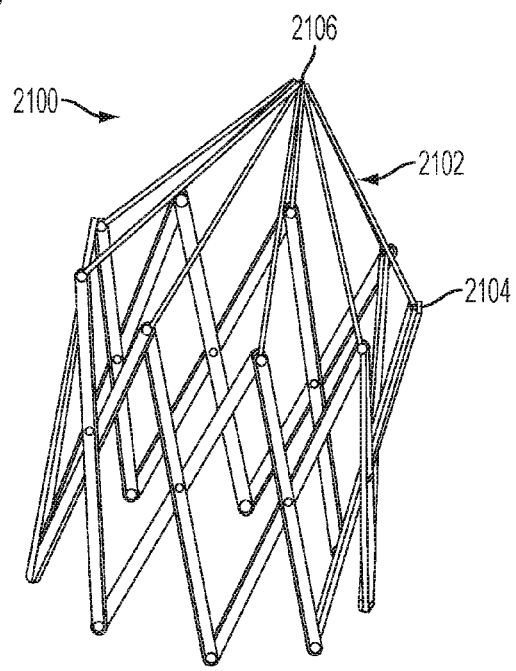
FIG. 21 depicts a perspective view of an embodiment of an articulated support structure comprising centrally attached radial struts.
Figure 22A:
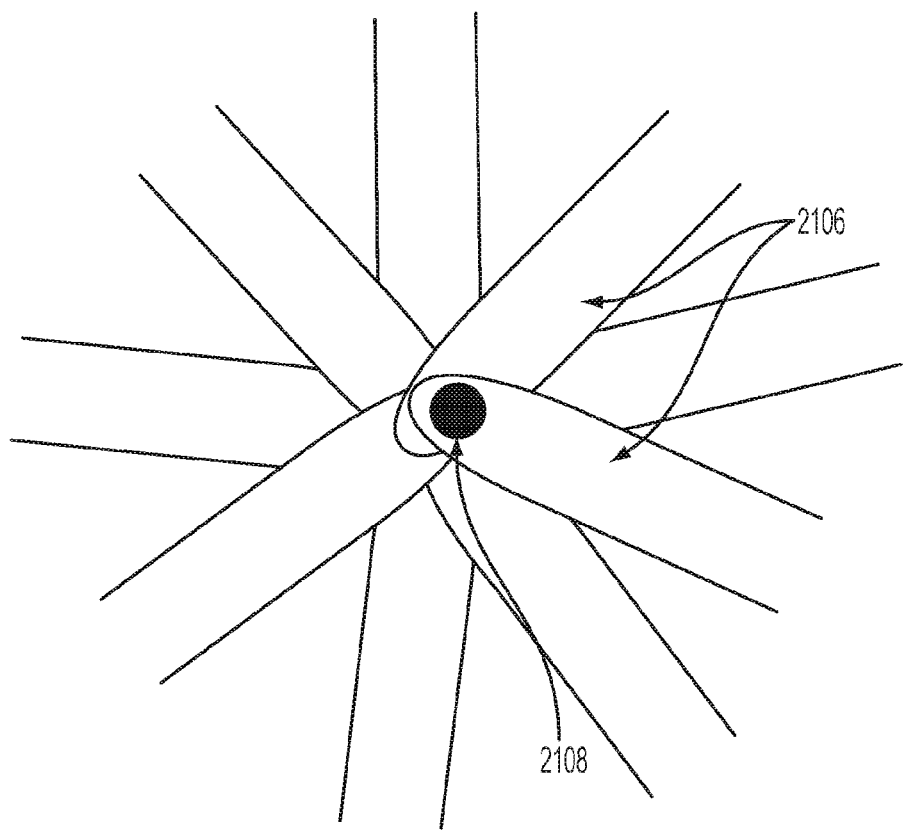
FIGS. 22A and 22B are schematic superior views of alternate embodiments of interconnection configurations of the centrally attached radial struts in FIG. 21.
Figure 22B:
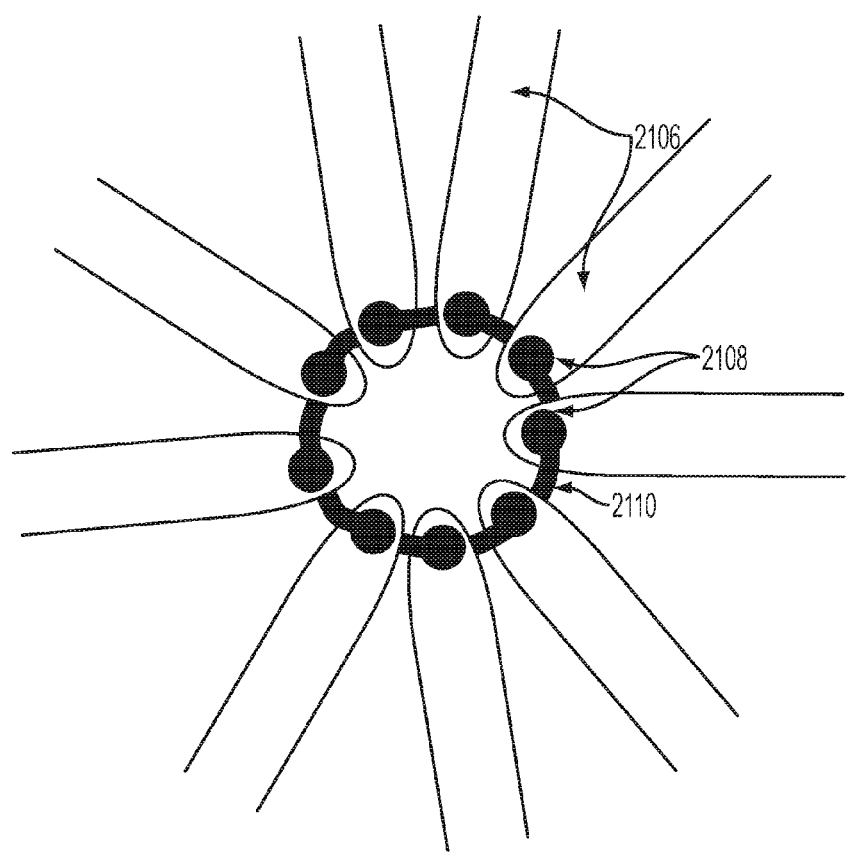

FIG. 21 schematically depicts another embodiment of an articulated structure 2100 comprising a set of radial struts 2102 with outer ends 2104 coupled to the inner and/or outer struts 2106 and inner ends 2106 coupled to the other inner ends 2106. Although FIG. 21 only depicts one set of radial struts located at one end of the structure 2100, in other embodiments, a second set of struts may be provided at the other end of the structure. The radial struts 2102 may or may not impart a radial expansion force to the inner and/or outer struts 2106, depending upon their configuration. In FIG. 22A, wherein the inner ends 2106 are rigidly affixed together, a greater expansion force may be imparted as the inner ends 2106 attempt to straighten. Although the ends 2106 in FIG. 22A are depicted with apertures 2108 on their ends 2106 that are aligned, of course, the ends 2106 may be rigidly affixed together without apertures or without aligned apertures. In contrast, in FIG. 22B, the loosely affixed ends 2106, performed by using a flexible or rigid loop or ring 2110 at their apertures 2108, may permit at least some tilting, pivoting or stress-relieving so that the radial struts do not impart any significant expansion force.

In some embodiments, a structure comprising two sets of radial struts may be used to perform radiofrequency or heater probe ablation of tissue. In further embodiments, the structure may be configured to provide circumferential ablation of tissue in a cavity or tubular body structure. Depending upon the size of the structure and the degree of radial expansion or resistance to radial collapse, the ablation structure may be selected to ablate the opening of a cavity or lumen, while resisting significant entry into the cavity or lumen by resisting collapse via the intrinsic mechanical properties of the inner and outer lumens, and/or the radial struts. Such an ablation device may be used, for example, for ablation about the pulmonary vein for treatment of cardiac arrhythmias, or for ablation about the renal artery for treatment of hypertension.

Figures 23, 24:
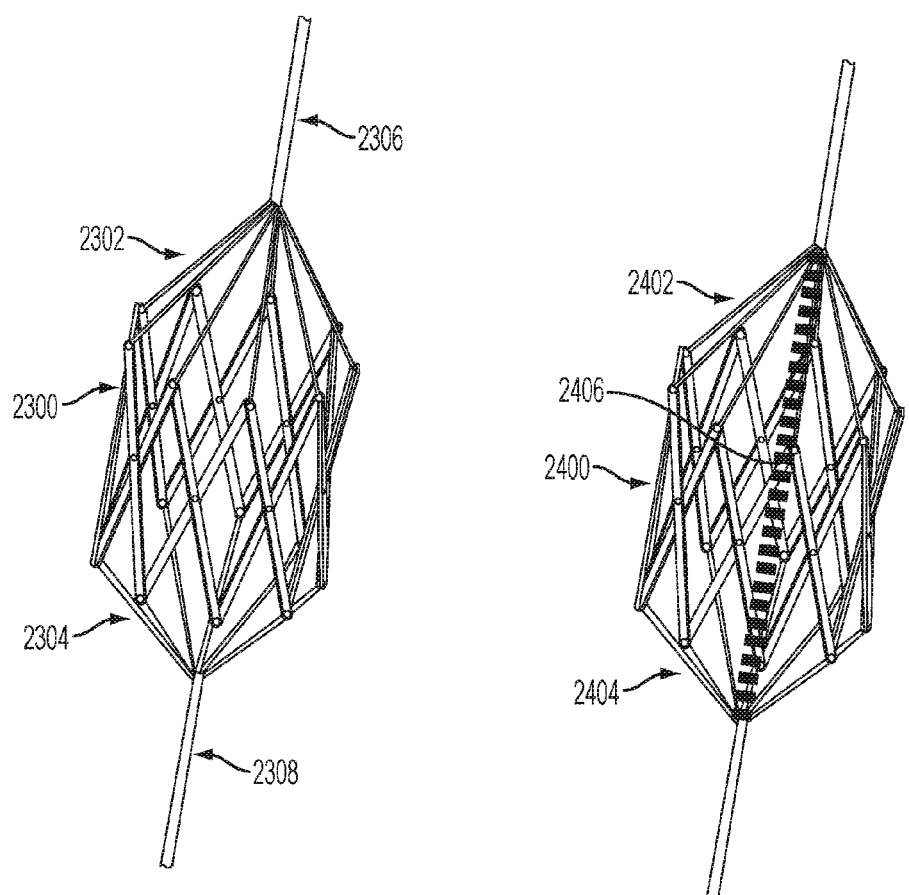
FIG. 23 is a perspective view of an embodiment of an articulated support structure comprising dual deployment wires.
FIG. 24 is a perspective view of an embodiment of an articulated support structure comprising a deployment shaft.

Structures comprising one or two sets of radial struts may be deployed using any of a variety of mechanisms. In FIG. 23, for example, each set of radial struts 2302 and 2304 may articulate with separate deployment structures 2306 and 2308, which, depending upon whether the deployment structures 2306 and 2308 are flexible or rigid, may be configured to deployed by pulling and/or pushing of the deployment structure 2306 and 2308. In other examples, such as the structure 2400 depicted in FIG. 24, both sets of radial struts 2402 and 2404 may be attached to a common deployment structure or assembly 2406, where at least one or both of the attachments of the strut sets 2402 and 204 may be displaced longitudinally to effectuate expansion and/or collapse of the structure 2400.

Particular embodiments of the invention offer distinct advantages over the prior art, including in their structure and applications. While certain advantages are summarized below, the summary is not necessarily a complete list as there may be additional advantages.

The device may allow the user to advert the serious complications that can occur during percutaneous heart valve implantation. Because the device may be configured to be retrievable and re-positionable during implantation into the body, the surgeon may be able to avoid serious complications due to valve mal-positioning or migration during implantation. Examples of these complications include occlusion of the coronary arteries, massive paravalvular leakage, or arrhythmias.

The device may also decrease vascular access complications because of the device's narrow insertion profile. The device's profile may be low, in part, due to its unique geometry, which may allow neighboring struts in the stent to overlap during stent compression. The device's low profile may be further augmented by eliminating the necessity for a balloon or a sheath. In some embodiments, however, the device may be placed within a sheath during insertion. The device's narrow profile offers the advantage of widening the vascular access route options in patients. For instance, the device may enable the delivery of the prosthetic valve through an artery in the leg in a patient whom would have previously been committed to a more invasive approach through the chest wall. The device may therefore decrease complications associated with the use of large profile devices in patients with poor vascular access.

The tissue valve embodiments can offer improved durability by allowing for attachment of the leaflets to flexible commissural posts. The flexible posts may allow dissipation of the stress and strain imposed on the leaflet by the cardiac cycle. The use of multi-ply struts may enable the leaflets to be sandwiched in between the struts, which may re-enforce the leaflet attachments and prevents tearing of sutures and provide a significantly simplified approach for leaflet attachment. The valve may further assume a desirable leaflet morphology, which may further reduce the stress and strain on leaflets. Namely, the angled leaflet attachment to the stent may be similar to the native human aortic valve's inter-leaflet trigone pattern. These properties may significantly improve the longevity of percutaneous heart valve replacement therapies. In addition, in comparison to Nitinol frames, the support structure may have more forceful expansion and higher hoop strength, and may be more fatigue resistant while collapsing more easily. Moreover, it may not require cooling or warning to cause shape changes.

The device could reduce or eliminate arrhthymia complications due to the incremental expansion or compression of the stent. The stent can employ a screw mechanism for deployment, which enables the stent to self-lock or un-lock at all radii. This may enable more controlled deployment and the potential for individualizing the expansion or compression of the device in each patient. Because the expansion or compression of the device may be configured to be reversible at any stage during the procedure, the surgeon may be able to easily reverse the expansion of the device to relieve an arrhythmia. In addition, if an arrhythmia is detected during implantation, the device may be able to be repositioned to further eliminate the problem.

The device may reduce or eliminate paravalvular leak due to the device's ability to be accurately positioned, and re-positioned, if necessary. That may considerably decrease the occurrence and severity of paravalular leaks. The device may also reduce or eliminate paravalvular leak due to the ability to retain a dynamic seal.

The device may eliminate balloon-related complications. The screw mechanism of deployment exploits the mechanical advantage of a screw. This may provide for forceful dilation of the stent. The lever arms created by the pivoting of the struts in the scissor linkage of the stent may transmit a further expansion force to the stent. The stent may be expanded without the need for a balloon. In addition, the device may have the ability to be forcefully dilated, which may reduce or eliminate the need for pre- or postballooning during the implantation procedure in patients.

The device may have more predictable and precise positioning in the body because the difference between the height of the stent in the compressed and expanded position may be small. This "reduced foreshortening" may help the surgeon to position the device in the desirable location in the body. The ability to re-position the device in the body may further confer the ability to precisely position the device in each individual.

In addition to the mechanical advantages, the device may enable a wider population of patients to be treated by a less invasive means for valve replacement. For example, the device may enable patients with co-morbidities, who are not candidates for open chest surgical valve replacement, to be offered a treatment option. The device's ability to assume a narrow profile may also enable patients who were previously denied treatment due to poor vascular access (e.g. tortuous, calcified, or small arteries), to be offered a treatment option. The durability of the valve may expand the use of less-invasive procedures to the population of otherwise healthy patients, who would otherwise be candidates for open chest surgical valve replacement. The device's ability to be forcefully expanded, or assume hourglass, or conical shapes, potentially expands the device application to the treatment of patients diagnosed with aortic insufficiency, as well as aortic stenosis.

The device can also provide a less invasive treatment to patients with degenerative prosthesis from a prior implant, by providing for a "valve-in-valve" procedure. The device could be accurately positioned inside the failing valve, without removing the patient's degenerative prosthesis. It could help the patient by providing a functional valve replacement, without a "re-do" operation and its associated risks.

While this invention has been particularly shown and described with references to particular embodiments, it will be understood by those skilled in the art that various changes in form and details may be made to the embodiments without departing from the scope of the invention encompassed by the appended claims. For the methods disclosed herein, the steps need not be performed sequentially. Each of the features depicted in each embodiment herein in may be adapted for use in other embodiments herein.

I claim:

1. A biocompatible articulated support structure, comprising a tubular support body with a proximal opening, a distal opening, and a lumen and a longitudinal axis between the proximal and distal openings;
   wherein the tubular support body comprises a plurality of discrete struts coupled by a plurality of rotatable hinge joints, each rotatable hinge joint comprising an axis of rotation with a radial orientation;
   wherein the plurality of rotatable hinge joints comprise:
   a set of proximal rotatable hinge joints configured to reside in a proximal plane with the proximal opening;
   a set of distal rotatable hinge joints configured to reside in a distal plane with the distal opening;
   a first set of middle rotatable hinge joints, located between the proximal plane and the distal plane; and
   at least one commissural point hinge joint distal to the distal plane;
   wherein the plurality of discrete struts and the rotatable hinge joints therebetween intrinsically provide a self-expansion force; and
   wherein the plurality of discrete struts comprise a plurality of inner struts and a plurality of outer struts.

2. The biocompatible articulated support structure of claim 1, wherein each of the at least one commissural point hinge joint is linked by at least two of the plurality of discrete struts to two commissural base hinge joints.

3. The biocompatible articulated support structure of claim 2, wherein the two commissural base hinge joints are located at or proximal to the distal plane.

4. The biocompatible articulated support structure of claim 1, wherein the first set of middle rotatable hinge joints, when the tubular support body is in an expanded state, are located closer to the proximal plane than the distal plane.

5. The biocompatible articulated support structure of claim 1, wherein the plurality of inner struts comprises at least one commissural strut, and the plurality of outer struts comprises at least one commissural strut.

6. The biocompatible articulated support structure of claim 1, wherein when the tubular support body is in an expanded state, the average angle of the at least one commissural point hinge joint is less than the average angle of the set of distal rotatable hinge joints.

7. The biocompatible articulated support structure of claim 1, wherein when the tubular support body is in an expanded state, a distance between the at least one commissural point hinge joint and the distal plane is at least 20% of a longitudinal distance between the proximal and distal planes.

8. The biocompatible articulated support structure of claim 1, further comprising an expandable hourglass securing body comprising a proximal opening, and a distal opening, with a lumen and a longitudinal axis between the proximal and distal openings, and wherein the tubular support body is configured to reside within the lumen of the expandable hourglass securing body.

9. The biocompatible articulated support structure of claim 8, wherein the expandable hourglass securing body comprises a distal tapered section, a proximal tapered section, and a narrow section therebetween, and wherein the tubular support body is secured to the narrow section.

10. The biocompatible articulated support structure of claim 9, wherein the expandable hourglass securing body comprises a plurality of discrete non-linear struts interconnected by rotatable hinge joints, each rotatable hinge joint comprising an axis of rotation with a radial orientation.

11. The biocompatible articulated support structure of claim 9, further comprising at least one locking ring secured to at least one of the distal tapered section and the proximal tapered section.

12. The biocompatible articulated support structure of claim 11, wherein the at least one locking ring is located within the lumen of the expandable hourglass securing body.

13. The biocompatible articulated support structure of claim 11, wherein the at least one locking ring comprises a plurality of inner struts and a plurality of outer struts interconnected by rotatable hinge joints, each rotatable hinge joint comprising an axis of rotation with a radial orientation.

* * * * *